US005945522A

United States Patent [19]
Cohen et al.

[11] Patent Number: 5,945,522
[45] Date of Patent: Aug. 31, 1999

[54] PROSTATE CANCER GENE

[75] Inventors: Daniel Cohen, Fontenay-sous-bois; Ilya Chumakov, Vaux-le-Penil; Marta Blumenfeld, Paris; Lydie Bougueleret, Vanves, all of France

[73] Assignee: GENSET, Paris, France

[21] Appl. No.: 08/996,306

[22] Filed: Dec. 22, 1997

[51] Int. Cl.⁶ ............ C07H 21/02; C07H 21/04; C12Q 1/68
[52] U.S. Cl. ............ 536/23.1; 435/6; 536/24.1; 536/24.31; 536/24.32; 536/24.33; 536/24.3
[58] Field of Search ............ 435/6; 536/24.3, 536/24.31, 24.32, 24.33, 24.1, 23.1

[56] References Cited

U.S. PATENT DOCUMENTS 5,807,680   9/1998   Sutcliffe et al. ............ 435/6

OTHER PUBLICATIONS

Auffray, et al., "[IMAGE: molecular integration of the analysis of the human genome and its expression]", C R Acad Sci III, 318(2) pp. 263–2721 (Feb. 1995).
Ashagbley, et al., "Synthesis of Ether–Linked Analogues of Lysophosphatidate and their Effect on the Proliferation of Human Epithelial Cancer Cells", Anticancer Research, 16(4A): 1813–1818 (1996).
Coleman, J., "Characterizaiton of the *Escherichia coli* gene for 1–acyl–sn–glycerol–3–phosphate acyltransferase (plsC)", Mol. Gen. Genet, 232(2) :295–303 (1992).
Chumakov, et al., "A YAC contig map of the human genome", Nature, 377 Supp : 175–297 (1995).
Durieux, et al., "Signalling properties of lysophosphatidic acid", Trends in Pharmacol. Sci., 14(6) : 249–254 (1993).
Eberhardt, et al., "Human Lysophosphatidic Acid Acyltransferase", J. Biol. Chem. 272(32) : 20299–20305 (1997).
Emi, et al., "Frequent Loss of Heterozygosity for Loci on Chromosome 8p in Hepatocellular Carcinoma, Colorectal Cancer, and Lung Cancer", Cancer Research, 52(19): 5368–5372 (1992).
Faas, et al., "Increased phospholipid fatty acid remodeling in human and rat prostatic adenocarcinoma tissues", J. Urol (Baltimore), 156(1): 243–248 (1996).
Gronwald, et al., "Comparison of DNA Gains and Losses in Primary Renal Clear Cell Carcinomas and Metastatic Sites: Importance of 1q and 3p Copy Number Changes in Metastatic Events", Cancer Research, 57(3) : 481–487 (1997).
Gu, et al., "Identification cloning, and expression of a cytosolic megakaryocyte protein–tyrosine–phosphatase with sequence homology to cytoskeletal protein 4.1", Proc. Natl. Acad. Sci. USA, 88(13)): P5867–71 (1991).
Hsuan, et al., "Growth Factor–dependent Phosphoinositide Signalling", Int. J. Biochem. Cell. Biol., 29(3) : 415–435 (1997).
Ichikawa, et al., "*"Prostate Suppl., 6 : 31–35 (1996).
Kume, et al., "cDNA Cloning and Expression of Murine 1–Acyl–sn–glycerol–3–phosphate Acyltransferase", Biochemical and Biophysical Research Communications, 237(3) : 663–666 (1997).

Levine, et al., "Lysophosphatidic acid: a novel growth and survival factor for renal proximal tubular cells", American Physiological Society, 273(4PT2) : F575–F585 (1997).
Martin, T.F.J., "Phosphoinositides as spatial regulators of membrane traffic", Curr. Opin. Neurobiol., 7(3) : 331–338 (1997.
Matsuyama, et al., "Deletion mapping of chromosome 8p in prostate cancer by fluorescense in situ hybridization", Oncogene, 9(10 :3071–3076 (1994).
Nagai, et al., "Comprehensive allelotyping of human hepatocellular carcinoma", Oncogene, 14(24) :2927–2933 (1997).
Nagiec, et al., "A Suppressor Gene That Enables *Saccharomyces cerevisiae* to Grow without Making Sphingolipids Encodes a Protein That Resembles an *Escherichia coli* Fatty Acyltransferase", Journal of Biological Chemistry, 268(29): 22156–22163 (1993).
Qi C, et al., "Lysophosphatidic acid stimulates phospholipase D activity and cell proliferation in PC–3 human prostate cancer cells", J. Cell. Physiol., 174(2) : 261–272 (1998).
Scholnick, et al., "Chromosome 8 Alleic Loss and the Outcome of Patients With Squamous Cell Carcinoma of the Supraglottic Larynx", Journal of the National Cancer Institute, 88(22) : 1676–1682 (1996).
Sunkara, et al., A novel class of low molecular weight (MW) phospholipid (PL) signaling inhibitors is selectively cytotoxi for tumor cells (Meeting abstract): & Proc Annu Meet Am Assoc Cancer Res, 35: A2441 (1994).
Sunwoo, et al., "Evidence of Multiple Tumor Suppressor Genes on Chromosome Arm 8p in Supraglottic Laryngeal Cancer", Genes, Chromosomes & Cancer, 16 :167–169 (1996).
Toker, et al., "Signalling through the lipid products of phosphoinositid–3–OH kinase", Nature, 387 : 673–676 (1997).
Washburn, et al., "Deletion of loci mapping to 8p23–pter in human prostate cancers", Proceedings of the American Association for Cancer Research, 38(#3456) : 515 (Mar. 1997).
Wilson, et al., "2.2 M6 of contiguous nucleotide sequence from chromosome III of *C. elegans*", Nature 368(6466): pp. 32–38 (1994).
Yaremko, et al., :Deletion Mapping Reveals Two Regions of Chromosome 8 Allele Loss in Colorectal Carcinomas, Genes, Chromosomes & Cancer, 10 : 1–6 (1994).
SwissProt: P26647, date Nov. 1, 1998.

(List continued on next page.)

*Primary Examiner*—Jeffrey Fredman
*Attorney, Agent, or Firm*—Knobbe, Martens, Olson & Bear LLP

[57] ABSTRACT

The present invention relates to PG1, a gene associated with prostate cancer. The invention also relates to methods of determining whether an individual is at risk for developing prostate cancer at a later date or whether an individual suffers from prostate cancer as a result of a mutation in the PG1 gene.

7 Claims, 10 Drawing Sheets

OTHER PUBLICATIONS

SwissProt: P33333, date Nov. 1, 1998.
SwissProt: P38226, date Nov. 1, 1997.
Genbank Accession No. Z29518, date Nov. 12, 1994.
Genbank Accession No. AB005623, date Oct. 6, 1997.
Genbank Accession No. U56417, date Jun. 4, 1997.
Genbank Accession No. U89336, date Feb. 15, 1997.
Genbank Accession No. Z49860, date Jan. 6, 1996.
Genbank Accession No. Z49770, date Aug. 11, 1997.
Genbank Accession No. Z72511, date Sep. 21, 1998.
Genbank Accession No. AF003136, date Dec. 31, 1997.
Search Report listing sequence EMEST7, Accession No. AA280082.
Public Database Chart.
Patented Sequences Database Chart.
West et al, "Cloning and expression of two human lysophosphatidic acid acyltransferase cDNAs that enhance cytokine–induced signaling responses in cells", DNA Cell Biol. 16(6):691–701, Jun. 1997.
Bender et al, Genbank Locus MUSPHKGZ, Accession No. L08057, Sep. 1995.
Hillier et al, Genbank Locus AA056643, Accession No. AA056643, May 1997.
Auffray et al, Genbank Locus HSC2CG051, Accession No. Z45294, Sep. 1995.
Hillier et al, Genbank Locus WO1144, Accession No. WO1144, Apr. 1996.
Auffray et al, Genbank Locus HSC2E00111, Accession No. Z44999, Sep. 1995.
Stratagene Catalog, pp. 62–63, 1995.

HAPLOTYPE FREQUENCY ANALYSIS

| POPULATIONS | AFFECTED CASES 2 (281) | UNAFFECTED CONTROLS 3 (130) |
|---|---|---|
| CHARACTERISTICS OF POPULATIONS | 143 SPORADIC CASES +138 FAMILIAL CASES | >65 YEARS PSA<4 |

| MARKERS | 99-123 | 4-26 | 4-14 | 4-77 | 99-217 | 4-67 | 99-213 | 99-221 | 99-135 | HAPLOTYPE FREQUENCIES | | RELATIVE RISK | PVALUE |
|---|---|---|---|---|---|---|---|---|---|---|---|---|---|
| BACS | H0287B09 | B0189E08 | | | B0463F01 | | | B0725B12 | | | | | |
| CONTIGS | | | 11453 | | | | | | | | | | |
| GENES | | | | ←PG1→ | | | | | | | | | |
| P VALUE | 2,00E-01 * | 1,00E-01 * | 1,00E-01 * | 2,00E-02 ** | 2,00E-02 ** | 9,00E-04 *** | 6,00E-02 * | 7,00E-02 * | 2,00E-01 * | CASES (2) | CONTROLS (3) | | |
| DISTANCE BETWEEN MARKERS(KB) | <18KB> | <15KB> | <88KB> | <22KB> | <17KB> | <15KB> | <29KB> | >100KB< | | | | | |
| HAPLOTYPE 8>304KB< | C | A | C | G | T | G | A | A | | 0,075 | 0,018 | 4,42 | 9,00E-04 *** |
| HAPLOTYPE 7>286KB< | | A | C | G | T | G | A | A | | 0,095 | 0,016 | 6,46 | 6,00E-05 **** |
| HAPLOTYPE 6<186KB> | | A | C | G | T | G | A | | | 0,116 | 0,019 | 6,78 | 1,00E-05 ***** |
| HAPLOTYPE 5<171KB> | | | C | G | T | G | A | | | 0,117 | 0,013 | 10,06 | **9,00E-07 *******| 
| HAPLOTYPE 4<83KB> | | | | G | T | G | A | | | 0,117 | 0,025 | 5,17 | 2,00E-05 ****** |
| HAPLOTYPE 3.1<54KB> | | | | | T | G | A | | | 0,117 | 0,027 | 4,78 | 2,00E-05 ***** |
| HAPLOTYPE 3.2<54KB> | | | | G | T | G | | | | 0,222 | 0,109 | 2,33 | 4,00E-05 ****** |
| HAPLOTYPE 2.2<39KB> | | | | G | T | G | | | | 0,251 | 0,134 | 2,17 | 2,00E-04 **** |
| HAPLOTYPE 2<32KB> | | | | | T | G | | | | 0,226 | 0,112 | 2,32 | 1,00E-04 *** |
| HAPLOTYPE 1.1<17KB> | | | | | T | | | | | 0,256 | 0,146 | 2,01 | 3,00E-04 **** |
| HAPLOTYPE 1.2<15KB> | | | | | T | G | | | | 0,233 | 0,129 | 2,05 | 6,00E-04 *** |

| BAC | MARKER | SEQ ID N° | SEQ ID N°(MUT) | PU SEQUENCE | SEQ ID N° | RP SEQUENCE | SEQ ID N° | POLYMORPHISM POSITION* | BASE | MICROSEQ. OLIGOS POSITIONS* | |
|---|---|---|---|---|---|---|---|---|---|---|---|
| 228 | 99-123 | 21 | 30 | AAAGCCAGGACTAGAAGG | 39 | TATTCAGAAAGGAGTGGG | 48 | 24 | C/T | 1-23 | 25-47 (COMPLEMENTARY) |
| 189 | 4-26 | 22 | 31 | TACAGCCCTGTAAGACAC | 40 | TGAGGACTGCTAGGAAAG | 49 | 24 | A/G | 1-23 | 25-47 (COMPLEMENTARY) |
| 228/189 | 4-14 | 23 | 32 | TCTAACCTCTCATCCAAC | 41 | GACTGTATCCTTTGATGCAC | 50 | 24 | C/C | 1-23 | 25-47 (COMPLEMENTARY) |
| 189/463 | 4-77 | 24 | 33 | TGTTGATTTACAGGCGGC | 42 | GGAAAGGTACTCATTCATAG | 51 | 24 | G/T | 1-23 | 25-47 (COMPLEMENTARY) |
| 463 | 99-217 | 25 | 34 | GGTGGGAATTTACTATATG | 43 | GTTTATTTGTGTGAGCTTTG | 52 | 24 | C/T | 1-23 | 25-47 (COMPLEMENTARY) |
| 189/463 | 4-67 | 26 | 35 | AAGTTCACCTTTATTCTCTGG | 44 | TGAAAGAGTTTATTCTCTGG | 53 | 24 | C/T | 1-23 | 25-47 (COMPLEMENTARY) |
| 463 | 99-213 | 27 | 36 | ATACTGGCAGCGTGTGCTTC | 45 | TTATTGCCCCACATGCTTGAG | 54 | 24 | C/T | 1-23 | 25-47 (COMPLEMENTARY) |
| 463 | 99-221 | 28 | 37 | CCCTTTTCTTCACTGTC | 46 | TCATTCGTCTGGCTAGGTC | 55 | 24 | A/C | 1-23 | 25-47 (COMPLEMENTARY) |
| 725 | 99-135 | 29 | 38 | TGGAAGTTGTTATTGCCC | 47 | AAACACCTCCCATTGTGC | 56 | 24 | A/G | 1-23 | 25-47 (COMPLEMENTARY) |

*: POSITIONS ARE GIVEN RELATIVE TO THE SEQUENCE OF THE CORRESPONDING MARKER (i.e. SEQ ID N° 21-38 AND 57-62)

FIG. 6B

| BAC | MARKER | SEQ ID N° | SEQ ID N°(MUT) | PU SEQUENCE | SEQ ID N° | RP SEQUENCE | SEQ ID N° | POLYMORPHISM POSITION* | BASE | MICROSEQ. OLIGOS POSITIONS* | |
|---|---|---|---|---|---|---|---|---|---|---|---|
| 189/463 | 99-1482 | 57 | 60 | ATCAAATCAGTGAAGTCTGAG | 63 | ACAAATCTATATAAGGCTGG | 66 | 24 | A/C | 1-23 | 25-47 (COMPLEMENTARY) |
| 463 | 4-73 | 58 | 61 | ATCGCTGGAACATTCTGG | 64 | CTCTTGGTTAAACAGCAGTG | 67 | 24 | G/C | 1-23 | 25-47 (COMPLEMENTARY) |
| 463 | 4-65 | 59 | 62 | GATTTAAGCTACGCTATTAG | 65 | TGGCTCTGCATTTCTCC | 68 | 24 | C/T | 1-23 | 25-47 (COMPLEMENTARY) |

*: POSITIONS ARE GIVEN RELATIVE TO THE SEQUENCE OF THE CORRESPONDING MARKER (i.e. SEQ ID N° 21-38 AND 57-62)

| EXON Phase | START | END | 5' SPsite | PHASE | 3' SPsite |
|---|---|---|---|---|---|
| Ex1 +0 | 2001 | 2216 | | | GTGAGC |
| Ex2 +1 | 18196 | 18265 | TAG | +0 | GTTTGTA |
| Ex3 +0 | 23717 | 23832 | CAG | +2 | GTAACT |
| Ex4 +0 | 25571 | 25660 | CAG | +0 | GTAAGA |
| Ex5 +2 | 34669 | 34759 | CAG | +0 | GTAAGT |
| Ex6 +1 | 40688 | 40846 | TAG | +1 | GTAAGT |
| Ex7 +2 | 48070 | 48193 | TAG | +2 | GTGAGT |
| Ex8 | 50182 | 54523 | TAG | +1 | |
| ATG codon | 2031 | 2033 | | | |
| STOP codon | 50405 | 50407 | | | |
| POLY Ad site | 54445 | 54450 | | | |

*FIG. 7*

|  |  | box1 | box2 | box3 |
|---|---|---|---|---|
| PG1 | Hs | NHQ *81-83* | FPEGTR *160-165* | LDAIYDVTV *211-219* |
| AF003136 (Genbank) | Ce | NHQ *630-632* | FPEGTR *712-717* | LDAIYDVTV *762-770* |
| Z72511 (Genbank) | Ce | 48 NHR 50 | FPEGTD *129-134* | VEYIYDITI *204-212* |
| P38226 (Swissprot) | Sc | 111 NHQ 113 | FPEGTN *223-228* | IESLYDITI *271-279* |
| P33333 (Swissprot) | Sc | 81 NHQ 83 | FPEGTR *154-159* | - |
| Z49770 (Genbank) | Sc | 116 NHQ 118 | FPEGTN *215-220* | LDAIYDVTI *265-273* |
| P26647 (Swissprot) | Ec | 72 NHQ 74 | FPEGTR *145-150* | - |
| Z49860 (Genbank) | Bn | - | FVEGTR *90-95* | VPAIYDMTV *138-146* |
| U89336 (Genbank) | Hs | 95 NHQ 97 | FPEGTR *168-173* | - |
| U56417 (Genbank) | Hs | 103 NHQ 105 | FPEGTR *176-181* | - |
| AB005623 (Genbank) | Mm | 100 NHQ 102 | FPEGTR *173-178* | - |
| Z29518 (Genbank) | Zm | 91 NHR 93 | FVEGTR *170-175* | VPAIYDTTV *218-226* |

Hs = Homo sapiens, Ce = Caenorabibtis elegans, Ec = Escherichia coli; Sc = Saccharomyces cerevisiae, Bn = Brassica napus, Zm = Zea maize, Mm = Mus musculus

- = pattern absent from protein sequence

Note: Functional acyl glycerol transferases all contain boxes 1 and 2 and not box 3. Proteins most related to PG1 contain the 3 boxes with a high degree of conservation.

FIG. 9

PROSTATE CANCER GENE

BACKGROUND OF THE INVENTION

A cancer is a clonal proliferation of cells produced as a consequence of cumulative genetic damage that finally results in unrestrained cell growth, tissue invasion and metastasis (cell transformation). Regardless of the type of cancer, transformed cells carry damaged DNA in many forms: as gross chromosomal translocations or, more subtly, as DNA amplification, rearrangement or even point mutations.

Some oncogenic mutations may be inherited in the germline, thus predisposing the mutation carrier to an increased risk of cancer. However, in a majority of cases, cancer does not occur as a simple monogenic disease with clear Mendelian inheritance. There is only a two- or three-fold increased risk of cancer among first-degree relatives for many cancers (Mulvihill J J, Miller R W & Fraumeni J F, 1977, Genetics of human cancer Vol 3, New York Raven Press). Alternatively, DNA damage may be acquired somatically, probably induced by exposure to environmental carcinogens. Somatic mutations are generally responsible for the vast majority of cancer cases.

Studies of the age dependence of cancer have suggested that several successive mutations are needed to convert a normal cell into an invasive carcinoma. Since human mutation rates are typically $10^{-6}$/gene/cell, the chance of a single cell undergoing many independent mutations is very low (Loeb L A, Cancer Res 1991, 51: 3075–3079). Cancer nevertheless happens because of a combination of two mechanisms. Some mutations enhance cell proliferation, increasing the target population of cells for the next mutation. Other mutations affect the stability of the entire genome, increasing the overall mutation rate, as in the case of mismatch repair proteins (reviewed in Arnheim N & Shibata D, Curr. Op. Genetics & Development, 1997, 7: 364–370).

An intricate process known as the cell cycle drives normal proliferation of cells in an organism. Regulation of the extent of cell cycle activity and the orderly execution of sequential steps within the cycle ensure the normal development and homeostasis of the organism. Conversely, many of the properties of cancer cells—uncontrolled proliferation, increased mutation rate, abnormal translocations and gene amplifications—can be attributed directly to perturbations of the normal regulation or progression of the cycle. In fact, many of the genes that have been identified over the past several decades as being involved in cancer, can now be appreciated in terms of their direct or indirect role in either regulating entry into the cell cycle or coordinating events within the cell cycle.

Recent studies have identified three groups of genes which are frequently mutated in cancer. The first group of genes, called oncogenes, are genes whose products activate cell proliferation. The normal non-mutant versions are called protooncogenes. The mutated forms are excessively or inappropriately active in promoting cell proliferation, and act in the cell in a dominant way in that a single mutant allele is enough to affect the cell phenotype. Activated oncogenes are rarely transmitted as germline mutations since they may probably be lethal when expressed in all the cells. Therefore oncogenes can only be investigated in tumor tissues.

Oncogenes and protooncogenes can be classified into several different categories according to their function. This classification includes genes that code for proteins involved in signal transduction such as: growth factors (i.e., sis, int-2); receptor and non-receptor protein-tyrosine kinases (i.e., erbB, src, bcr-abl, met, trk); membrane-associated G proteins (i.e., ras); cytoplasmic protein kinases (i.e., mitogen-activated protein kinase—MAPK-family, raf, mos, pak), or nuclear transcription factors (i.e., myc, myb, fos, jun, rel) (for review see Hunter T, 1991 Cell 64: 249; Fanger G R et al., 1997 Curr.Op.Genet.Dev.7: 67–74; Weiss F U et al., ibid. 80–86).

The second group of genes which are frequently mutated in cancer, called tumor suppressor genes, are genes whose products inhibit cell growth. Mutant versions in cancer cells have lost their normal function, and act in the cell in a recessive way in that both copies of the gene must be inactivated in order to change the cell phenotype. Most importantly, the tumor phenotype can be rescued by the wild type allele, as shown by cell fusion experiments first described by Harris and colleagues (Harris H et al.,1969, Nature 223: 363–368). Germline mutations of tumor suppressor genes may be transmitted and thus studied in both constitutional and tumor DNA from familial or sporadic cases. The current family of tumor suppressors includes DNA-binding transcription factors (i.e., p53, WT1), transcription regulators (i.e., RB, APC, probably BRCA1), protein kinase inhibitors (i.e., p16), among others (for review, see Haber D & Harlow E, 1997, Nature Genet. 16: 320–322).

The third group of genes which are frequently mutated in cancer, called mutator genes, are responsible for maintaining genome integrity and/or low mutation rates. Loss of function of both alleles increase cell mutation rates, and as consequence, protooncogenes and tumor suppressor genes may be mutated. Mutator genes can also be classified as tumor suppressor genes, except for the fact that tumorigenesis caused by this class of genes cannot be suppressed simply by restoration of a wild-type allele, as described above. Genes whose inactivation may lead to a mutator phenotype include mismatch repair genes (i.e., MLH1, MSH2), DNA helicases (i.e., BLM, WRN) or other genes involved in DNA repair and genomic stability (i.e., p53, possibly BRCA1 and BRCA2) (For review see Haber D & Harlow E, 1997, Nature Genet. 16: 320–322; Fishel R & Wilson T. 1997, Curr.Op.Genet.Dev.7: 105–113; Ellis NA,1997 ibid.354–363).

The recent development of sophisticated techniques for genetic mapping has resulted in an ever expanding list of genes associated with particular types of human cancers. The human haploid genome contains an estimated 80,000 to 100,000 genes scattered on a $3 \times 10^9$ base-long double-stranded DNA. Each human being is diploid, i.e., possesses two haploid genomes, one from paternal origin, the other from maternal origin. The sequence of a given genetic locus may vary between individuals in a population or between the two copies of the locus on the chromosomes of a single individual. Genetic mapping techniques often exploit these differences, which are called polymorphisms, to map the location of genes associated with human phenotypes.

One mapping technique, called the loss of heterozygosity (LOH) technique, is often employed to detect genes in which a loss of function results in a cancer, such as the tumor suppressor genes described above. Tumor suppressor genes often produce cancer via a two hit mechanism in which a first mutation, such as a point mutation (or a small deletion or insertion) inactivates one allele of the tumor suppressor gene. Often, this first mutation is inherited from generation to generation.

A second mutation, often a spontaneous somatic mutation such as a deletion which deletes all or part of the chromosome carrying the other copy of the tumor suppressor gene, results in a cell in which both copies of the tumor suppressor gene are inactive.

As a consequence of the deletion in the tumor suppressor gene, one allele is lost for any genetic marker located close to the tumor suppressor gene. Thus, if the patient is heterozygous for a marker, the tumor tissue loses heterozygosity, becoming homozygous or hemizygous. This loss of heterozygosity generally provides strong evidence for the existence of a tumor suppressor gene in the lost region.

By genotyping pairs of blood and tumor samples from affected individuals with a set of highly polymorphic genetic markers, such as microsatellites, covering the whole genome, one can discover candidate locations for tumor suppressor genes. Due to the presence of contaminant non-tumor tissue in most pathological tumor samples, a decreased relative intensity rather than total loss of heterozygosity of informative microsatellites is observed in the tumor samples. Therefore, classic LOH analysis generally requires quantitative PCR analysis, often limiting the power of detection of this technique. Another limitation of LOH studies resides on the fact that they only allow the definition of rather large candidate regions, typically spanning over several megabases. Refinement of such candidate regions requires the definition of the minimally overlapping portion of LOH regions identified in tumor tissues from several hundreds of affected patients.

Another approach to genetic mapping, called linkage analysis, is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offspring of all families. Those that co-segregate with the trait are tracked. After pooling data from all families, statistical methods are used to determine the likelihood that the marker and the trait are segregating independently in all families. As a result of the statistical analysis, one or several regions are selected as candidates, based on their high probability to carry a trait causing allele. The result of linkage analysis is considered as significant when the chance of independent segregation is lower than 1 in 1000 (expressed as a LOD score>3). Identification of recombinant individuals using additional markers allows further delineation of the candidate linked region, which most usually ranges from 2 to 20 Mb.

Linkage analysis studies have generally relied on the use of microsatellite markers (also called simple tandem repeat polymorphisms, or simple sequence length polymorphisms). These include small arrays of tandem repeats of simple sequences (di-tri-tetra-nucleotide repeats), which exhibit a high degree of length polymorphism, and thus a high level of informativeness. To date, only just more than 5,000 microsatellites have been ordered along the human genome (Dib et al., Nature 1996, 380: 152), thus limiting the maximum attainable resolution of linkage analysis to ca. 600 kb on average.

Linkage analysis has been successfully applied to map simple genetic traits that show clear Mendelian inheritance patterns. About 100 pathological trait-causing genes were discovered by linkage analysis over the last 10 years.

However, linkage analysis approaches have proven difficult for complex genetic traits, those probably due to the combined action of multiple genes and/or environmental factors. In such cases, too large an effort and cost are needed to recruit the adequate number of affected families required for applying linkage analysis to these situations, as recently discussed by Risch, N. and Merikangas, K. (Science 1996, 273: 1516–1517). Finally, linkage analysis cannot be applied to the study of traits for which no available large informative families are available. Typically, this will be the case in any attempt to identify trait-causing alleles involved in sporadic cases.

Despite the significant progress in identifying genes associated with cancer, there remains a need for the identification and characterization of additional cancer genes. The present invention relates to the identification of a gene associated with prostate cancer, identified as the PG1 gene, and reagents, diagnostics, and therapies related thereto.

SUMMARY OF THE INVENTION

The present invention relates to the PG1 gene, a gene associated with prostate cancer. One embodiment of the invention is a purified or isolated nucleic acid comprising the sequence of SEQ ID NO: 1 or the sequence complementary thereto. As used herein, the term "purified" does not require absolute purity; rather, it is intended as a relative definition Purification of starting material or natural material to at least one order of magnitude, preferably two or three orders, and more preferably four or five orders of magnitude is expressly contemplated As used herein, the term "isolated" requires that the material be removed from its original environment (e.g., the natural environment if it is naturally occurring).

Another embodiment of the present invention is a purified or isolated nucleic acid comprising at least 10 consecutive nucleotides of the sequence of SEQ ID NO: 1 or the sequence complementary thereto. In one aspect of this embodiment, the nucleic acid the nucleic acid comprises at least 15 consecutive nucleotides of the sequence of SEQ ID NO: 1 or the sequence complementary thereto. In another aspect of this embodiment, the nucleic acid comprises one or more exons from the sequence of SEQ ID NO: 1. In yet another aspect of this embodiment, the nucleic acid comprises nucleotides 1629 through 1870 of the sequence of SEQ ID NO: 1.

A further embodiment of the present invention is a purified or isolated nucleic acid comprising the sequence of SEQ ID NO: 3 or the sequence complementary thereto.

Another embodiment of the present invention is a purified or isolated nucleic acid comprising at least 10 consecutive nucleotides of the sequence of SEQ ID NO: 3 or the sequence complementary thereto. In one aspect of this embodiment the nucleic acid comprises at least 15 consecutive nucleotides of the sequence of SEQ ID NO: 3 or the sequence complementary thereto.

Another embodiment of the present invention is a purified or isolated nucleic acid encoding the polypeptide of SEQ ID NO: 4.

Yet another embodiment of the present invention is apurified or isolated nucleic acid encoding at least 10 consecutive amino acids of the polypeptide of SEQ ID NO: 4. In one aspect of this embodiment, the nucleic acid encodes at least 15 consecutive amino acids of the polypeptide of SEQ ID NO: 4.

Another embodiment of the present invention is a purified or isolated polypeptide having the sequence of the polypeptide of SEQ ID NO: 4.

Another embodiment of the present invention is a purified or isolated polypeptide comprising at least 10 consecutive amino acids of the polypeptide of SEQ ID NO: 4. In one aspect of this embodiment, the polypeptide comprises at least 15 consecutive amino acids of the SEQ ID NO: 4.

Another embodiment of the present invention is a purified or isolated antibody capable of specifically binding to protein having the sequence of SEQ ID NO: 4. In one aspect of this embodiment, the antibody is capable of binding to a polypeptide comprising at least 10 consecutive amino acids of the protein of SEQ ID NO: 4.

Another embodiment of the present invention is a host cell containing a nucleic acid comprising the sequence of SEQ ID NO: 1 or the sequence complementary thereto.

Another embodiment of the present invention is a host cell containing a nucleic acid comprising the sequence of SEQ ID NO: 3 or the sequence complementary thereto.

Another embodiment of the present invention is a purified or isolated nucleic acid encoding the PG1 protein, said purified or isolated nucleic acid comprising a sequence selected from the group consisting of SEQ ID NO: 24, SEQ ID NO: 33, SEQ ID NO: 25, SEQ ID NO: 34, SEQ ID NO: 26, SEQ ID NO: 35, SEQ ID NO: 58, SEQ ID NO: 59, SEQ ID NO: 61, and SEQ ID NO: 62.

Another embodiment of the present invention is a purified or isolated nucleic acid comprising a sequence selected from the group consisting of SEQ ID Nos. 21–38 or the sequences complementary thereto.

Another embodiment of the present invention is a purified or isolated nucleic acid comprising at least 10 consecutive nucleotides of the sequences selected from the group consisting of SEQ ID Nos. 21–38 or the sequences complementary thereto. In one aspect of this embodiment, the nucleic acid comprises at least 15 consecutive nucleotides of a sequence selected from the group consisting of SEQ ID Nos. 21–38 or the sequences complementary thereto.

Another embodiment of the present invention is a purified or isolated nucleic acid comprising a sequence selected from the group consisting of SEQ ID NOs: 57–62 or the sequences complementary thereto.

Another embodiment of the present invention is a purified or isolated nucleic acid comprising at least 10 consecutive nucleotides of a sequence selected from the group consisting of SEQ ID NOs: 57–62 or the sequences complementary thereto. In one aspect of this embodiment, the nucleic acid comprises at least 15 consecutive nucleotides of a sequence selected from the group consisting of SEQ ID NOs: 57–62 or the sequences complementary thereto.

Another embodiment of the present invention is a method of determining whether an individual is at risk of developing prostate cancer at a later date or whether the individual suffers from prostate cancer as a result of a mutation in the PG1 gene comprising obtaining a nucleic acid sample from the individual; and determining whether the nucleotides present at one or more of the polymorphic bases in the sequences selected from the group consisting of SEQ ID Nos: 21–38 are indicative of a risk of developing prostate cancer at a later date or indicative of prostate cancer resulting from a mutation in the PG1 gene.

Another embodiment of the present invention is a method of determining whether an individual is at risk of developing prostate cancer at a later date or whether the individual suffers from prostate cancer as a result of a mutation in the PG1 gene comprising obtaining a nucleic acid sample from the individual and determining whether the nucleotides present at one or more of the polymorphic bases in the sequences selected from the group consisting of SEQ ID Nos: 57–62 are indicative of a risk of developing prostate cancer at a later date or indicative of prostate cancer resulting from a mutation in the PG1 gene.

Another embodiment of the present invention is a method of obtaining an allele of the PG1 gene which is associated with a detectable phenotype comprising obtaining a nucleic acid sample from an individual expressing the detectable phenotype, contacting the nucleic acid sample with an agent capable of specifically detecting a nucleic acid encoding the PG1 protein, and isolating the nucleic acid encoding the PG1 protein. In one aspect of this method, the contacting step comprises contacting the nucleic acid sample with at least one nucleic acid probe capable of specifically hybridizing to said nucleic acid encoding the PG1 protein. In another aspect of this embodiment, the contacting step comprises contacting the nucleic acid sample with an antibody capable of specifically binding to the PG1 protein. In another aspect of this embodiment, the step of obtaining a nucleic acid sample from an individual expressing a detectable phenotype comprises obtaining a nucleic acid sample from an individual suffering from prostate cancer.

Another embodiment of the present invention is a nucleic acid encoding the PG1 protein which is obtainable by the method described above.

Another embodiment of the present invention is a nucleic acid comprising at least 10 consecutive nucleotides of a nucleic acid encoding the PG1 protein which is obtainable by the method described above. In one aspect of this embodiment the nucleic acid comprises at least 15 consecutive nucleotides of a nucleic acid encoding the PG1 protein which is obtainable by the method described above.

Another embodiment of the present invention is a host cell containing a nucleic acid encoding the PG1 protein which is obtainable by the method described above.

Another embodiment of the present invention is a purified or isolated protein encoded by the nucleic acid encoding the PG1 protein which is obtainable by the method described above or a fragment comprising at least 10 consecutive amino acids of the protein.

Another embodiment of the present invention is a method of obtaining an allele of the PG1 gene which is associated with a detectable phenotype comprising obtaining a nucleic acid sample from an individual expressing the detectable phenotype, contacting the nucleic acid sample with an agent capable of specifically detecting a sequence within the 8p23 region of the human genome, identifying a nucleic acid encoding the PG1 protein in the nucleic acid sample, and isolating the nucleic acid encoding the PG1 protein. In one aspect of this embodiment, the nucleic acid sample is obtained from an individual suffering from prostate cancer.

Another embodiment of the present invention is a nucleic acid encoding the PG1 protein which is obtainable by the method of the preceding paragraph.

Another embodiment of the present invention is a nucleic acid comprising at least 10 consecutive nucleotides of a nucleic acid encoding the PG1 protein which is obtainable by the method above. In one aspect of this embodiment, the nucleic acid comprises at least 15 consecutive nucleotides of a nucleic acid encoding the PG1 protein which is obtainable by the method above.

Another embodiment of the present invention is a host cell containing a nucleic acid encoding the PG1 protein which is obtainable by the method above.

Another embodiment of the present invention is a purified or isolated protein encoded by a nucleic acid encoding the PG1 protein which is obtainable by the method above or a fragment comprising at least 10 consecutive amino acids thereof.

Another embodiment of the present invention is an improvement an an array of cDNAs or fragments thereof of at least 15 nucleotides in length which comprises inclusion in the array of at least one of the sequences selected from the group consisting of SEQ ID NOs: 21–38, SEQ ID NOs: 57–62, SEQ ID NO: 3, and SEQ ID NO: 1 or the sequences complementary thereto or a fragment thereof of at least 15 consecutive nucleotides. In one aspect of this embodiment, the array includes therein at least two of the sequences selected from the group consisting of SEQ ID NOs: or the sequences complementary thereto or a fragment thereof of at least 15 consecutive nucleotides. In another aspect of this embodiment, the array includes therein at least four of the sequences selected from SEQ ID NOs: 21–38, SEQ ID NOs: 57–62, SEQ ID NO:3, and SEQ ID NO:1 or the sequences complementary thereto or a fragment thereof of at least 15 consecutive nucleotides.

Another embodiment of the present invention is a method of categorizing the risk of prostate cancer in an individual comprising the step of assaying a sample taken from the individual to determine whether the individual carries an allelic variant of PG1 associated with an increased risk of prostate cancer. In one aspect of this embodiment, the sample is a nucleic acid sample. In another aspect of this embodiment, the sample is a protein sample. In another aspect of this embodiment, the method further comprises determining whether the PG1 protein in the sample binds an antibody specific for a PG1 isoform associated with prostate cancer.

Another embodiment of the present invention is a method of categorizing the risk of prostate cancer in an individual comprising the step of determining whether the identities of the polymorphic bases of one or more bi-allelic markers which are in linkage disequilibrium with the PG1 gene are indicative of an increased risk of prostate cancer.

Another embodiment of the present invention is a purified or isolated nucleic acid encoding the protein of SEQ ID NO:5.

Another embodiment of the present invention is a host cell containing a nucleic acid comprising at least 10 consecutive nucleotides of the sequence of SEQ ID NO: 1 or the sequence complementary thereto.

Another aspect of the present invention is a host cell containing a nucleic acid comprising at least 10 consecutive nucleotides of the sequence of SEQ ID NO: 3 or the sequence complementary thereto.

Another embodiment of the present invention is a method of identifying molecules which specifically bind to the protein of SEQ ID NO:4 or a portion thereof comprising the steps of obtaining one or more test molecules to be evaluated for the ability to bind the protein of SEQ ID NO:4, contacting said one or more test molecules with the protein of SEQ ID NO:4 or a portion thereof, removing non-specifically bound test molecules, and retrieving specifically bound test molecules. In one aspect of this embodiment, the one or more test molecules comprise a pool of polypeptides. In another aspect of this embodiment, the one or more test molecules comprise a pool of organic molecules.

Another embodiment of the present invention comprises a method of identifying molecules which specifically bind to the protein of SEQ ID NO:4 or a portion thereof comprising the steps of introducing a nucleic a nucleic acid encoding the protein of SEQ ID NO:4 or a portion thereof into a cell such that the protein of SEQ ID NO:4 or a portion thereof contacts proteins expressed in the cell and identifying those proteins expressed in the cell which specifically interact with the protein of SEQ ID NO:4 or a portion thereof.

Another embodiment of the present invention is A method of identifying molecules which specifically bind to the protein of SEQ ID NO:4 or a portion thereof. One step of the method comprises linking a first nucleic acid encoding the protein of SEQ ID NO:4 or a portion thereof to a first indicator nucleic acid encoding a first indicator polypeptide to generate a first chimeric nucleic acid encoding a first fusion protein. The first fusion protein comprises the protein of SEQ ID NO:4 or a portion thereof and the first indicator polypeptide. Another step of the method comprises linking a second nucleic acid nucleic acid encoding a test polypeptide to a second indicator nucleic acid encoding a second indicator polypeptide to generate a second chimeric nucleic acid encoding a second fusion protein. The second fusion protein comprises the test polypeptide and the second indicator polypeptide. Association between the first indicator protein and the second indicator protein produces a detectable result. Another step of the method comprises introducing the first chimeric nucleic acid and the second chimeric nucleic acid into a cell. Another step comprises detecting the detectable result.

BRIEF DESCRIPTION OF THE DRAWINGS

FIG. 4 shows the results of a haplotype analysis.

FIG. 6A lists bi-allelic markers used in the haplotype analysis.

FIG. 6B lists additional bi-allelic markers in linkage disequilibrium with the PG1 gene.

FIG. 7 lists the positions of exons, splice sites, a stop codon, and a poly A site in the PG1 gene.

FIG. 9 lists homologies between the PG1 protein and known proteins.

DETAILED DESCRIPTION OF THE PREFERRED EMBODIMENT

Figure 1:
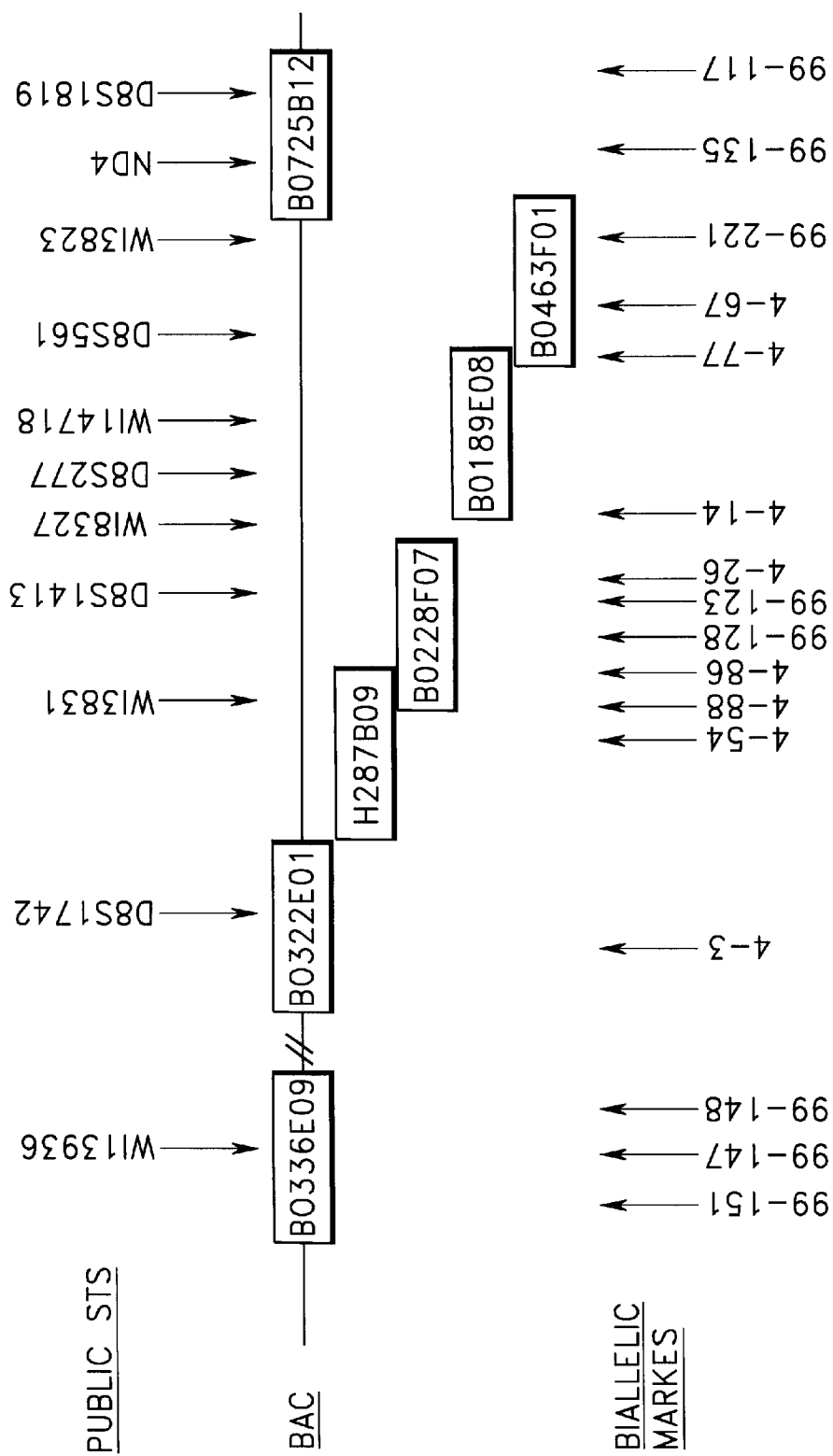
FIG. 1 shows the BAC contig containing the PG1 gene and the positions of bi-allelic markers along the contig.

The incidence of prostate cancer has dramatically increased over the last decades. It averages $30-50/100,000$ males both in Western European countries as well as within the US White male population. In these countries, it has recently become the most commonly diagnosed malignancy, being one of every four cancers diagnosed in American males. Prostate cancer's incidence is very much population specific, since it varies from $2/100,000$ in China, to over $80/100,000$ among African-American males.

In France, the incidence of prostate cancer is $35/100,000$ males and it is increasing by $10/100,000$ per decade. Mortality due to prostate cancer is also growing accordingly. It is the second cause of cancer death among French males, and the first one among French males aged over 70. This makes prostate cancer a serious burden in terms of public health, especially in view of the aging of populations.

An average 40% reduction in life expectancy affects males with prostate cancer. If completely localized, prostate cancer can be cured by surgery, with however an average success rate of only ca. 50%. If diagnosed after metastasis from the prostate, prostate cancer is a fatal disease for which there is no curative treatment.

Early-stage diagnosis relies on Prostate Specific Antigen (PSA) dosage, and would allow the detection of prostate cancer seven years before clinical symptoms become apparent. The effectiveness of PSA dosage diagnosis is however limited, due to its inability to discriminate between malignant and non-malignant affections of the organ.

Therefore, there is a strong need for both a reliable diagnostic procedure which would enable early-stage prostate cancer prognosis, and for preventive and curative treatments of the disease. The present invention relates to the PG1 gene, a gene associated with prostate cancer, as well as diagnostic methods and reagents for detecting alleles of the gene which may cause prostate cancer, and therapies for treating prostate cancer.

I. THE 8p23 REGION

LOH Studies: Implication of 8p23 Region in Distinct Cancer Types

Substantial amounts of LOH data support the hypothesis that genes associated with distinct cancer types are located within 8p23 region of the human genome. Emi, et al., demonstrated the implication of 8p23.1-8p21.3 region in cases of hepatocellular carcinoma, colorectal cancer, and non-small cell lung cancer. (Emi M, Fujiwara Y, Nakajima T, Tsuchiya E, Tsuda H, Hirohashi S, Maeda Y, Tsuruta K, Miyaki M, Nakamura Y, Cancer Res. Oct. 1, 1992; 52(19): 5368–5372) Yaremko, et al., showed the existence of two major regions of LOH for chromosome 8 markers in a sample of 87 colorectal carcinomas. The most prominent loss was found for 8p23.1-pter, where 45% of informative cases demonstrated loss of alleles. (Yaremko M L, Wasylyshyn M L, Paulus K L, Michelassi F, Westbrook C A, Genes Chromosomes Cancer 1994 May; 10(1): 1–6). Scholnick et al. demonstrated the existence of three distinct regions of LOH for the markers of chromosome 8 in cases of squamous cell carcinoma of the supraglottic larynx. They showed that the allelic loss of 8p23 marker D8S264 serves as a statistically significant, independent predictor of poor prognosis for patients with supraglottic squamous cell carcinoma. (Scholnick S B, Haughey B H, Sunwoo J B, el-Mofty S K, Baty J D, Piccirillo J F, Zequeira M R, J. Natl. Cancer Inst. Nov. 20, 1996; 88(22): 1676–1682 and Sunwoo J B, Holt M S, Radford D M, Deeker C, Scholnick S, Genes Chromosomes Cancer 1996 July; 16(3): 164–169).

In other studies, Nagai et al. demonstrated the highest loss of heterozygosity in the specific region of 8p23 by genome wide scanning of LOH in 120 cases of hepatocellular carcinoma (HCC). (Nagai H, Pineau P, Tiollais P, Buendia M A, Dejean A, Oncogene Jun. 19, 1997; 14(24): 2927–2933). Gronwald et al. demonstrated 8p23-pter loss in renal clear cell carcinomas. (Gronwald J, Storkel S, Holtgreve-Grez H, Hadaczek P, Brinkschmidt C, Jauch A, Lubinski J, Cremer, Cancer Res. Feb. 1, 1997; 57(3): 481–487).

The same region is involved in specific cases of prostate cancer. Matsuyama et al. showed the specific deletion of the 8p23 band in prostate cancer cases, as monitored by FISH with D8S7 probe. (Matsuyama H, Pan Y, Skoog L, Tribukait B, Naito K, Ekman P, Lichter P, Bergerheim U S Oncogene 1994 October; 9(10): 3071–3076). They were able to document a substantial number of cases with deletions of 8p23 but retention of the 8p22 marker LPL. Moreover, Ichikawa et al. deduced the existence of a prostate cancer metastasis suppressor gene and localized it to 8p23-q12 by studies of metastasis suppression in highly metastatic rat prostate cells after transfer of human chromosomes. (Ichikawa T, Nihei N, Kuramochi H, Kawana Y, Killary A M, Rinker-Schaeffer C W, Barrett J C, Isaacs J T, Kugoh H, Oshimura M, Shimazaki J, Prostate Suppl. 1996; 6: 31–35).

Recently Washbum et al. were able to find substantial numbers of tumors with the allelic loss specific to 8p23 by LOH studies of 31 cases of human prostate cancer. (Washburn J, Woino K, and Macoska J, Proceedings of American Association for Cancer Research, March 1997; 38). In these samples they were able to define the minimal overlapping region with deletions covering genetic interval D8S262–D8S277.

Linkage Analysis Studies: Search for Prostate Cancer Linked Regions on Chromosome 8

Microsatellite markers mapping to chromosome 8 were used by the inventors to perform linkage analysis studies on 194 individuals issued from 47 families affected with prostate cancer. While multiple point analysis led to weak linkage results, two point lod score analysis led to non significant results, as shown below.

Two point lod (parametric analysis)

| MARKER | Distance (cM) | Z(lod) scores |
|---|---|---|
| D8S1742 |  | −0.13 |
| D8S561 | 0.8 | −0.07 |

| | |
|---|---|
| # of families analyzed | 47 |
| Total # of individuals genotyped | 194 |
| Total # of affected individuals genotyped | 122 |

In view of the non-significant results obtained with linkage analysis, a new mapping approach based on linkage disequilibrium of bi-allelic markers was utilized to identify genes responsible for sporadic cases of prostate cancer.

II. LINKAGE DISEQUILIBRIUM USING BI-ALLELIC MARKERS TO IDENTIFY CANDIDATE LOCI RESPONSIBLE FOR DISEASE

Linkage Disequilibrium

Once a chromosomal region has been identified as potentially harboring a candidate gene associated with a sporadic trait, an excellent approach to refine the candidate gene's location within the identified region is to look for statistical associations between the trait and some marker genotype when comparing an affected (trait$^+$) and a control (trait$^-$) population.

Association studies have most usually relied on the use of bi-allelic markers. Bi-allelic markers are genome-derived polynucleotides that exhibit bi-allelic polymorphism at one single base position. By definition, the lowest allele frequency of a bi-allelic polymorphism is 1%; sequence variants that show allele frequencies below 1% are called rare mutations. There are potentially more than $10^7$ bi-allelic markers lying along the human genome. However, a bi-allelic marker will show a sufficient degree of informativeness for genetic mapping only provided the frequency of its less frequent allele is not less than about 0.3, i.e., its heterozygosity rate is higher than about 0.42 (the heterozygosity rate for a bi-allelic marker is $2 P_a (1-P_a)$, where $P_a$ is the frequency of allele a).

Association studies seek to establish correlations between traits and genetic markers and are based on the phenomenon of linkage disequilibrium (LD). LD is defined as the trend for alleles at nearby loci on haploid genomes to correlate in the population. If two genetic loci lie on the same chromosome, then sets of alleles on the same chromosomal segment (i.e., haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium.

Since results generated by association studies are essentially based on the quantitative calculation of allele frequencies, they best apply to the analysis of germline mutations. This is mainly due to the fact that allelic frequencies are difficult to quantify within tumor tissue samples because of the usual presence of normal cells within the studied tumor samples. Association studies applied to cancer genetics will therefore be best suited to the identification of tumor suppressor genes.

Trait localization by Linkage Disequilibrium Mapping

Any gene responsible or partly responsible for a given trait will be in LD with some flanking markers. To map such a gene, specific alleles of these flanking markers which are associated with the gene or genes responsible for the trait are identified. Although the following discussion of techniques for finding the gene or genes associated with a particular trait using linkage disequilibrium mapping, refers to locating a single gene which is responsible for the trait, it will be appreciated that the same techniques may also be used to identify genes which are partially responsible for the trait.

Association studies may be conducted within the general population (as opposed to the linkage analysis techniques discussed above which are limited to studies performed on related individuals in one or several affected families).

Association between a bi-allelic marker A and a trait T may primarily occur as a result of three possible relationships between the bi-allelic marker and the trait. First, allele a of bi-allelic marker A may be directly responsible for trait T (e.g., Apo E e4 allele and Alzheimer's disease). However, since the majority of the bi-allelic markers used in genetic mapping studies are selected randomly, they mainly map outside of genes. Thus, the likelihood of allele a being a functional mutation directly related to trait T is therefore very low.

An association between a bi-allelic marker A and a trait T may also occur when the bi-allelic marker is very closely linked to the trait locus. In other words, an association occurs when allele a is in linkage disequilibrium with the trait-causing allele. When the bi-allelic marker is in close proximity to a gene responsible for the trait, more extensive genetic mapping will ultimately allow a gene to be discovered near the marker locus which carries mutations in people with trait T (i.e. the gene responsible for the trait or one of the genes responsible for the trait). As will be further exemplified below using a group of bi-allelic markers which are in close proximity to the gene responsible for the trait, the location of the causal gene can be deduced from the profile of the association curve between the bi-allelic markers and the trait. The causal gene will be found in the vicinity of the marker showing the highest association with the trait.

Finally, an association between a bi-allelic marker and a trait may occur when people with the trait and people without the trait correspond to genetically different subsets of the population who, coincidentally, also differ in the frequency of allele a (population stratification). This phenomenon may be avoided by using large heterogeneous samples.

Association studies are particularly suited to the efficient identification of susceptibility genes that present common polymorphisms, and are involved in multifactorial traits whose frequency is relatively higher than that of diseases with monofactorial inheritance.

Application of Linkage Disequilibrium Mapping to Candidate Gene Identification

The general strategy of association studies using a set of bi-allelic markers, is to scan two pools of individuals (affected individuals and unaffected controls) characterized by a well defined phenotype in order to measure the allele frequencies for a number of the chosen markers in each of these pools. If a positive association with a trait is identified using an array of bi-allelic markers having a high enough density, the causal gene will be physically located in the vicinity of the associated markers, since the markers showing positive association to the trait are in linkage disequilibrium with the trait locus. Regions harboring a gene responsible for a particular trait which are identified through association studies using high density sets of bi-allelic markers will, on average, be 20–40 times shorter in length than those identified by linkage analysis.

Once a positive association is confirmed as described above, BACs (bacterial artificial chromosomes) obtained from human genomic libraries, constructed as described below, harboring the markers identified in the association analysis are completely sequenced.

Once a candidate region has been sequenced and analyzed, the functional sequences within the candidate region (exons and promoters, and other potential regulatory regions) are scanned for mutations which are responsible for the trait by comparing the sequences of a selected number of controls and affected individuals using appropriate software. Candidate mutations are further confirmed by screening a larger number of affected individuals and controls using the microsequencing techniques described below.

Candidate mutations are identified as follows. A pair of oligonucleotide primers is designed in order to amplify the sequences of every predicted functional region. PCR amplification of each predicted functional sequence is carried out on genomic DNA samples from affected patients and unaffected controls. Amplification products from genomic PCR are subjected to automated dideoxy terminator sequencing reactions and electrophoresed on ABI 377 sequencers. Following gel image analysis and DNA sequence extraction, the sequence data are automatically analyzed to detect the presence of sequence variations among affected cases and unaffected controls. Sequences are systematically verified by comparing the sequences of both DNA strands of each individual.

Polymorphisms are then verified by screening a larger population of affected individuals and controls using the microsequencing technique described below in an individual test format. Polymorphisms are considered as candidate mutations when present in affected individuals and controls at frequencies compatible with the expected association results.

Association Studies: Statistical Analysis and Haplotyping

As mentioned above, linkage analysis typically localizes a disease gene to a chromosomal region of several megabases. Further refinement in location requires the analysis of additional families in order to increase the number of recombinants. However, this approach becomes unfeasible because recombination is rarely observed even within large pedigrees (Boehnke, M, 1994, Am. J. Hum. Genet. 55: 379–390).

Linkage disequilibrium, the nonrandom association of alleles at linked loci, may offer an alternative method of obtaining additional recombinants. When a chromosome carrying a mutant allele of a gene responsible for a given trait is first introduced into a population as a result of either mutation or migration, the mutant allele necessarily resides on a chromosome having a unique set of linked markers (haplotype). Consequently, there is complete disequilibrium between these markers and the disease mutation: the disease mutation is present only linked to a specific set of marker alleles. Through subsequent generations, recombinations occur between the disease mutation and these marker polymorphisms, resulting in a gradual disappearance of disequilibrium. The degree of disequilibrium dissipation depends on the recombination frequency, so the markers closest to the disease gene will tend to show higher levels of disequilibrium than those that are farther away (Jorde L B, 1995, Am. J. Hum. Genet. 56: 11–14). Because linkage disequilibrium patterns in a present-day population reflect the action of recombination through many past generations, disequilibrium analysis effectively increases the sample of recombinants. Thus the mapping resolution achieved through the analysis of linkage disequilibrium patterns is much higher than that of linkage analysis.

In practice, in order to define the regions bearing a candidate gene, the affected and control populations are genotyped using an appropriate number of bi-allelic markers (at a density of 1 marker every 50–150 kilobases). Then, a marker/trait association study is performed that compares the genotype frequency of each bi-allelic marker in the affected and control populations by means of a chi square statistical test (one degree of freedom).

After the first screening, additional markers within the region showing positive association are genotyped in the affected and control populations. Two types of complementary analysis are then performed. First, a marker/trait association study (as described above) is performed to refine the location of the gene responsible for the trait. In addition, a haplotype association analysis is performed to define the frequency and the type of the ancestral/preferential carrier haplotype. Haplotype analysis, by combining the informativeness of a set of bi-allelic markers increases the power of the association analysis, allowing false positive and/or negative data that may result from the single marker studies to be eliminated.

The haplotype analysis is performed by estimating the frequencies of all possible haplotypes for a given set of bi-allelic markers in the case and control populations, and comparing these frequencies by means of a chi square statistical test (one degree of freedom). Haplotype estimations are performed by applying the Expectation-Maximization (EM) algorithm (Excoffier L & Slatkin M, 1995, Mol. Biol. Evol. 12: 921–927), using the EM-HAPLO program (Hawley M E, Pakstis A J & Kidd K K, 1994, Am. J. Phys. Anthropol. 18: 104). The EM algorithm is used to estimate haplotype frequencies in the case when only genotype data from unrelated individuals are available. The EM algorithm is a generalized iterative maximum likelihood approach to estimation that is useful when data are ambiguous and/or incomplete.

The application of bi-allelic marker based linkage disequilibrium analysis to the 8p23 region to identify a gene associated with prostate cancer is described below.

III. APPLICATION OF LINKAGE DISEQUILIBRIUM MAPPING TO THE 8p23 REGION

YAC Contig Construction in 8p23 Region

First, a YAC contig which contains the 8p23 region was constructed as follows. The CEPH-Genethon YAC map for the entire human genome (Chumakov I. M. et al. A YAC contig map of the human genome, Nature, 377 Supp.: 175–297, 1995) was used for detailed contig building in the region around D8S262 and D8S277 genetic markers. Screening data available for regional genetic markers D8S1706, D8S277, D8S1742, D8S518, D8S262, D8S1798, D8S1140, D8S561 and D8S1819 were used to select the following set of CEPH YACs, localized within this region: 832_g_12, 787_c_11, 920_h_7, 807_a_1, 842_b_1, 745_a_3, 910_d_3, 879_f_11, 918_c_6, 764_c_7, 910_f_12, 967_c_11, 856_d_8, 792_a_6, 812_h_4, 873_c_8, 930_a_2, 807_a_1, 852_d_10. This set of YACs was tested by PCR with the above mentioned genetic markers as well as with other publicly available markers supposedly located within the 8p23 region. As a result of these studies, a YAC STS contig map was generated around genetic markers D8S262 and D8S277. The two CEPH YACs, 920_h_7 (1170 kb insert size) and 910_f_12 (1480 kb insert size) constitute a minimal tiling path in this region, with an estimated size of ca. 2 Megabases.

During this mapping effort, the following publicly known STS markers were precisely located within the contig: WI-14718, WI-3831, D8S1413E, WI-8327, WI-3823, ND4.

BAC Contig Construction Covering D8S262-D8S277 Fragment Within 8p23 Region of the Human Genome Following construction of the YAC contig, a BAC contig was constructed as follows. BAC libraries were obtained as described in Woo et al. Nucleic Acids Res., 1994, 22, 4922–4931, the disclosure of which is incorporated herein by reference. Briefly, two different whole human genome libraries were produced by cloning BamHI or HindIII partially digested DNA from a lymphoblastoid cell line (derived from individual N°8445, CEPH families) into the pBeloBAC11 vector (Kim et al. Genomics, 1996, 34, 213–218). The library produced with the BamHI partial digestion contained 110,000 clones with an average insert size of 150 kb, which corresponds to 5 human haploid genome equivalents. The library prepared with the HindIII partial digestion corresponds to 3 human genome equivalents with an average insert size of 150 kb.

BAC Screening

The human genomic BAC libraries obtained as described above were screened with all of the above mentioned STSs.

DNA from the clones in both libraries was isolated and pooled in a three dimensional format ready for PCR screening with the above mentioned STSs using high throughput PCR methods (Chumakov et al., Nature 1995, 377: 175–298, the disclosure of which is incorporated herein by reference). Briefly, three dimensional pooling consists in rearranging the samples to be tested in a manner which allows the number of PCR reactions required to screen the clones with STSs to be reduced by at least 100 fold, as compared to screening each clone individually. PCR amplification products were detected by conventional agarose gel electrophoresis combined with automated image capturing and processing.

In a final step, STS-positive clones were checked individually. Subchromosomal localization of BACs was systematically verified by fluorescence in situ hybridization (FISH), performed on metaphasic chromosomes as described by Cherif et al. Proc. Natl. Acad. Sci. USA 1990, 87: 6639–6643, the disclosure of which is incorporated herein by reference.

BAC insert size was determined by Pulsed Field Gel Electrophoresis after digestion with restriction enzyme NotI.

BAC Contigation

The ordered BACs selected by STS screening and verified by FISH, were assembled into contigs and new markers were generated by partial sequencing of insert ends from some of them. These markers were used to fill the gaps in the contig of BAC clones covering the chromosomal region around D8S277, having an estimated size of 2 megabases. Selected BAC clones from the contig were subcloned and sequenced.

BAC Subcloning

Each BAC human DNA was first extracted using the alkaline lysis procedure and then sheared by sonication. The obtained DNA fragments were end-repaired and electrophoresed on preparative agarose gels. The fragments in the desired size range were isolated from the gel, purified and ligated to a linearized, dephosphorylated, blunt-ended plasmid cloning vector (pBluescript II Sk (+)). Example 1 describes the BAC subcloning procedure.

EXAMPLE 1

The cells obtained from three liters overnight culture of each BAC clone were treated by alkaline lysis using conventional techniques to obtain the BAC DNA containing the genomic DNA inserts. After centrifugation of the BAC DNA in a cesium chloride gradient, ca. 50 µg of BAC DNA was purified. 5–10 µg of BAC DNA was sonicated using three distinct conditions, to obtain fragments of the desired size. The fragments were treated in a 50 µl volume with two units of Vent polymerase for 20 min at 70° C., in the presence of the four deoxytriphosphates (100 µM). The resulting blunt-ended fragments were separated by electrophoresis on low-melting point 1% agarose gels (60 Volts for 3 hours). The fragments were excised from the gel and treated with agarase. After chloroform extraction and dialysis on Microcon 100 columns, DNA in solution was adjusted to a 100 ng/µl concentration. A ligation was performed overnight by adding 100 ng of BAC fragmented DNA to 20 ng of pBluescript II Sk (+) vector DNA linearized by enzymatic digestion, and treated by alkaline phosphatase. The ligation reaction was performed in a 10 µl final volume in the presence of 40 units/µl T4 DNA ligase (Epicentre). The ligated products were electroporated into the appropriate cells (ElectroMAX *E.coli* DH10B cells). IPTG and X-gal were added to the cell mixture, which was then spread on the surface of an ampicillin-containing agar plate. After overnight incubation at 37° C., recombinant (white) colonies were randomly picked and arrayed in 96 well microplates for storage and sequencing.

Partial Sequencing of BACs

At least 30 of the obtained BAC clones were sequenced by the end pairwise method (500 bp sequence from each end) using a dye-primer cycle sequencing procedure. Pairwise sequencing was performed until a map allowing the relative positioning of selected markers along the corresponding DNA region was established. Example 2 describes the sequencing and ordering of the BAC inserts.

EXAMPLE 2

The subclone inserts were amplified by PCR on overnight bacterial cultures, using vector primers flanking the insertions. The insert extremity sequences (on average 500 bases at each end) were determined by fluorescent automated sequencing on ABI 377 sequencers, with a ABI Prism DNA Sequencing Analysis software (2.1.2 version).

The sequence fragments from BAC subclones were assembled using Gap4 software from R. Staden (Bonfield et al. 1995). This software allows the reconstruction of a single sequence from sequence fragments. The sequence deduced from the alignment of different fragments is called the consensus sequence. We used directed sequencing techniques (primer walking) to complete sequences and link contigs.

FIG. 1 shows the overlapping BAC subclones (labeled BAC) which make up the assembled contig and the positions of the publicly known STS markers along the contig.

Identification of Bi-allelic Markers Lying Along the BAC Contig

Following assembly of the BAC contig, bi-allelic markers lying along the contig were then identified. Given that the assessed distribution of informative bi-allelic markers in the human genome (bi-allelic polymorphisms with a heterozygosity rate higher than 42%) is one in 2.5 to 3 kb, six 500 bp genomic fragments have to be screened in order to identify 1 bi-allelic marker. Six pairs of primers per potential marker, each one defining a ca. 500 bp amplification fragment, were derived from the above mentioned BAC partial sequences. All primers contained a common upstream oligonucleotide tail enabling the easy systematic sequencing of the resulting amplification fragments. Amplification of each BAC-derived sequence was carried out on pools of DNA from ca. 100 individuals. The conditions used for the polymerase chain reaction were optimized so as to obtain more than 95% of PCR products giving 500 bp-sequence reads.

The amplification products from genomic PCR using the oligonucleotides derived from the BAC subclones were subjected to automated dideoxy terminator sequencing reactions using a dye-primer cycle sequencing protocol. Following gel image analysis and DNA sequence extraction, sequence data were automatically processed with appropriate software to assess sequence quality and to detect the presence of bi-allelic sites among the pooled amplified fragments. Bi-allelic sites were systematically verified by comparing the sequences of both strands of each pool.

The detection limit for the frequency of bi-allelic polymorphisms detected by sequencing pools of 100 individuals is 0.3±0.05 for the minor allele, as verified by sequencing pools of known allelic frequencies. Thus, the bi-allelic markers selected by this method will be "informative bi-allelic markers" since they have a frequency of 0.3 to 0.5 for the minor allele and 0.5 to 0.7 for the major allele, therefore an average heterozygosity rate higher than 42%.

Example 3 describes the preparation of genomic DNA samples from the individuals screened to identify bi-allelic markers.

EXAMPLE 3

The population used in order to generate bi-allelic markers in the region of interest consisted of ca. 100 unrelated individuals corresponding to a French heterogeneous population.

DNA was extracted from peripheral venous blood of each donor as follows.

30 ml of blood were taken in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0.4 M

200 μl SDS 10%

500 μl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 μg/ml DNA).

To determine the presence of proteins in the DNA solution, the OD 260/OD 280 ratio was determined. Only DNA preparations having a OD 260/OD 280 ratio between 1.8 and 2 were used in the subsequent steps described below.

DNA Amplification

Once each BAC was isolated, pairs of primers, each one defining a 500 bp-amplification fragment, were designed. Each of the primers contained a common oligonucleotide tail upstream of the specific bases targeted for amplification, allowing the amplification products from each set of primers to be sequenced using the common sequence as a sequencing primer. The primers used for the genomic amplification of sequences derived from BACs were defined with the OSP software (Hillier L. and Green P. Methods Appl., 1991, 1: 124–8). The synthesis of primers was performed following the phosphoramidite method, on a GENSET UFPS 24.1 synthesizer.

Example 4 provides the procedures used in the amplification reactions.

EXAMPLE 4

The amplification of each sequence was performed by PCR (Polymerase Chain Reaction) as follows:

| | |
|---|---|
| final volume | 50 μl |
| genomic DNA | 100 ng |
| $MgCl_2$ | 2 mM |
| dNTP (each) | 200 μM |
| primer (each) | 7.5 pmoles |
| Ampli Taq Gold DNA polymerase (Perkin) | 1 unit |
| PCR buffer (10X = 0.1M Tris HCl pH 8.3, 0.5M KCl) | 1X. |

The amplification was performed on a Perkin Elmer 9600 Thermocycler or MJ Research PTC200 with heating lid. After heating at 94° C. for 10 minutes, 35 cycles were performed. Each cycle comprised: 30 sec at 94° C., 1 minute at 55° C., and 30 sec at 72° C. For final elongation, 7 minutes at 72° C. ended the amplification.

The obtained quantity of amplification products was determined on 96-well microtiter plates, using a fluorimeter and Picogreen as intercalating agent (Molecular Probes).

The sequences of the amplification products were determined for each of the approximately 100 individuals from whom genomic DNA was obtained. Those amplification products which contained bi-allelic markers were identified.

FIG. 1 shows the locations of the bi-allelic markers along the 8p23 BAC contig. This first set of markers corresponds to a medium density map of the candidate locus, with an inter-marker distance averaging 50 kb–150 kb.

A second set of bi-allelic markers was then generated as described above in order to provide a very high-density map of the region identified using the first set of markers which can be used to conduct association studies, as explained below. The high density map has markers spaced on average every 2–50 kb.

The bi-allelic markers were then used in association studies as described below.

Collection of DNA Samples from Affected and Non-affected Individuals

Prostate cancer patients were recruited according to clinical inclusion criteria based on pathological or radical prostatectomy records. Control cases included in this study were both ethnically- and age-matched to the affected cases; they were checked for both the absence of all clinical and biological criteria defining the presence or the risk of prostate cancer, and for the absence of related familial prostate cancer cases. Both affected and control individuals corresponded to unrelated cases.

The two following pools of independent individuals were used in the association studies. The first pool, comprising individuals suffering from prostate cancer, contained 185 individuals. Of these 185 cases of prostate cancer, 45 cases were sporadic and 140 cases were familial. The second pool, the control pool, contained 104 non-diseased individuals.

Haplotype analysis was conducted using additional diseased (total samples: 281) and control samples (total samples: 130), from individuals recruited according to similar criteria.

Genotyping Affected and Control Individuals

The general strategy to perform the association studies was to individually scan the DNA samples from all individuals in each of the two populations described above in order to establish the allele frequencies of the above described bi-allelic markers in each of these populations.

Allelic frequencies of the above-described bi-allelic markers in each population were determined by performing microsequencing reactions on amplified fragments obtained by genomic PCR performed on the DNA samples from each individual.

DNA samples and amplification products from genomic PCR were obtained in similar conditions as those described above for the generation of bi-allelic markers, and subjected to automated microsequencing reactions using fluorescent ddNTPs (specific fluorescence for each ddNTP) and the appropriate oligonucleotide microsequencing primers which hybridized just upstream of the polymorphic base. Once specifically extended at the 3' end by a DNA polymerase using the complementary fluorescent dideoxynucleotide analog (thermal cycling), the primer was precipitated to remove the unincorporated fluorescent ddNTPs. The reaction products were analyzed by electrophoresis on ABI 377 sequencing machines.

Example 5 describes the microsequencing procedures.

EXAMPLE 5

5 µl of PCR products in a microtiter plate were added to 5 µl purification mix [2U SAP (Amersham); 2U Exonuclease I (Amersham); 1 µl SAP10×buffer: 400 mM Tris-HCl pH8, 100 mM MgCl2; H2O final volume 5 µl]. The reaction mixture was incubated 30 minutes at 37° C., and denatured 10 minutes at 94° C. After 10 sec centrifugation, the microsequencing reaction was performed on line with the whole purified reaction mixture (10 µl) in the microplate using 10 pmol microsequencing oligonucleotide (23 mers, GENSET, crude synthesis, 5 OD), 0.5 U Thermosequenase (Amersham), 1.25 µl Thermosequenase 16×buffer (Amersham), both of the fluorescent ddNTPs (Perkin Elmer) corresponding to the polymorphism [0.025 µl ddTTP and ddCTP, 0.05 µl ddATP and ddGTP], H2O to a final volume of 20 µl. A PCR program on a GeneAmp 9600 thermocycler was carried out as follows: 4 minutes at 94° C.; 5 sec at 55° C./10 sec at 94° C. for 20 cycles. The reaction product was incubated at 4° C. until precipitation. The microtiter plate was centrifuged 10 sec at 1500 rpm. 19 µl MgCl2 2 mM and 55 µl 100% ethanol were added in each well. After 15 minute incubation at room temperature, the microtiter plate was centrifuged at 3300 rpm 15 minutes at 4° C. Supernatants were discarded by inverting the microtitre plate on a box folded to proper size and by centrifugation at 300 rpm 2 minutes at 4° C. afterwards. The microplate was then dried 5 minutes in a vacuum drier. The pellets were resuspended in 2.5 µl formamide EDTA loading buffer (0.7 µl of 9 µg/µl dextran blue in 25 mM EDTA and 1.8 µl formamide). A 10% polyacrylamide gel/12 cm/64 wells was pre-run for 5 minutes on a 377 ABI 377 sequencer. After 5 minutes denaturation at 100° C., 0.8 µl of each microsequencing reaction product was loaded in each well of the gel. After migration (2 h 30 for 2 microtiter plates of PCR products per gel), the fluorescent signals emitted by the incorporated ddNTPs were analysed on the ABI 377 sequencer using the GENESCAN software (Perkin Elmer). Following gel analysis, data were automatically processed with a software that allowed the determination of the alleles of bi-allelic markers present in each amplified fragment.

Association Studies

Figure 2:
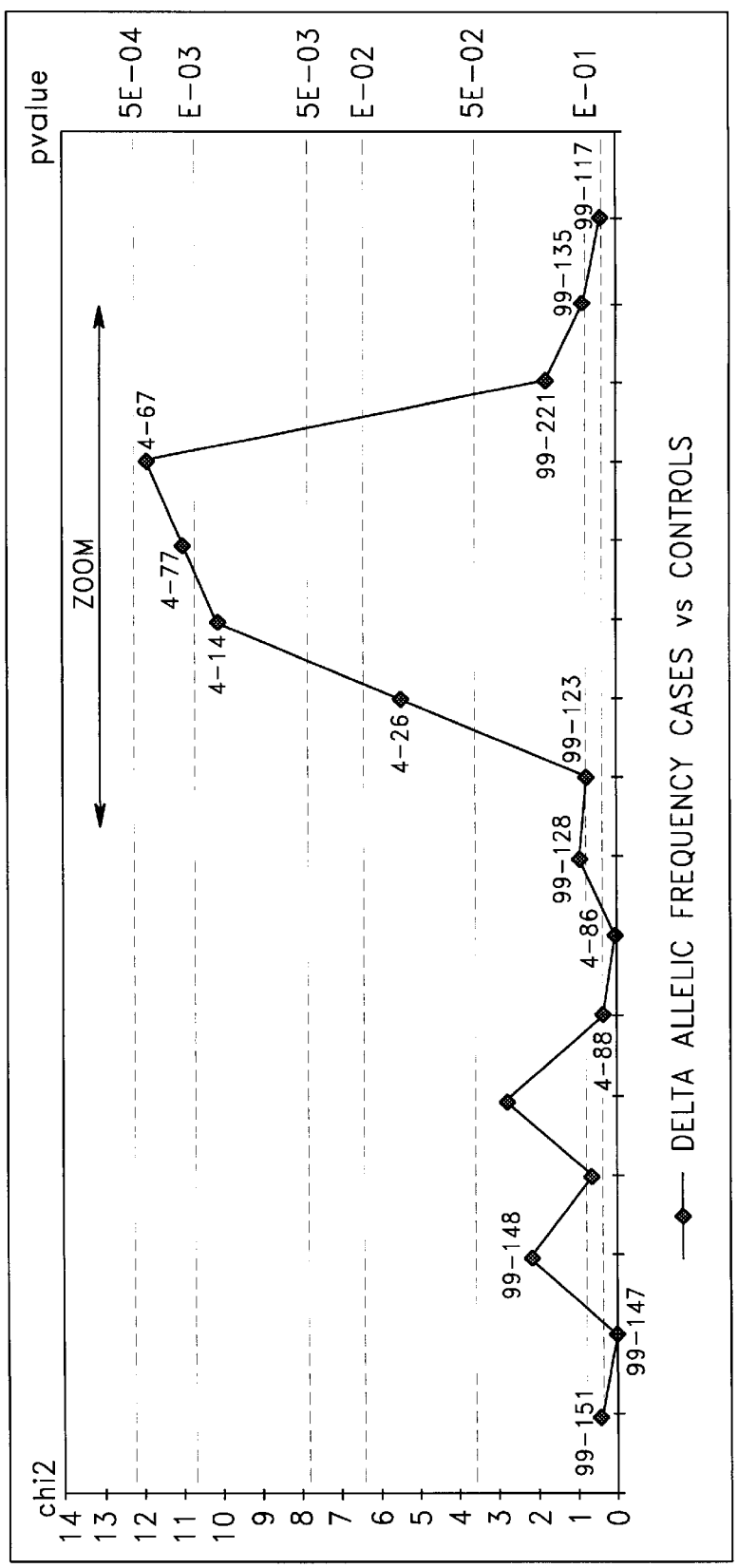
FIG. 2 shows the results of the first screening of an association study.

Association studies were run in two successive steps. In a first step, a rough localization of the candidate gene was achieved by determining the frequencies of the bi-allelic markers of FIG. 1 in the affected and unaffected populations. The results of this rough localization are shown in FIG. 2. This analysis indicated that a gene responsible for prostate cancer was located near the bi-allelic marker designated 4-67.

In a second phase of the analysis, the position of the gene responsible for prostate cancer was further refined using the very high density set of markers described above. The results of this localization are shown in FIG. 3.

Figure 3:
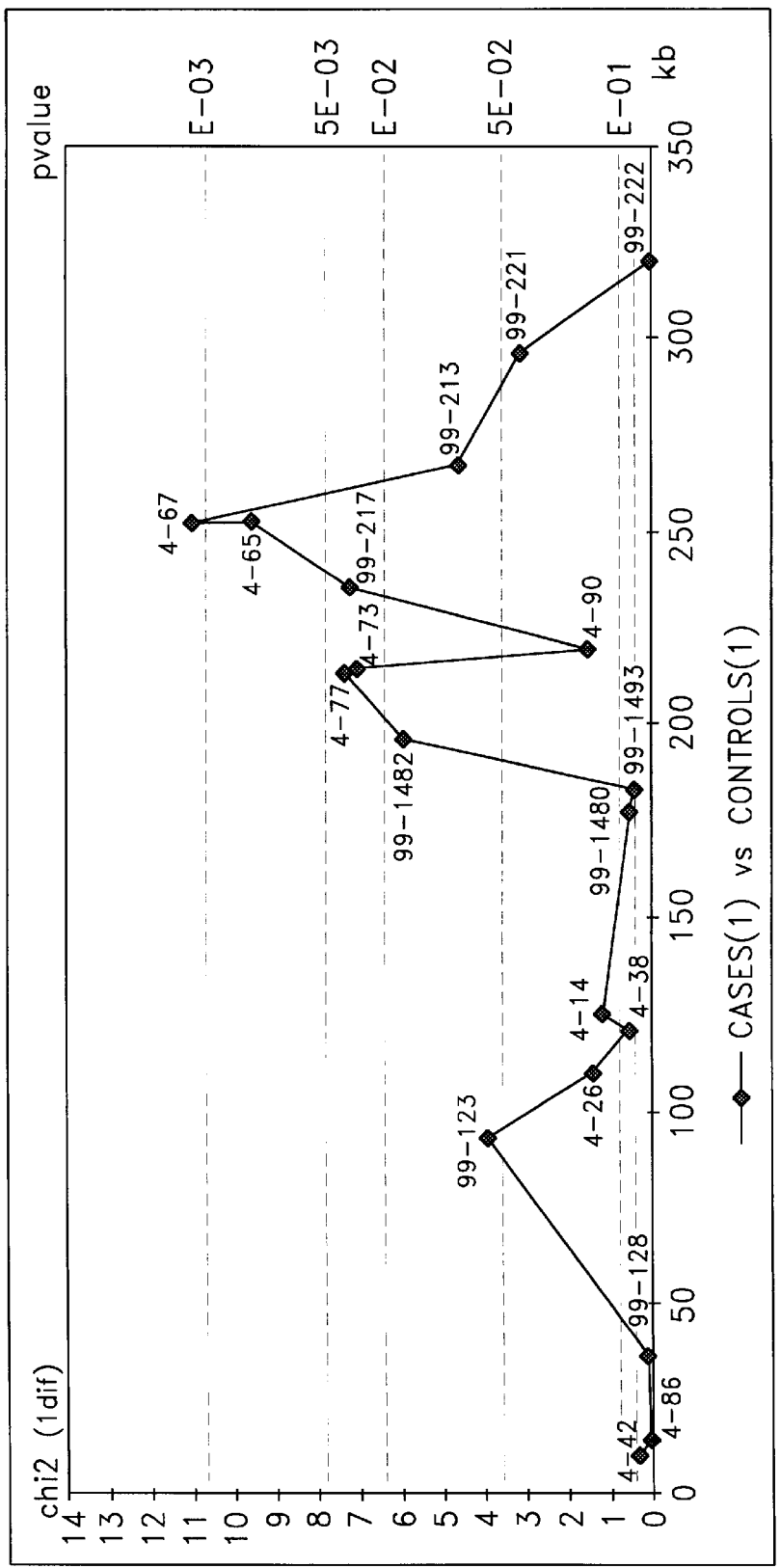
FIG. 3 shows a zoom of the association study.

As shown in FIG. 3, the second phase of the analysis confirmed that the gene responsible for prostate cancer was near the bi-allelic marker designated 4-67, most probably within a ca. 150 kb region comprising the marker.

Haplotype Analysis

The allelic frequencies of each of the alleles of bi-allelic markers 99-123, 4-26, 4-14, 4-77, 99-217, 4-67, 99-213, 99-221, and 99-135 (SEQ ID NOs: 21–38) were determined in the affected and unaffected populations. Table 1 lists the internal identification numbers of the markers used in the haplotype analysis (SEQ ID NOs: 21–38), the alleles of each marker, the most frequent allele in both unaffected individuals and individuals suffering from prostate cancer, the least frequent allele in both unaffected individuals and individuals suffering from prostate cancer, and the frequencies of these alleles in each population.

Among all the theoretical potential different haplotypes based on 2 to 9 markers, 11 haplotypes showing a strong association with prostate cancer were selected. The results of these haplotype analyses are shown in FIG. 4.

FIGS. 2, 3, and 4 aggregate linkage analysis results with sequencing results which permitted the physical order and/or the distance between markers to be estimated.

Figure 5A:
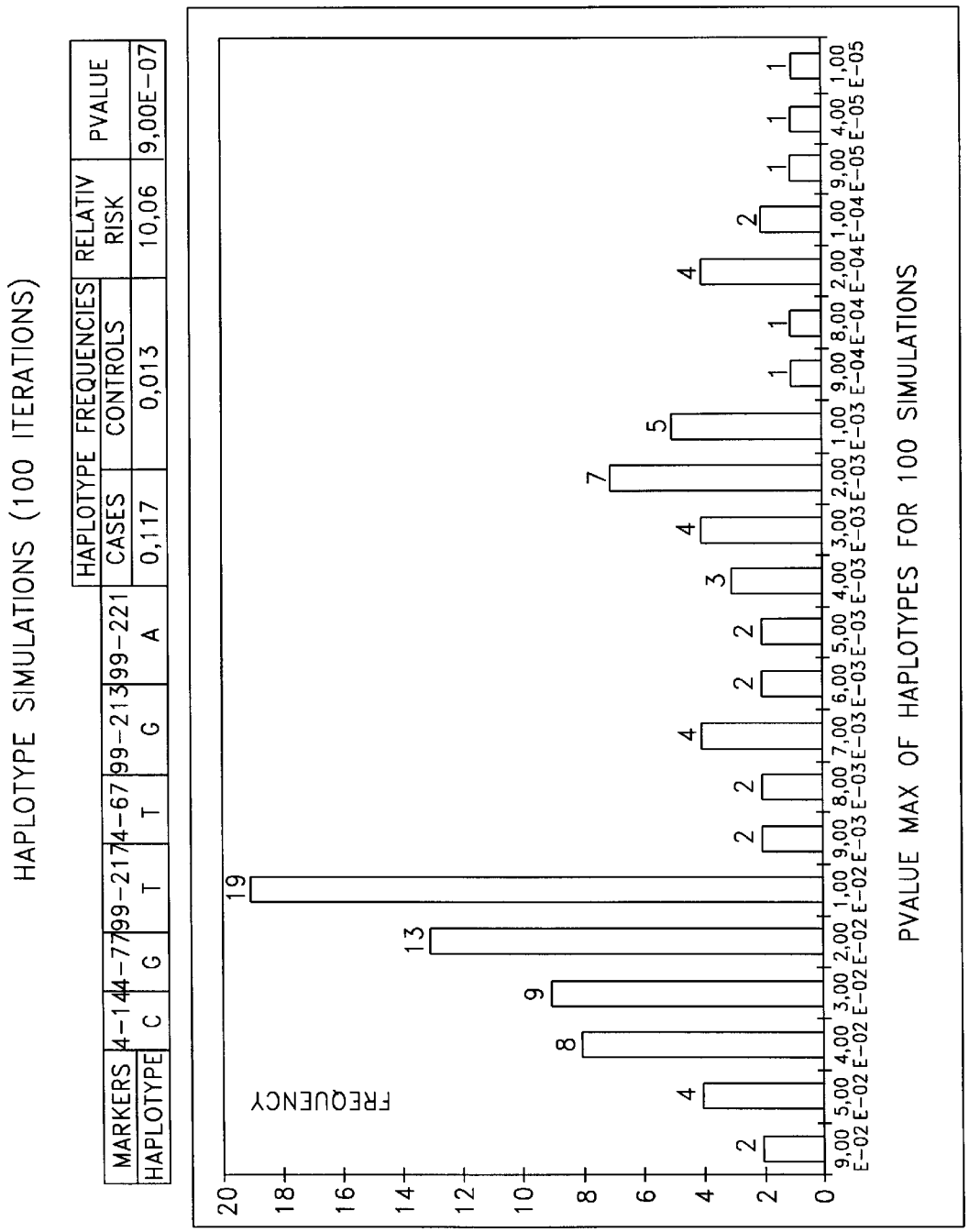
FIG. 5 shows the results of an experiment evaluating the significance of the haplotype analysis of FIG. 4.
Figure 5B:
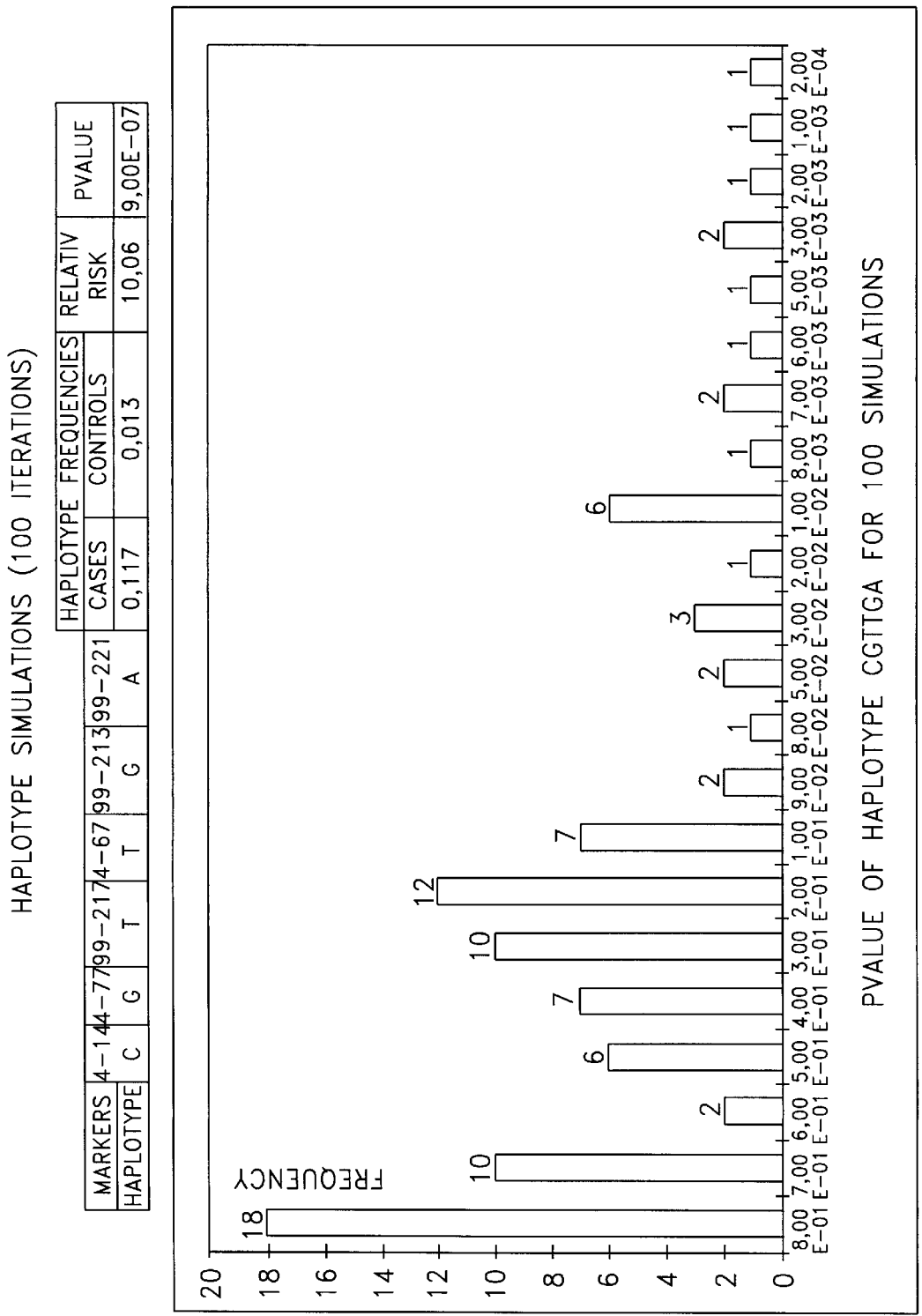

The significance of the values obtained in FIG. 4 are underscored by the following results of computer simulations. For the computer simulations, the data from the affected individuals and the unaffected controls were pooled and randomly allocated to two groups which contained the same number of individuals as the affected and unaffected groups used to compile the data summarized in FIG. 4. A haplotype analysis was run on these artificial groups for the six markers included in haplotype 5 of FIG. 4. This experiment was reiterated 100 times and the results are shown in FIG. 5. Among 100 iterations, only 5% of the obtained haplotypes are present with a p-value below $1 \times 10^{-4}$ as compared to the p-value of $9 \times 10^{-7}$ for haplotype 5 of FIG. 4. Furthermore, for haplotype 5 of FIG. 4, only 6% of the obtained haplotypes have a significance level below $5 \times 10^{-3}$, while none of them show a significance level below $5 \times 10^{-5}$.

Thus, using the data of FIG. 4 and evaluating the associations for single maker alleles or for haplotypes will permit estimation of the risk a corresponding carrier has to develop prostate cancer. Significance thresholds of relative risks will be adapted to the reference sample population used.

The diagnostic techniques may employ a variety of methodologies to determine whether a test subject has a bi-allelic marker pattern associated with an increased risk of developing prostate cancer or suffers from prostate cancer resulting from a mutant PG1 allele. These include any method enabling the analysis of individual chromosomes for haplotyping, such as family studies, single sperm DNA analysis or somatic hybrids.

In each of these methods, a nucleic acid sample is obtained from the test subject and the bi-allelic marker pattern for one or more of the bi-allelic markers listed in FIGS. 4, 6A and 6B is determined. The bi-allelic markers listed in FIG. 6A are those which were used in the haplotype analysis of FIG. 4. The first column of FIG. 6A lists the BAC clones in which the bi-allelic markers lie. The second column of FIG. 6A lists the internal identification number of the marker. The third column of FIG. 6A lists the sequence identification number for a first allele of the bi-allelic markers. The fourth column of FIG. 6A lists the sequence identification number for a second allele of the bi-allelic markers. For example, the first allele of the bi-allelic marker 99-123 has the sequence of SEQ ID NO:21 and the second allele of the bi-allelic marker has the sequence of SEQ ID NO: 30.

The fifth column of FIG. 6A lists the sequences of upstream primers which may be used to generate amplification products containing the polymorphic bases of the bi-allelic markers. The sixth column of FIG. 6A lists the sequence identification numbers for the upstream primers.

The seventh column of FIG. 6A lists the sequences of downstream primers which may be used to generate amplification products containing the polymorphic bases of the bi-allelic markers. The eighth column of FIG. 6A lists the sequence identification numbers for the downstream primers.

The ninth column of FIG. 6A lists the position of the polymorphic base in the amplification products generated using the upstream and downstream primers. The tenth column lists the identities of the polymorphic bases found at the polymorphic positions in the bi-allelic markers. The eleventh and twelfth columns list the locations of microsequencing primers in the bi-allelic markers which can be used to determine the identities of the polymorphic bases.

In addition to the bi-allelic markers of SEQ ID NOs: 21–38, other bi-allelic markers (designated 99-1482, 4-73, 4-65) have been identified which are closely linked to one or more of the bi-allelic markers of SEQ ID NOs: 21–38, SEQ ID NOs: 57–62, and the PG1 gene. These bi-allelic markers include the markers of SEQ ID NOs: 57–62, which are listed in FIG. 6B. The columns in FIG. 6B are identical to the corresponding columns in FIG. 6A. SEQ ID NOs: 58, 59, 61, and 62 lie within the PG1 gene of SEQ ID NO:1 at the positions indicated in the accompanying Sequence Listing.

Genetic analysis of these additional bi-allelic markers may be performed as follows. Nucleic acid samples are obtained from individuals suffering from prostate cancer and unaffected individuals. The frequencies at which each of the two alleles occur in the affected and unaffected populations is determined using the methodologies described above. Association values are calculated to determine the correlation between the presence of a particular allele or spectrum of alleles and prostate cancer. The markers of SEQ ID NOs: 21–38 may also be included in the analysis used to calculate the risk factors. The markers of SEQ ID NOs: 21–38 and SEQ ID NOs: 57–62 may be used in diagnostic techniques, such as those described below, to determine whether an individual is at risk for developing prostate cancer or suffers from prostate cancer as a result of a mutation in the PG1 gene.

Example 6 describes methods for determining the bi-allelic marker pattern.

EXAMPLE 6

A nucleic acid sample is obtained from an individual to be tested for susceptibility to prostate cancer or PG1 mediated prostate cancer. The nucleic acid sample may be an RNA sample or a DNA sample.

A PCR amplification is conducted using primer pairs which generate amplification products containing the polymorphic nucleotides of one or more bi-allelic markers associated with prostate cancer-related forms of PG 1, such as the bi-allelic markers of SEQ ID NOs: 21–38, SEQ ID NOs: 57–62, bi-allelic markers which are in linkage disequilibrium with the bi-allelic markers of SEQ ID NOs: 21–38, SEQ ID NOs: 57–62, bi-allelic markers in linkage disequilibrium with the PG1 gene, or combinations thereof. In some embodiments, the PCR amplication is conducted using primer pairs which generate amplification products containing the polymorphic nucleotides of several bi-allelic markers. For example, in one embodiment, amplification products containing the polymorphic bases of several bi-allelic markers selected from the group consisting of SEQ ID NOs: 21–38, SEQ ID NOs: 57–62, and bi-allelic markers which are in linkage disequilibrium with the bi-allelic markers of SEQ ID NOs: 21–38, SEQ ID NOs: 57–62 or with the PG1 gene may be generated. In another embodiment, amplification products containing the polymorphic bases of two or more bi-allelic markers selected from the group consisting of SEQ ID NOs: 21–38, SEQ ID NOs: 57–62, and bi-allelic markers which are in linkage disequilibrium with the bi-allelic markers of SEQ ID NOs: 21–38, SEQ ID NOs: 57–62 or with the PG1 gene may be generated. In another embodiment, amplification products containing the polymorphic bases of five or more bi-allelic markers selected from the group consisting of SEQ ID NOs: 21–38, SEQ ID NOs: 57–62, and bi-allelic markers which are in linkage disequilibrium with the bi-allelic markers of SEQ ID NOs: 21–38, SEQ ID NOs: 57–62 or with the PG1 gene may be generated. In another embodiment, amplification products containing the polymorphic bases of more than five of the bi-allelic markers selected from the group consisting of SEQ ID NOs: 21–38, SEQ ID NOs: 57–62, and bi-allelic markers which are in linkage disequilibrium with the bi-allelic markers of SEQ ID NOs: 21–38, SEQ ID NOs: 57–62 or with the PG1 gene may be generated.

For example, the primers used to generate the amplification products may comprise the primers listed in FIGS. 6A or 6B (SEQ ID NOs: 39–56 and SEQ ID NOs: 63–68). FIG. 6A and FIG. 6B provide exemplary primers which may be used in the amplification reactions and the identities and locations of the polymorphic bases in the amplification products which are produced with the exemplary primers. The sequences of each of the alleles of the bi-allelic markers resulting from amplification using the primers in FIGS. 6A and 6B are listed in the accompanying Sequence Listing as SEQ ID NOs:21–38 and 57–62.

The PCR primers may be oligonucleotides of 10, 15, 20 or more bases in length which enable the amplification of the polymorphic site in the markers. In some embodiments, the amplification product produced using these primers may be at least 100 bases in length (i.e. 50 nucleotides on each side of the polymorphic base). In other embodiments, the amplification product produced using these primers may be at least 500 bases in length (i.e. 250 nucleotides on each side of the polymorphic base). In still further embodiments, the amplification product produced using these primers may be at least 1000 bases in length (i.e. 500 nucleotides on each side of the polymorphic base).

It will be appreciated that the primers listed in FIG. 6A and 6B are merely exemplary and that any other set of primers which produce amplification products containing the polymorphic nucleotides of one or more of the bi-allelic markers of SEQ ID NOs. 21–38 and SEQ ID NOs: 57–62 or bi-allelic markers in linkage disequilibrium with the sequences of SEQ ID NOs. 21–38 and SEQ ID NOs: 57–62 or with the PG1 gene, or a combination thereof may be used in the diagnostic methods.

Following the PCR amplification, the identities of the polymorphic bases of one or more of the bi-allelic markers of SEQ ID NOs: 21–38 and SEQ ID NOs: 57–62, or bi-allelic markers in linkage disequilibrium with the sequences of SEQ ID NOs. 21–38 and SEQ ID NOs: 57–62 or with the PG1 gene, or a combination thereof, are determined. The identities of the polymorphic bases may be determined using the microsequencing procedures described in Example 5 above and the microsequencing primers listed as features in the sequences of SEQ ID NOs: 21–38 and SEQ ID NOs: 57–62. It will be appreciated that the microsequencing primers listed as features in the sequences of SEQ ID NOs: 21–38 and SEQ ID NOs: 57–62 are merely exemplary and that any primer having a 3' end near the polymorphic nucleotide, and preferably immediately adjacent to the polymorphic nucleotide, may be used. Alternatively, the microsequencing analysis may be performed as described in Pastinen et al., Genome Research 7:606–614 (1997), the disclosure of which is incorporated herein by reference, which is described in more detail below.

Alternatively, the PCR product may be completely sequenced to determine the identities of the polymorphic bases in the bi-allelic markers. In another method, the identities of the polymorphic bases in the bi-allelic markers is determined by hybridizing the amplification products to microarrays containing allele specific olignonucleotides specific for the polymorphic bases in the bi-allelic markers. The use of microarrays comprising allele specific oligonucleotides is described in more detail below.

It will be appreciated that the identities of the polymorphic bases in the bi-allelic markers may be determined using techniques other than those listed above, such as conventional dot blot analyses.

Nucleic acids used in the above diagnostic procedures may comprise at least 10 consecutive nucleotides in the bi-allelic markers of SEQ ID NOs: 21–38 and SEQ ID NOs: 57–62 or the sequences complementary thereto. Alternatively, the nucleic acids used in the above diagnostic procedures may comprise at least 15 consecutive nucleotides in the bi-allelic markers of SEQ ID NOs: 21–38 and SEQ ID NOs: 57–62 or the sequences complementary thereto In some embodiments, the nucleic acids used in the above diagnostic procedures may comprise at least 20 consecutive nucleotides in the bi-allelic markers of SEQ ID NOs: 21–38 and SEQ ID NOs: 57–62 or the sequences complementary thereto. In still other embodiments, the nucleic acids used in the above diagnostic procedures may comprise at least 30 consecutive nucleotides in the bi-allelic markers of SEQ ID NOs: 21–38 and SEQ ID NOs: 57–62 or the sequences complementary thereto. In further embodiments, the nucleic acids used in the above diagnostic procedures may comprise more than 30 consecutive nucleotides in the bi-allelic markers of SEQ ID NOs: 21–38 and SEQ ID NOs: 57–62 or the sequences complementary thereto. In still further embodiments, the nucleic acids used in the above diagnostic procedures may comprise the entire sequence of the bi-allelic markers of SEQ ID NOs: 21–38 and SEQ ID NOs: 57–62 or the sequences complementary thereto.

Identification and Sequencing of the PG1 Gene

The above haplotype analysis indicated that 171 kb of genomic DNA between bi-allelic markers 4–14 and 99–221 totally or partially contains a gene responsible for prostate cancer. Therefore, the protein coding sequences lying within this region were characterized to locate the gene associated with prostate cancer. This analysis, described in further detail below, revealed a single protein coding sequence in the 171 kb, which was designated as the PG1 gene.

Template DNA for sequencing the PG1 gene was obtained as follows. BACs 189EO8 and 463FO1 were subcloned as previously described Plasmid inserts were first amplified by PCR on PE 9600 thermocyclers (Perkin-Elmer), using appropriate primers, AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data obtained as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector oligonucleotides were automatically removed from the sequence. However, the resulting sequence may contain 1 to 5 bases belonging to the vector sequences at their 5' end. If needed, these can easily be removed on a case by case basis.

The genomic sequence of the PG1 gene is provided in the accompanying Sequence Listing and is designated as SEQ ID NO: 1.

Potential exons in BAC-derived human genomic sequences were located by homology searches on protein, nucleic acid and EST (Expressed Sequence Tags) public databases. Main public databases were locally reconstructed. The protein database, NRPU (Non-redundant Protein Unique) is formed by a non-redundant fusion of the Genpept (Benson D. A. et al., Nucleic Acids Res. 24: 1–5 (1996), the disclosure of which is incorporated herein by reference), Swissprot (Bairoch, A. and Apweiler, R, Nucleic Acids Res. 24: 21–25 (1996), the disclosure of which is incorporated herein by reference) and PIR/NBRF (George, D. G. et al., Nucleic Acids Res. 24:17–20 (1996), the disclosure of which is incorporated herein by reference) databases. Redundant data were eliminated by using the NRDB software (Benson et al., supra) and internal repeats were masked with the XNU software (Benson et al., supra). Homologies found using the NRPU database allowed the identification of sequences corresponding to potential coding exons related to known proteins.

The EST local database is composed by the gbest section (1-9) of GenBank (Benson et al., supra), and thus contains all publicly available transcript fragments. Homologies found with this database allowed the localization of potentially transcribed regions.

The local nucleic acid database contained all sections of GenBank and EMBL (Rodriguez-Tome, P. et al., Nucleic Acids Res. 24: 6–12 (1996), the disclosure of which is incorporated herein by reference) except the EST sections. Redundant data were eliminated as previously described.

Similarity searches in protein or nucleic acid databases were performed using the BLAS software (Altschul, S. F. et al., J. Mol. Biol. 215: 403–410 (1990), the disclosure of which is incorporated herein by reference. Alignments were refined using the Fasta software, and multiple alignments used Clustal W. Homology thresholds were adjusted for each analysis based on the length and the complexity of the tested region, as well as on the size of the reference database.

Potential exon sequences identified as above were used as probes to screen cDNA libraries. Extremities of positive clones were sequenced and the sequence stretches were positioned on the genomic sequence of SEQ ID NO:1. Primers were then designed using the results from these alignments in order to enable the PG1 cloning procedure described below.

Cloning PG1 cDNA

PG1 cDNA was obtained as follows. 4 µl of ethanol suspension containing 1 mg of human prostate total RNA (Clontech laboratories, Inc., Palo Alto, USA; catalogue N. 64038-1, lot 7040869) was centrifuged, and the resulting pellet was air dried for 30 minutes at room temperature.

First strand cDNA synthesis was performed using the AdvantageTM RT-for-PCR kit (Clontech laboratories, Inc., Palo Alto, USA; catalogue N. K1402-1). 1 µl of 20 mM solution of primer PGRT32: TTTTTTTTTTTTTTTTTTTTGAAAT (SEQ ID NO:10) was added to 12.5 µl of RNA solution in water, heated at 74° C. for two and a half minutes and rapidly quenched in an ice bath. 10 µl of 5×RT buffer (50 mM Tris-HCl ph 8.3, 75 mM KCl, 3 mM MgCl2), 2.5 µl of dNTP mix (10 mM each), 1.25 µl of human recombinant placental RNA inhibitor were mixed with 1 ml of MMLV reverse transcriptase (200 units). 6.5 µl of this solution were added to RNA-primer mix and incubated at 42° C. for one hour. 80 µl of water were added and the solution was incubated at 94° C. for 5 minutes. 5 µl of the resulting solution were used in a Long Range PCR reaction with hot start, in 50 µl final volume, using 2 units of rtTHXL, 20 pmol/µl of each of GC1.5p.1: CTGTC-CCTGGTGCTCCACACGTACTC (SEQ ID NO:6) or GC1.5p2 TGGTGCTCCACACGTACTCCATGCGC (SEQ ID NO: 7) and GC1.3p: CTTGCCTGCTGGAGACACA-GAATTTCGATAGCAC (SEQ ID NO:9) primers with 35 cycles of elongation for 6 minutes at 67° C. in thermocycler.

The sequence of the PG1 cDNA obtained as described above (SEQ ID NO 3) is provided in the accompanying Sequence Listing. Results of Northern blot analysis of prostate mRNAs support the existence of a major PG1 cDNA having a 5–6 kb length.

Characterization of the PG1 Gene

The intron/exon structure of the gene was deduced by aligning the mRNA sequence from the cDNA of SEQ ID NO:3 and the genomic DNA sequence of SEQ ID NO: 1.

Figure 8:
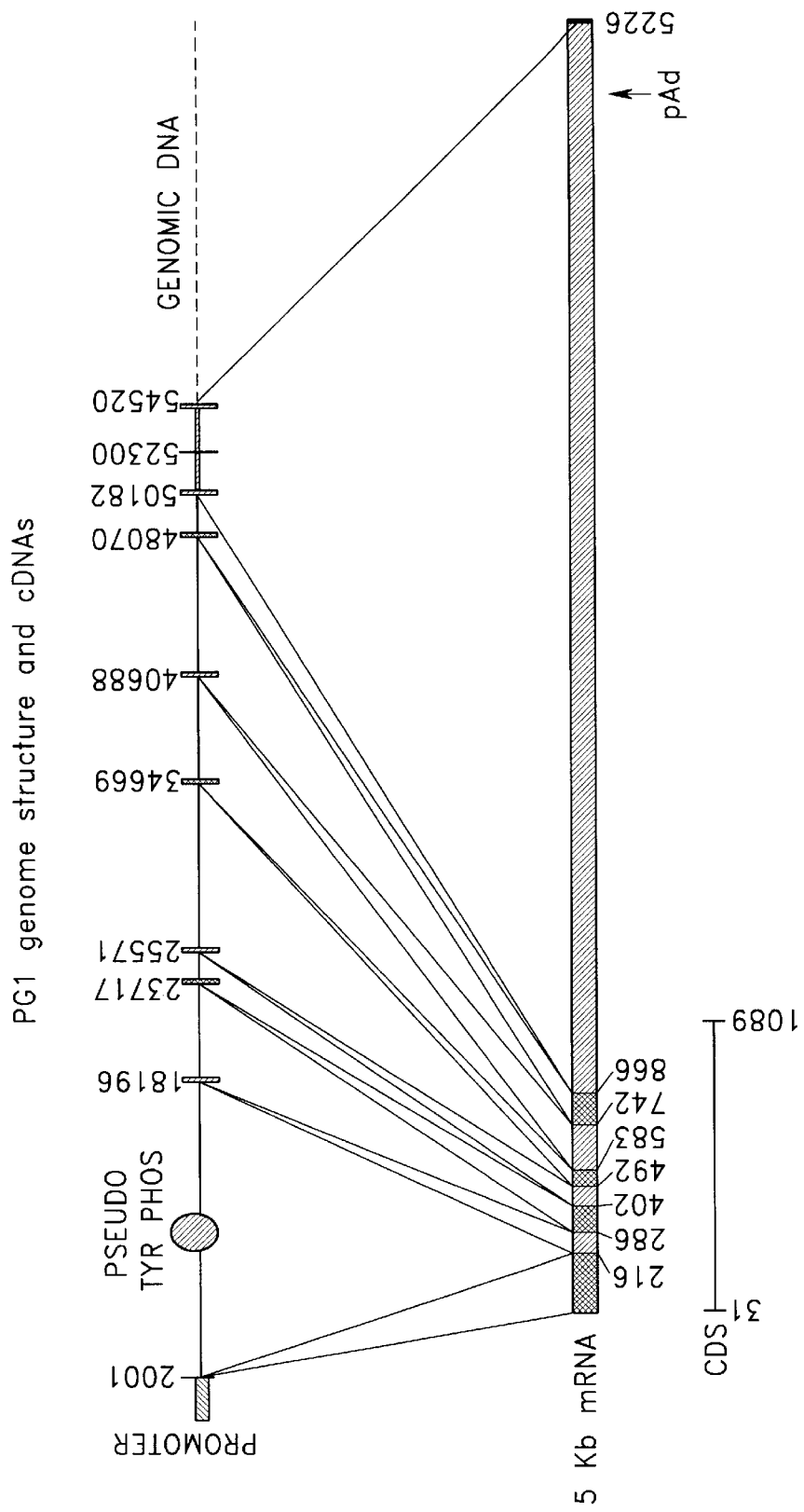
FIG. 8 shows the genomic structure of the PG1 gene.

The positions of the introns and exons in the PG1 genomic DNA are provided in FIGS. 7 and 8. FIG. 7 lists positions of the start and end nucleotides defining each of the at least 8 exons (labeled Exons A–H) in the sequence of SEQ ID NO: 1, the locations and phases of the 5' and 3' splice sites in the sequence of SEQ ID NO: 1, the position of the stop codon in the sequence of SEQ ID NO: 1, and the position of the polyadenylation site in the sequence of SEQ ID NO: 1.

FIG. 8 shows the positions of the exons within the PG1 genomic DNA and the PG1 mRNA, the location of a tyrosine phosphatase retro-pseudogene in the PG1 genomic DNA, the positions of the coding region in the mRNA, and the locations of the polyadenylation signal and polyA stretch in the mRNA.

As indicated in FIGS. 7 and 8, the PG1 gene comprises at least 8 exons, and spans more than 52 kb. The first intron contains a tyrosine phosphatase retropseudogene. A G/C rich putative promoter region lies between nucleotide 1629 and 1870 of SEQ ID NO: 1. A CCAAT box is present at nucleotide 1661 of SEQ ID NO: 1. The promoter region was identified as described in Prestridge, D. S., Predicting Pol II Promoter Sequences Using Transcription Factor Binding Sites, J. Mol. Biol. 249: 923–932 (1995), the disclosure of which is incorporated herein by reference.

It is possible that the methione listed as being the initiating methionine in the PG1 protein sequence of SEQ ID NO: 4 (based on the cDNA sequence of SEQ ID NO: 3) may actually be downstream but in phase with another methionine which acts as the iniating methionine. The genomic DNA sequence of SEQ ID NO: 1 contains a methionine upstream from the methionine at position number 1 of the protein sequence of SEQ ID NO: 4. If the upstream methionine is in fact the authentic initiation site, the sequence of the PG1 protein would be that of SEQ ID NO: 5. This possibility may be investigated by determining the exact position of the 5' end of the PG1 mRNA as follows.

One way to determine the exact position of the 5' end of the PG1 mRNA is to perform a 5'RACE reaction using the Marathon-Ready human prostate cDNA kit from Clontech (Catalog. No. PT1156-1). For example, the RACE reaction may employ the PG1 primers PG15RACE196 CAATATCTGGACCCCGGTGTAATTCTC (SEQ ID NO: 8) as the first primer. The second primer in the RACE reaction may be PG15RACE130n having the sequence GGTCGTCCAGCGCTTGGTAGAAG (SEQ ID NO: 2). The sequence analysis of the resulting PCR product, or the product obtained with other PG1 specific primers, will give the exact sequence of the initiation point of the PG1 transcript.

Alternatively, the 5'sequence of the PG1 transcript can be determined by conducting a PCR amplification with a series of primers extending from the 5'end of the presently identified coding region. In any event, the present invention contemplates use of PG1 nucleic acids and/or polypeptides coding for or corresponding to either SEQ ID NO:4 or SEQ ID NO: 5 or fragments thereof.

It is also possible that alternative splicing of the PG1 gene may result in additional translation products not described above. It is also possible that there are sequences upstream or downstream of the genomic sequence of SEQ ID NO: 1 which contribute to the translation products of the gene. Finally, alternative promoters may result in PG1 derived transcripts other than those described herein.

The promoter activity of the region between nucleotides 1629 and 1870 can be verified as described below. Alternatively, should this region lack promoter activity, the promoter responsible for driving expression of the PG1 gene may be identified as described below.

Genomic sequences lying upstream of the PG1 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the PG1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

Sequences within the PG1 promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art.

The promoters and other regulatory sequences located upstream of the PG1 gene may be used to design expression vectors capable of directing the expression of an inserted gene in a desired spatial, temporal, developmental, or quantitative manner. For example, since the PG1 promoter is presumably active in the prostate, it can be used to construct expression vectors for directing gene expression in the prostate.

Preferably, in such expression vectors, the PG1 promoter is placed near multiple restriction sites to facilitate the cloning of an insert encoding a protein for which expression is desired downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Nucleic acids encoding proteins which interact with sequences in the PG1 promoter may be identified using one-hybrid systems such as those described in the manual accompanying the Matchmaker One-Hybrid System kit available from Clontech (Catalog No. K1603-1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

Analysis of PG1 Protein Sequence

The PG1 cDNA of SEQ ID NO: 3 encodes a 353 amino-acid protein (SEQ ID NO:4). As indicated in the accompanying Sequence Listing, a Prosite analysis indicated that the PG1 protein has a leucine zipper motif, a potential glycosylation site, 3 potential casein kinase II phosphorylation sites, a potential cAMP dependent protein kinase phosphorylation site, 2 potential tyrosine kinase phosphorylation sites, 4 potential protein kinase C phosphorylation sites, 5 potential N-myristoylation sites, 1 potential tyrosine sulfation site, and one potential amidation site.

A search for membrane associated domains was conducted according to the methods described in Argos, P. et al., Structural Prediction of Membrane-bound Proteins, Elur. J. Biochem. 128: 565–575 (1982); Klein et al., Biochimica & Biophysica Acta 815: 468–476 (1985); and Eisenberg et al., J. Mol. Biol. 179: 125–142 (1984), the disclosures of which are incorporated herein by reference. The search revealed 5 potential transmembrane domains predicted to be integral membrane domains. These results suggest that the PG1 protein is likely to be membrane-associated and may be an integral membrane protein.

A homology search was conducted to identify proteins homologous to the PG1 protein. Several proteins were identified which share homology with the PG1 protein. FIG. 9 lists the accession numbers of several proteins which share homology with the PG1 protein in three regions designated box1, box2 and box3.

It will be appreciated that each of the motifs described above is also present in the protein of SEQ ID NO: 5, which would be produced if by translation initiation translated from the potential upstream methionine in the nucleic acid of SEQ ID NO: 1.

As indicated in FIG. 9, a distinctive pattern of homology to box 1, box 2 (SEQ ID NOs: 11–14) and box 3 (SEQ ID NOs: 15–20) is found amongst acyl glyerol transferases. For example, the plsC protein from *E. coli* (Accession Number P26647) shares homology with the box1 and box2 sequences, but not the box 3 sequence, of the PG1 protein. The product of this gene transfers acyl from acyl-coenzymeA to the sn2 position of 1-Acyl-sn-glycerol-3-phosphate (lysophosphatidic acid, LPA)(Coleman J., Mol Gen Genet. Mar. 1, 1992; 232(2): 295–303).

Box1 and box2 homologies, but not box 3 homologies, are also found in the SLCI gene product from baker's yeast (Accession Number P33333) and the mouse gene AB005623. Each of these genes are able to complement in vivo mutations in the bacterial plsC gene. (Nagiec M M, Wells G B, Lester R L, Dickson R C, J. Biol. Chem., Oct. 15, 1993; 268(29): 22156–22163, A suppressor gene that enables *Saccharomyces cerevisiae* to grow without making sphingolipids encodes a protein that resembles an *Escherichia coli* fatty acyltransferase; and Kume K, Shimizu T, Biochem. Biophys. Res. Commun. Aug. 28, 1997; 237(3): 663–666, cDNA cloning and expression of murine 1-acyl-sn-gycerol-3-phosphate acyltransferase, the disclosures of which are incorporated herein by reference).

Recently two different human homologues of the mouse AB005623 gene, Accession Numbers U89336 and U56417 were cloned and found to be localized to human chromosomes 6 and 9 (Eberhardt. C., Gray, P. W. and Tjoelker, L. W., J. Biol. Chem. 1997; 272, 20299–20305, Human lysophosphatidic acid acyltransferase cDNA cloning, expression, and localization to chromosome 9q34.3; and West, J., Tompkins, C. K., Balantac, N., Nudelman, E., Meengs, B., White, T., Bursten, S., Coleman, J., Kumar, A., Singer, J. W. and Leung, D. W, DNA Cell Biol. 6,691–701 (1997), Cloning and expression of two human lysophosphatidic acid acyltransferase cDNAs that enhance cytokine induced signaling responses in cells, the disclosures of which are incorporated herein by reference).

The enzymatic acylation of LPA results in 1,2-diacyl-sn-glycerol 3-phosphate, an intermediate to the biosynthesis of both glycerophospholipids and triacylglycerol. Several important signaling messengers participating in the transduction of mitogenic signals, induction of apoptosis, transmission of nerve impulses and other cellular responses mediated by membrane bound receptors belong to this metabolic pathway.

LPA itself is a potent regulator of mammalian cell proliferation. In fact, LPA is one of the major mitogens found in blood serum. (For a review: Durieux M E, Lynch K R, Trends Pharmacol. Sci. 1993 June; 14(6): 249–254, Signaling properties of lysophosphatidic acid. LPA can act as a survival factor to inhibit apoptosis of primary cells; and Levine J S, Koh J S, Triaca V, Lieberthal W, Am. J. Physiol. 1997 October; 273(4Pt2): F575–F585, Lysophosphatidic acid: a novel growth and survival factor for renal proximal tubular cells, the disclosures of which are incorporated herein by reference). This function of LPA is mediated by the lipid kinase phosphatidylinositol 3-kinase.

Phosphatidylinositol and its derivatives present another class of messengers emerging from the 1-acyl-sn-glycerol-3-phosphate acyltransferase pathway. (Toker A, Cantley L C, Nature Jun. 12, 1997; 387(6634): 673–676, Signaling through the lipid products of phosphoinositide-3-OH kinase; Martin T F, Curr. Opin. Neurobiol. 1997 June 7(3): 331–338, Phosphoinositides as spatial regulators of membrane traffic; and Hsuan J J, et al., Int. J. Biochem. Cell Biol. Mar. 1st, 1997; 29(3): 415–435, Growth factor-dependent phosphoinositide signalling, the disclosures of which are incorporated herein by reference).

Cell growth, differentiation and apoptosis can be affected and modified by enzymes involved in this metabolic pathway. Consequently, alteration of this pathway could facilitate cancer cell progression. Modulation of the activity of enzymes in this pathway using agents such as enzymatic inhibitors could be a way to restore a normal phenotype to cancerous cells.

Ashagbley A, Samadder P, Bittman R, Erukulla R K, Byun H S, Arthur G have recently shown that ether-linked analogue of lysophosphatidic acid: 4-O-hexadecyl-3(S)-O-methoxybutanephosphonate can effectively inhibit the proliferation of several human cancerous cell lines, including DU145 line of prostate cancer origin. (Anticancer Res 1996 July; 16(4A): 1813–1818, Synthesis of ether-linked analogues of lysophosphatidate and their effect on the proliferation of human epithelial cancer cells in vitro, the disclosure of which is incorporated herein by reference)

Structural differences between the PG1 family of cellular proteins and the functionally confirmed 1-acyl-sn-glycerol-3-phosphate acyltransferase family, evidenced by the existence of a different pattern of homology to box3, could point to unique substrate specificity in the phospholipid metabolic pathway, to specific interaction with other cellular components or to both.

Further analysis of the function of the PG1 gene can be conducted, for example, by constructing knockout mutations in the yeast homologues of the PG1 gene in order to elucidate the potential function of this protein family, and to test potential substrate analogs in order to revert the malignant phenotype of human prostate cancer cells.

Identification of Mutations in the PG1 Gene which are Associated with a Detectable Phenotype Mutations in the PG1 gene which are responsible for a detectable phenotype may be identified by comparing the sequences of the PG1 genes from affected and unaffected individuals as described in Example 9 below. The detectable phenotype may comprise a variety of manifestations of altered PG1 function, including prostate cancer, hepatocellular carcinoma, colorectal cancer, non-small cell lung cancer, squamous cell carcinoma, or other conditions. The mutations may comprise point mutations, deletions, or insertions of the PG1 gene. The mutations may lie within the coding sequence for the PG1 protein or within regulatory regions in the PG1 gene.

EXAMPLE 9

Oligonucleotide primers are designed to amplify the sequences of each of the exons or the promoter region of the PG1 gene. The oligonucleotide primers may comprise at least 10 consecutive nucleotides of the PG1 genomic DNA of SEQ ID NO:1 or the PG1 cDNA of SEQ ID NO:3 or the sequences complementary thereto. Preferably, the oligonucleotides comprise at least 15 consecutive nucleotides of the PG1 genomic DNA of SEQ ID NO:1 or the PG1 cDNA of SEQ ID NO: 3 or the sequences complementary thereto. In some embodiments, the oligonucleotides may comprise at least 20 consecutive nucleotides of the PG1 genomic DNA of SEQ ID NO: 1 or the PG1 cDNA of SEQ ID NO:3 or the sequences complementary thereto. In other embodiments, the oligonucleotides may comprise 25 or more consecutive nucleotides of the PG1 genomic DNA of SEQ ID NO: 1 or the PG1 cDNA of SEQ ID NO: 3 or the sequences complementary thereto.

Each primer pair is used to amplify the exon or promoter region from which it is derived. Amplification is carried out on genomic DNA samples from affected patients and unaffected controls using the PCR conditions described above. Amplification products from the genomic PCRs are subjected to automated dideoxy terminator sequencing reactions and electrophoresed on ABI 377 sequencers. Following gel image analysis and DNA sequence extraction, ABI sequence data are automatically analyzed to detect the presence of sequence variations among affected and unaffected individuals. Sequences are verified by determining the sequences of both DNA strands for each individual. Preferably, these candidate mutations are detected by comparing individuals homozygous for haplotype 5 of FIG. 4 and controls not carrying haplotype 5 or related haplotypes.

Candidate polymorphisms suspected of being responsible for the detectable phenotype, such as prostate cancer or other conditions, are then verified by screening a larger population of affected and unaffected individuals using the microsequencing technique described above. Polymorphisms which exhibit a statistically significant correlation with the detectable phenotype are deemed responsible for the detectable phenotype.

Other techniques may also be used to detect polymorphisms associated with a detectable phenotype such as prostate cancer or other conditions. For example, polymorphisms may be detected using single stranded conformation analyses such as those described in Orita et al., Proc. Natl. Acad. Sci. U.S.A. 86: 2776–2770 (1989), the disclosure of which is incorporated herein by reference. In this approach, polymorphisms are detected through altered migration on SSCA gels.

Alternatively, polymorphisms may be identified using clamped denaturing gel electrophoresis, heteroduplex analysis, chemical mismatch cleavage, and other conventional techniques as described in Sheffield, V. C. et al, Proc. Natl. Acad. Sci. U.S.A 49: 699–706 (1991); White, M. B. et al., Genomics 12: 301–306 (1992); Grompe, M. et al., Proc. Natl. Acad. Sci. U.S.A 86: 5855–5892 (1989); and Grompe, M. Nature Gentics 5: 111–117 (1993), the disclosures of which are incorporated herein by reference.

The PG1 genes from individuals carrying PG1 mutations responsible for the detectable phenotype, or cDNAs derived therefrom, may be cloned as follows. Nucleic acid samples are obtained from individuals having a PG1 mutation associated with the detectable phenotype. The nucleic acid samples are contacted with a probe derived from the PG1 genomic DNA of SEQ ID NO: 1 or the PG1 cDNA of SEQ ID NO:3. Nucleic acids containing the mutant PG1 allele are identified using conventional techniques. For example, the mutant PG1 gene, or a cDNA derived therefrom, may be obtained by conducting an amplification reaction using primers derived from the PG1 genomic DNA of SEQ ID NO: 1 or the PG1 cDNA of SEQ ID NO:3. Alternatively, the mutant PG1 gene, or a cDNA derived therefrom, may be identified by hybridizing a genomic library or a cDNA library obtained from an individual having a mutant PG1 gene with a detectable probe derived from the PG1 genomic DNA of SEQ ID NO: 1 or the PG1 cDNA of SEQ ID NO:3. Alternatively, the mutant PG1 allele may be obtained by contacting an expression library from an individual carrying a PG1 mutation with a detectable antibody against the PG1 proteins of SEQ ID NO: 4 or SEQ ID NO: 5 which has been prepared as described below. Those skilled in the art will appreciate that the PG1 genomic DNA of SEQ ID NO: 1, the PG1 cDNA of SEQ ID NO: 3 and the PG1 proteins of SEQ ID NOs: 4 and 5 may be used in a variety of other conventional techniques to obtain the mutant PG1 gene.

In another embodiment the mutant PG1 allele which causes a detectable phenotype can be isolated by obtaining a nucleic acid sample such as a genomic library or a cDNA library from an individual expressing the detectable phenotype. The nucleic acid sample can be contacted with one or more probes lying in the 8p23 region of the human genome. Nucleic acids in the sample which contain the PG1 gene can be identified by conducting sequencing reactions on the nucleic acids which hybridize to the markers from the 8p23 region of the human genome.

The region of the PG1 gene containing the mutation responsible for the detectable phenotype may also be used in diagnostic techniques such as those described below. For example, oligonucleotides containing the mutation responsible for the detectable phenotype may be used in amplification or hybridization based diagnostics, such as those described herein, for detecting individuals suffering from the detectable phenotype or individuals at risk of developing the detectable phenotype at a subsequent time. In addition, the PG1 allele responsible for the detectable phenotype may be used in gene therapy as described herein. The PG1 allele responsible for the detectable phentoype may also be cloned into an expression vector to express the mutant PG1 protein a described herein.

During the search for bi-allelic markers associated with prostate cancer, a number of polymorphic bases were discovered which lie within the PG1 gene. The identities and positions of these polymorphic bases are listed as features in the accompanying Sequence Listing for the PG1 genomic DNA of SEQ ID NO: 1. The polymorphic bases may be used in the above-descrived diagnostic techniques for determining whether an individual is at risk for developing prostate cancer at a subsequent date or suffers from prostate cancer as a result of a PG1 mutation. The identities of the nucleotides present at the polymorphic positions in a nucleic acid sample may be determined using the techniques, such as microsequencing analysis, which are described above.

It is possible that one or more of these polymorphisms (or other polymorphic bases) may be mutations which are associated with prostate cancer. To determine whether a polymorphism is responsible for prostate cancer, the frequency of each of the alleles in individuals suffering from prostate cancer and unaffected individuals is measured as described in the haplotype analysis above. Those mutations which occur at a statistically significant frequency in the affected population are deemed to be responsible for prostate cancer.

cDNAs containing the identified mutant PG1 gene may be prepared as described above and cloned into expression vectors as described below. The proteins expressed from the expression vectors may be used to generate antibodies specific for the mutant PG1 proteins as described below. In addition, allele specific probes containing the PG1 mutation responsible for prostate cancer may be used in the diagnostic techniques described below.

Genes sharing homology to the PG1 gene may be identified as follows.

EXAMPLE 10

Alternatively, a cDNA library or genomic DNA library to be screened for genes sharing homology to the PG1 gene may be obtained from a commercial source or made using techniques familiar to those skilled in the art. The cDNA library or genomic DNA library is hybridized to a detectable probe comprising at least 10 consecutive nucleotides from the PG1 cDNA of SEQ ID NO:3, the PG1 genomic DNA of SEQ ID NO: 1, or the sequences complementary thereto, using conventional techniques. Preferably, the probe comprises at least 12, 15, or 17 consecutive nucleotides from the PG1 cDNA of SEQ ID NO:3, the PG1 genomic DNA of SEQ ID NO: 1, or the sequences complementary thereto. More preferably, the probe comprises at least 20–30 consecutive nucleotides from the PG1 cDNA of SEQ ID NO:3, the PG1 genomic DNA of SEQ ID NO: 1, or the sequences complementary thereto. In some embodiments, the probe comprises more than 30 nucleotides from the PG1 cDNA of SEQ ID NO:3, the PG1 genomic DNA of SEQ ID NO: 1, or the sequences complementary thereto.

Techniques for identifying cDNA clones in a cDNA library which hybridize to a given probe sequence are disclosed in Sambrook et al., Molecular Cloning: A Laboratory Manual 2d Ed., Cold Spring Harbor Laboratory Press, 1989, the disclosure of which is incorporated herein by reference. The same techniques may be used to isolate genomic DNAs sharing homology with the PG1 gene.

Briefly, cDNA or genomic DNA clones which hybridize to the detectable probe are identified and isolated for further manipulation as follows. A probe comprising at least 10 consecutive nucleotides from the PG1 cDNA of SEQ ID NO:3, the PG1 genomic DNA of SEQ ID NO: 1, or the sequences complementary thereto, is labeled with a detectable label such as a radioisotope or a fluorescent molecule. Preferably, the probe comprises at least 12, 15, or 17 consecutive nucleotides from the PG1 cDNA of SEQ ID NO:3, the PG1 genomic DNA of SEQ ID NO: 1, or the sequences complementary thereto. More preferably, the probe comprises 20–30 consecutive nucleotides from the PG1 cDNA of SEQ ID NO:3, the PG1 genomic DNA of SEQ ID NO: 1, or the sequences complementary thereto. In some embodiments, the probe comprises more than 30 nucleotides from the PG1 cDNA of SEQ ID NO:3, the PG1 genomic DNA of SEQ ID NO: 1, or the sequences complementary thereto.

Techniques for labeling the probe are well known and include phosphorylation with polynucleotide kinase, nick translation, in vitro transcription, and non-radioactive techniques. The cDNAs or genomic DNAs in the library are transferred to a nitrocellulose or nylon filter and denatured. After incubation of the filter with a blocking solution, the filter is contacted with the labeled probe and incubated for a sufficient amount of time for the probe to hybridize to cDNAs or genomic DNAs containing a sequence capable of hybridizing to the probe.

By varying the stringency of the hybridization conditions used to identify cDNAs or genomic DNAs which hybridize to the detectable probe, cDNAs or genomic DNAs having different levels of homology to the probe can be identified and isolated. To identify cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: $Tm=81.5+16.6(\log [Na+])+0.41(\text{fraction } G+C)-(600/N)$ where N is the length of the probe.

If the hybridization is carried out in a solution containing formamide, the melting temperature may be calculated using the equation $Tm=81.5+16.6(\log [Na+])+0.41(\text{fraction } G+C)-(0.63\% \text{ formamide})-(600/N)$ where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 15–25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

cDNAs or genomic DNAs homologous to the PG1 gene which have hybridized to the probe are identified by autoradiography or other conventional techniques.

The above procedure may be modified to identify cDNAs or genomic DNAs having decreasing levels of homology to the probe sequence. For example, to obtain cDNAs or genomic DNAs of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide.

cDNAs or genomic DNAs which have hybridized to the probe are identified by autoradiography.

If it is desired to obtain nucleic acids homologous to the PG1 gene, such as allelic variants thereof or nucleic acids encoding proteins related to the PG1 protein, the level of homology between the hybridized nucleic acid and the PG1 gene may readily be determined. To determine the level of homology between the hybridized nucleic acid and the PG1 gene, the nucleotide sequences of the hybridized nucleic acid and the PG1 gene are compared. For example, using the above methods, nucleic acids having at least 95% nucleic acid homology to the PG1 gene may be obtained and identified. Similarly, by using progressively less stringent hybridization conditions one can obtain and identify nucleic acids having at least 90%, at least 85%, at least 80% or at least 75% homology to the PG1 gene.

To determine whether a clone encodes a protein having a given amount of homology to the PG1 protein, the amino acid sequence of the PG1 protein is compared to the amino acid sequence encoded by the hybridizing nucleic acid. Homology is determined to exist when an amino acid sequence in the PG1 protein is closely related to an amino acid sequence in the hybridizing nucleic acid. A sequence is closely related when it is identical to that of the PG1 sequence or when it contains one or more amino acid substitutions therein in which amino acids having similar characteristics have been substituted for one another. Using the above methods, one can obtain nucleic acids encoding proteins having at least 95%, at least 90%, at least 85%, at least 80% or at least 75% homology to the proteins encoded by the PG1 probe.

Diagnosis of Individuals at Risk for Developing Prostate Cancer or Individuals Suffering from Prostate Cancer as a Result of a Mutation in the PG1 Gene Individuals may then be screened for the presence of polymorphisms in the PG1 gene or protein which are associated with a detectable phenotype such as prostate cancer or other conditions as described in Example 11 below. The individuals may be screened while they are asymptomatic to determine their risk of developing prostate cancer or other conditions at a subsequent time. Alternatively, individuals suffering from prostate cancer or other conditions may be screened for the presence of polymorphisms in the PG1 gene or protein in order to determine whether therapies which target the PG1 gene or protein should be applied.

EXAMPLE 11

Nucleic acid samples are obtained from a symptomatic or asymptomatic individual. The nucleic acid samples may be obtained from blood cells as described above or may be obtained from other tissues or organs. For individuals suffering from prostate cancer, the nucleic acid sample may be obtained from the tumor. The nucleic acid sample may comprise DNA, RNA, or both. The nucleotides at positions in the PG1 gene where mutations lead to prostate cancer or other detectable phenotypes are determined for the nucleic acid sample.

In one embodiment, a PCR amplification is conducted on the nucleic acid sample as described above to amplify regions in which polymorphisms associated with prostate cancer or other detectable phenotypes have been identified. The amplification products are sequenced to determine whether the individual possesses one or more PG1 polymorphisms associated with prostate cancer or other detectable phenotypes.

Alternatively, the nucleic acid sample may be subjected to microsequencing reactions as described above to determine whether the individual possesses one or more PG1 polymorphisms associated with prostate cancer or another detectable phenotype resulting from a mutation in the PG1 gene.

In another embodiment, the nucleic acid sample may be contacted with one or more allele specific oligonucleotides which specifically hybridize to one or more PG1 alleles associated with prostate cancer or another detectable phenotype. The nucleic acid sample is also contacted with a second PG1 oligonucleotide capable of producing an amplification product when used with the allele specific oligonucleotide in an amplification reaction. The presence of an amplification product in the amplification reaction indicates that the individual possesses one or more PG1 alleles associated with prostate cancer or another detectable phenotype.

Determination of PG1 Expression Levels

As discussed above, PG1 polymorphisms associated with prostate cancer or other detectable phenotypes may exert their effects by increasing, decreasing, or eliminating PG1 expression. Accordingly, PG1 expression levels in individuals suffering from prostate cancer or other detectable phenotypes may be compared to those of unaffected individuals to determine whether overexpression, underexpression, or loss of expression of PG1 causes prostate cancer or another detectable phenotype. Individuals may be tested to determine whether they are at risk of developing prostate cancer at a subsequent time or whether they suffer from prostate cancer resulting from a mutation in the PG1 gene by determining whether they exhibit a level of PG1 expression associated with prostate cancer. Similarly, individuals may be tested to determine whether they suffer from another PG1 mediated detectable phenotype or whether they are at risk of suffering from such a condition at a subsequent time.

Expression levels in nucleic acid samples from affected and unaffected individuals may be determined by performing Northern blots using detectable probes derived from the PG1 gene or the PG1 cDNA. A variety of conventional Northern blotting procedures may be used to detect and quantitate PG1 expression, including those disclosed in Current Protocols in Molecular Biology, John Wiley 503 Sons, Inc. 1997 and Sambrook et al. Molecular Cloning: A Laboratory Manual, Second Edition, Cold Spring Harbor Laboratory Press, 1989, the entire disclosures of which are incorporated herein by reference.

Alternatively, PG1 expression levels may be determined as described in Example 12 below.

EXAMPLE 12

Expression levels and patterns of PG1 may be analyzed by solution hybridization with long probes as described in International Patent Application No. WO 97/05277, the entire contents of which are hereby incorporated by reference. Briefly, the PG1 cDNA or the PG1 genomic DNA described above, or fragments thereof, is inserted at a cloning site immediately downstream of a bacteriophage (T3, T7 or SP6) RNA polymerase promoter to produce antisense RNA. Preferably, the PG1 insert comprises at least 100 or more consecutive nucleotides of the genomic DNA sequence of SEQ ID NO: 1 or the cDNA sequences of SEQ ID NO: 3. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of PG1 gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the PG1 genomic DNA of SEQ ID NO:1, the PG1 cDNA of SEQ ID NO:3 or the sequences complementary thereto or fragments thereof. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of PG1 gene expression may be performed with a complementary DNA microarray as described by Schena et al. (Science 270: 467–470, 1995; Proc. Natl. Acad. Sci. U.S.A. 93: 10614–10619, 1996). Full length PG1 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 $cm^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of PG1 gene expression may also be performed with full length PG1 cDNAs or fragments thereof in complementary DNA arrays as described by Pietu et al. (Genome Research 6: 492–503, 1996). The full length PG1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the PG1 genomic DNA, the PG1 cDNA, or fragments thereof can be done through high density nucleotide arrays as described by Lockhart et al. (Nature Biotechnology 14: 1675–1680, 1996) and Sosnowsky et al. (Proc. Natl. Acad. Sci. 94: 1119–1123, 1997). Oligonucleotides of 15–50 nucleotides from the sequences of the PG1 genomic DNA of SEQ ID NO: 1, the PG1 cDNA of SEQ ID NO: 3, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

PG1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94: 1119–1123)., the dyes or labeling compounds are detected and quantified. Duplicate hybridizations are performed. Comparative analysis of the intensity of the signal originating from cDNA probes on the same target oligonucleotide in different cDNA samples indicates a differential expression of PG1 mRNA.

The above methods may also be used to determine whether an individual exhibits a PG1 expression pattern associated with prostate cancer. In such methods, nucleic acid samples from the individual are assayed for PG1 expression as described above. If a PG1 expression pattern associated with prostate cancer is observed, an appropriate diagnosis may be rendered and appropriate therapeutic techniques which target the PG1 gene or protein may be applied.

The above methods may also be applied using allele specific probes to determine whether an individual possesses a PG1 allele associated with prostate cancer. In such approaches, one or more allele specific oligonucleotides containing polymorphic nucleotides in the PG1 gene which are associated with prostate cancer are fixed to a microarray. The array is contacted with a nucleic acid sample from the individual being tested under conditions which permit allele specific hybridization of the sample nucleic acid to the allele specific PG1 probes. Hybridization of the sample nucleic acid to one or more of the allele specific PG1 probes indicates that the individual suffers from prostate cancer caused by the PG1 gene or that the individual is at risk for developing prostate cancer at a subsequent time.

Alternatively, the minisequencing approach of Pastinen et al., Genome Research 7: 606–614 (1997), the disclosure of which is incorporated herein by reference, may be used to determine whether an individual possesses a PG1 allele associated with prostate cancer. In this approach, a PCR reaction is performed on the DNA or RNA of the individual to be tested to amplify the PG1 gene, the PG1 mRNA, or portions thereof in which one or more alleles associated with prostate cancer are located. The amplification product is hybridized to one or more PG1 oligonucleotides having their 3' end one base from the position of a PG1 polymorphism associated with prostate cancer which is fixed to a surface. The oligonucleotides are extended one base using a detectably labeled dNTP and a polymerase. Incorporation of a detectably labeled base indicative of a PG1 allele associated with prostate cancer indicates that the individual suffers from prostate cancer caused by the PG1 gene or that the individual is at risk for developing prostate cancer at a subsequent time.

Expression of the PG1 Protein

The cDNA of SEQ ID NO:3 (encoding the protein of SEQ ID NO: 4), cDNAs or synthetic DNAs encoding the protein of SEQ ID NO: 5, or a nucleic acid encoding a PG1 allele responsible for a detectable phenotype may be used to express the PG1 protein or portions thereof as described in Example 13 below.

EXAMPLE 13

To express the proteins encoded by the PG1 cDNA of SEQ ID NO: 3 or portions thereof, nucleic acids containing the coding sequence for the PG1 protein or portions thereof to be expressed cloned into a suitable expression vector. To express the proteins encoded by a cDNA encoding the protein of SEQ ID NO: 5, a nucleic acid containing the coding sequence for the protein of SEQ ID NO:5 is cloned into a suitable expression vector. To express the proteins encoded by a cDNA encoding a mutant PG1 protein responsible for a detectable phenotype, a nucleic acid encoding the mutant PG1 protein or a portion thereof is cloned into a suitable expression vector. The nucleic acid encoding the PG1 protein or polypeptide to be expressed is operably linked to a promoter in an expression vector using conventional cloning technology. The PG1 insert in the expression vector may comprise the full coding sequence for the PG1 protein or a portion thereof. For example, the PG1 derived insert may encode a polypeptide comprising at least 10 consecutive amino acids of the PG1 proteins of SEQ ID NO: 4, SEQ ID NO: 5, or a mutant PG1 protein responsible for a detectable phenotype. In some embodiments, the nucleic acid may encode a polypeptide comprising at least 15 consecutive amino acids of the PG1 proteins of SEQ ID NO 4, SEQ ID NO:5, or a mutant PG1 protein responsible for a detectable phenotype. In other embodiments, the nucleic acid may encode a polypeptide comprising at least 25 consecutive amino acids of the PG1 proteins of SEQ ID NO 4, SEQ ID NO:5, or a mutant PG1 protein responsible for a detectable phenotype.

The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The following is provided as one exemplary method to express the PG1 protein or a portion thereof. In one embodiment, the entire coding sequence of the PG1 cDNA through the poly A signal of the cDNA are operably linked to a promoter in the expression vector. Alternatively, if the nucleic acid encoding a portion of the PG1 protein lacks a methionine to serve as the initiation site, an initiating methionine can be introduced next to the first codon of the nucleic acid using conventional techniques. Similarly, if the insert from the PG1 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the PG1 protein or a portion thereof may be obtained by PCR from a bacterial vector containing the PG1 cDNA of SEQ ID NO: 3 using oligonucleotide primers complementary to the PG1 cDNA or portion thereof and containing restriction endonuclease sequences for Pst I incorporated into the 5'primer and BglII at the 5' end of the corresponding cDNA 3' primer, taking care to ensure that the sequence encoding the PG1 protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

Alternatively, the nucleic acids encoding the PG1 protein or a portion thereof may be cloned into pED6dpc2 (Genetics Institute, Cambridge, Mass.). The resulting pED6dpc2 constructs may be transfected into a suitable host cell, such as COS 1 cells. Methotrexate resistant cells are selected and expanded.

The above procedures may also be used to express a mutant PG1 protein responsible for a detectable phenotype or a portion thereof.

The expressed proteins may be purified using conventional purification techniques such as ammonium sulfate precipitation or chromatographic separation based on size or charge. The protein encoded by the nucleic acid insert may also be purified using standard immunochromatography techniques. In such procedures, a solution containing the expressed PG1 protein or portion thereof, such as a cell extract, is applied to a column having antibodies against the PG1 protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the PG1 protein or a portion thereof, the proteins expressed from host cells containing an expression vector containing an insert encoding the PG1 protein or a portion thereof can be compared to the proteins expressed in host cells containing the expression vector without an insert. The presence of a band in samples from cells containing the expression vector with an insert which is absent in samples from cells containing the expression vector without an insert indicates that the PG1 protein or a portion thereof is being expressed. Generally, the band will have the mobility expected for the PG1 protein or portion thereof. However, the band may have a mobility different than that expected as a result of modifications such as glycosylation, ubiquitination, or enzymatic cleavage.

Antibodies capable of specifically recognizing the expressed PG1 protein or a portion thereof may be generated using synthetic 15-mer peptides having a sequence encoded by the appropriate nucleic acid. The synthetic peptides are injected into mice to generate antibody to the polypeptide encoded by the nucleic acid.

If antibody production is not possible, the nucleic acids encoding the PG1 protein or a portion thereof may be incorporated into expression vectors designed for use in purification schemes employing chimeric polypeptides. In such strategies the nucleic acid encoding the PG1 protein or a portion thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the PG1 protein or portion thereof. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Assaying the PG1 Protein for Involvement in Receptor/Ligand Interactions

The expressed PG1 protein or portion thereof may be evaluated for involvement in receptor/ligand interactions as described in Example 14 below.

EXAMPLE 14

The proteins encoded by the PG1 gene or a portion thereof may also be evaluated for their involvement in receptor/ligand interactions. Numerous assays for such involvement are familiar to those skilled in the art, including the assays disclosed in the following references, which are incorporated herein by reference: Chapter 7.28 (Measurement of Cellular Adhesion under Static Conditions 7.28.1–7.28.22) in Current Protocols in Immunology, J. E. Coligan et al. Eds. Greene Publishing Associates and Wiley-Interscience; Takai et al., Proc. Natl. Acad. Sci. USA 84: 6864–6868, 1987; Bierer et al., J. Exp. Med. 168: 1145–1156, 1988; Rosenstein et al., J. Exp. Med. 169: 149–160, 1989; Stoltenborg et al., J. Immunol. Methods 175: 59–68, 1994; Stitt et al., Cell 80: 661–670, 1995; Gyuris et al., Cell 75: 791–803, 1993.

For example, the proteins of the present invention may demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as sclectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The PG1 protein or portions thereof described above may be used in drug screening procedures to identify molecules which are agonists, antagonists, or inhibitors of PG1 activity. The PG1 protein or portion thereof used in such analyses may be free in solution or linked to a solid support. Alternatively, PG1 protein or portions thereof can be expressed on a cell surface. The cell may naturally express the PG1 protein or portion thereof or, alternatively, the cell may express the PG1 protein or portion thereof from an expression vector such as those described below.

In one method of drug screening, eucaryotic or procaryotic host cells which are stably transformed with recombinant polynucleotides in order to express the PG1 protein or a portion thereof are used in conventional competitive binding assays or standard direct binding assays. For example, the formation of a complex between the PG1 protein or a portion thereof and the agent being tested may be measured in direct binding assays. Alternatively, the ability of a test agent to prevent formation of a complex between the PG1 protein or a portion thereof and a known ligand may be measured.

Alternatively, the high throughput screening techniques disclosed in the published PCT application WO 84/03564, the disclosure of which is incorporated herein by reference, may be used. In such techniques, large numbers of small peptides to be tested for PG1 binding activity are synthesized on a surface and affixed thereto. The test peptides are contacted with the PG1 protein or a portion thereof, followed by a wash step. The amount of PG1 protein or portion thereof which binds to the test compound is quantitated using conventional techniques.

In some methods, PG1 protein or a portion thereof may be fixed to a surface and contacted with a test compound. After a washing step, the amount of test compound which binds to the PG1 protein or portion thereof is measured.

In another approach, the three dimensional structure of the PG1 protein or a portion thereof may be determined and used for rational drug design.

Alternatively, the PG1 protein or a portion thereof may be expressed in a host cell using expression vectors such as those described herein. The PG1 protein or portion thereof may be an isotype which is associated with prostate cancer or an isotype which is not associated with prostate cancer. The cells expressing the PG1 protein or portion thereof are contacted with a series of test agents and the effects of the test agents on PG1 activity are measured. Test agents which modify PG1 activity may be employed in therapeutic treatments.

The above procedures may also be applied to evaluate mutant PG1 proteins responsible for a detectable phenotype.

Identification of Proteins which Interact with the PG1 Protein

Proteins which interact with the PG1 protein may be identified as described in Example 15 below.

EXAMPLE 15

Proteins which interact with the PG1 protein or a portion thereof, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), which is incorporated herein by reference, nucleic acids encoding the PG1 protein or a portion thereof, are inserted into an expression vector such that they are in frame with DNA encoding the DNA binding domain of the yeast transcriptional activator GAL4. cDNAs in a cDNA library which encode proteins which might interact with the polypeptides encoded by the nucleic acids encoding the PG1 protein or a portion thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the nucleic acid inserts.

Alternatively, the system described in Lustig et al., Methods in Enzymology 283: 83–99 (1997), the disclosure of which is incorporated herein by reference, may be used for identifying molecules which interact with the PG1 protein or a portion thereof. In such systems, in vitro transcription reactions are performed on vectors containing an insert encoded the PG1 protein or a portion thereof cloned downstream of a promoter which drives in vitro transcription. The resulting mRNA is introduced into *Xenopus laevis* oocytes. The oocytes are then assayed for a desired activity.

Alternatively, the in vitro transcription products produced as described above may be translated in vitro. The in vitro translation products can be assayed for a desired activity or for interaction with a known polypeptide.

The system described in U.S. Pat. No. 5,654,150, the disclosure of which is incorporated herein by reference, may also be used to identify molecules which interact with the PG1 protein or a portion thereof. In this system, pools of cDNAs are transcribed and translated in vitro and the reaction products are assayed for interaction with a known polypeptide or antibody.

Proteins or other molecules interacting with the PG1 protein or portions thereof can be found by a variety of additional techniques. In one method, affinity columns containing the PG1 protein or a portion thereof can be constructed. In some versions of this method the affinity column contains chimeric proteins in which the PG1 protein or a portion thereof is fused to glutathione S-transferase. A mixture of cellular proteins or pool of expressed proteins as described above is applied to the affinity column. Proteins interacting with the polypeptide attached to the column can then be isolated and analyzed on 2-D electrophoresis gel as described in Ramunsen et al. Electrophoresis, 18, 588–598 (1997), the disclosure of which is incorporated herein by reference. Alternatively, the proteins retained on the affinity column can be purified by electrophoresis based methods and sequenced. The same method can be used to isolate antibodies, to screen phage display products, or to screen phage display human antibodies.

Proteins interacting with the PG1 protein or portions thereof can also be screened by using an Optical Biosensor as described in Edwards et Leatherbarrow, Analytical Biochemistry, 246, 1–6 (1997), the disclosure of which is incorporated herein by reference. The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred nanometers from the sensor surface). In these screening assays, the target molecule can be the PG1 protein or a portion thereof and the test sample can be a collection of proteins extracted from tissues or cells, a pool of expressed proteins, combinatorial peptide and/or chemical libraries, or phage displayed peptides. The tissues or cells from which the test proteins are extracted can originate from any species.

In other methods, a target protein is immobilized and the test population is the PG1 protein or a portion thereof.

To study the interaction of the PG1 protein or a portion thereof with drugs, the microdialysis coupled to HPLC method described by Wang et al., Chromatographia, 44, 205–208(1997) or the affinity capillary electrophoresis method described by Busch et al., J. Chromatogr. 777: 311–328 (1997), the disclosures of which are incorporated herein by reference can be used.

The above procedures may also be applied to evaluate mutant PG1 proteins responsible for a detectable phenotype.

Production of Antibodies Against the PG1 Protein

The proteins expressed from the PG1 cDNA of SEQ ID NO: 3 (or a cDNA, recombinant DNA, or synthetic DNA encoding the protein of SEQ ID NO:5), cDNAs encoding mutant PG1 proteins responsible for a detectable phenotype, or portions thereof may be used to generate antibodies capable of specifically binding to the expressed PG1 protein or fragments thereof as described in Example 16 below. The antibodies may be capable of binding the full length protein encoded by the sequence of SEQ ID NO: 3 (i.e. the protein of SEQ ID NO:4), the full length protein of SEQ ID NO:5, or the full length protein encoded by a cDNA encoding a mutant PG1 protein responsible for a detectable phenotype. Alternatively, the antibodies may be capable of binding fragments of the PG1 protein which comprise at least 10 amino acids of the sequences of SEQ ID NO 4, SEQ ID NO:5, or a mutant PG1 protein responsible for a detectable phenotype. In some embodiments, the antibodies may be capable of binding fragments of the PG1 protein which comprise at least 15 amino acids of the sequences of SEQ ID NO 4, SEQ ID NO:5, or a mutant PG1 protein responsible for a detectable phenotype. In other embodiments, the antibodies may be capable of binding fragments of the PG1 protein which comprise at least 25 amino acids of the sequences of SEQ ID NO 4, SEQ ID NO:5, or a mutant PG1 protein responsible for a detectable phenotype. In further embodiments, the antibodies may be capable of binding fragments of the PG1 protein which comprise at least 40 amino acids of the sequences of SEQ ID NO 4, SEQ ID NO:5, or a mutant PG1 protein responsible for a detectable phenotype. Both monoclonal antibodies and polyclonal antibodies are within the scope of the present invention.

Antibodies may also be generated which are capable of specifically binding to a given isoform of the PG1 protein. For example, the antibodies may be capable of specifically binding to an isoform of the PG1 protein which causes prostate cancer or another detectable phenotype which has been obtained as described above and expressed from an expression vector as described above. Alternatively, the antibodies may be capable of binding to an isoform of the PG1 protein which does not cause prostate cancer. Such antibodies may be used in diagnostic assays in which protein samples from an individual are evaluated for the presence of an isoform of the PG1 protein which causes cancer or another detectable phenotype using techniques such as Western blotting or ELISA assays.

EXAMPLE 16

Substantially pure protein or polypeptide is isolated from transfected or transformed cells containing an expression vector encoding the PG1 protein or a portion thereof as described in Example 13. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the PG1 protein or a portion thereof can be prepared from murine hybridomas according to the classical method of Kohler, G. and Milstein, C., Nature 256: 495 (1975) or derivative methods thereof. Briefly, a mouse is repetitively inoculated with a few micrograms of the PG1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70: 419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogeneous epitopes in the PG1 protein or a portion thereof can be prepared by immunizing suitable animals with the PG1 protein or a portion thereof, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33: 988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Use of PG1 Nucleic Acids as Reagents

The PG1 genomic DNA of SEQ ID NO: 1, the PG1 cDNA of SEQ ID NO: 3, and PG1 alleles responsible for a detectable phenotype (such as those obtainable by the methods of Example 9 above) can be used to prepare PCR primers for use in diagnostic techniques or genetic engineering methods such as those described above. Example 17 below describes the use of the PG1 genomic DNA of SEQ ID NO: 1, th PG1 cDNA of SEQ ID NO: 3, and PG1 alleles responsible for a detectable phenotype (such as those obtainable by the methods of Example 9 above) in PCR amplification procedures.

EXAMPLE 17

The PG1 genomic DNA of SEQ ID NO: 1, the PG1 cDNA of SEQ ID NO: 3, and PG1 alleles responsible for a detectable phenotype (such as those obtainable by the methods of Example 9 above) may be used to prepare PCR primers for a variety of applications, including isolation procedures for cloning nucleic acids capable of hybridizing to such sequences, diagnostic techniques and forensic techniques. The PCR primers comprise at least 10 consecutive bases of the PG1 genomic DNA of SEQ ID NO: 1, the PG1 cDNA of SEQ ID NO: 3, and PG1 alleles responsible for a detectable phenotype (such as those obtainable by the methods of Example 9 above) or the sequences complementary thereto. Preferably, the PCR primers comprise at least 12, 15, or 17 consecutive bases of these sequences. More preferably, the PCR primers comprise at least 20–30 consecutive bases of the PG1 genomic DNA of SEQ ID NO: 1, the PG1 cDNA of SEQ ID NO: 3, and PG1 alleles responsible for a detectable phenotype (such as those obtainable by the methods of Example 9 above) or the sequences complementary thereto. In some embodiments, the PCR primers may comprise more than 30 consecutive bases of the PG1 genomic DNA of SEQ ID NO: 1, the PG1 cDNA of SEQ ID NO: 3, and PG1 alleles responsible for a detectable phenotype (such as those obtainable by the methods of Example 9 above) or the sequences complementary thereto. It is preferred that the primer pairs to be used together in a PCR amplification have approximately the same G/C ratio, so that melting temperatures are approximately the same. A variety of PCR techniques are familiar to those skilled in the art. For a review of PCR technology, see Molecular Cloning to Genetic Engineering White, B. A. Ed in Methods in Molecular Biology 67: Humana Press, Totowa 1997, the disclosure of which is incorporated herein by reference. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

Gene Therapy

The present invention also comprises the use of the PG1 genomic DNA sequence of SEQ ID NO: 1, the PG1 cDNA of SEQ ID NO: 3, or nucleic acid encoding a mutant PG1 protein responsible for a detectable phenotype in gene therapy strategies, including antisense and triple helix strategies as described in Examples 18 and 19 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 18

Preparation and Use of Antisense Oligonucleotides

The antisense nucleic acid molecules to be used in gene therapy may be either DNA or RNA sequences. They may comprise a sequence complementary to the sequence of the PG1 genomic DNA of SEQ ID NO: 1, the PG1 cDNA of SEQ ID NO: 3, or a nucleic acid encoding a PG1 protein responsible for a detectable phenoytpe. The antisense nucleic acids should have a length and melting temperature sufficient to permit formation of an intracellular duplex having sufficient stability to inhibit the expression of the PG1 mRNA in the duplex. Strategies for designing antisense nucleic acids suitable for use in gene therapy are disclosed in Green et al., Ann. Rev. Biochem. 55: 569–597 (1986) and Izant and Weintraub, Cell 36: 1007–1015 (1984), which are hereby incorporated herein by reference.

In some strategies, antisense molecules are obtained by reversing the orientation of the PG1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of PG1 antisense nucleic acids in vivo by operably linking DNA containing the antisense sequence to a promoter in an expression vector.

Alternatively, oligonucleotides which are complementary to the strand of the PG1 gene normally transcribed in the cell may be synthesized in vitro. Thus, the antisense PG1 nucleic acids are complementary to the PG1 mRNA and are capable of hybridizing to the mRNA to create a duplex. In some embodiments, the PG1 antisense sequences may contain modified sugar phosphate backbones to increase stability and make them less sensitive to RNase activity. Examples of modifications suitable for use in antisense strategies are described by Rossi et al., Pharmacol. Ther. 50(2): 245–254, (1991).

Various types of antisense oligonucleotides complementary to the sequence of the PG1 genomic DNA of SEQ ID NO: 1, the PG1 cDNA of SEQ ID NO: 3, or a nucleic acid encoding a PG1 protein responsible for a detectable phenoytpe may be used. In one preferred embodiment, stable and semi-stable antisense oligonucleotides as described in International Application No. PCT WO94/23026, hereby incorporated by reference, are used to inhibit the expression of the PG1 gene. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides described in International Application No. WO 95/04141, which is incorporated herein by reference, are used to inhibit expression of the PG1 gene.

In yet another preferred embodiment, the covalently cross-linked antisense oligonucleotides described in International Application No. WO 96/31523, hereby incorporated by reference, are used to inhibit expression of the PG1 gene. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used to inhibit the expression of the PG1 gene. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used to inhibit the expression of the PG1 gene. These ligated oligonucleotide "dumbbells" contain the binding site for a transcription factor which binds to the PG1 promoter and inhibits expression of the gene under control of the transcription factor by sequestering the factor.

Use of the closed antisense oligonucleotides disclosed in International Application No. WO 92/19732, which is incorporated by reference herein, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit PG1 gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The PG1 antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the PG1 antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, antibody-mediated tests such as RIAs and ELISA, functional assays, or radiolabeling are used to determine the effectiveness of antisense inhibition on PG1 expression.

The PG1 cDNA, the PG1 genomic DNA, and the PG1 alleles of the present invention may also be used in gene therapy approaches based on intracellular triple helix formation. Triple helix oligonucleotides are used to inhibit transcription from a genome. They are particularly useful for studying alterations in cell activity as it is associated with a particular gene. The PG1 cDNA, PG1 genomic DNA, or PG1 allele of the present invention or, more preferably, a portion of those sequences, can be used to inhibit gene expression in individuals suffering from prostate cancer or another detectable phenotype or individuals at risk for developing prostate cancer or another detectable phenotype at a later date as a result of their PG1 genotype. Similarly, a portion of the PG1 cDNA, the PG1 genomic DNA, or the PG1 alleles can be used to study the effect of inhibiting PG1 transcription within a cell. Traditionally, homopurine sequences were considered the most useful for triple helix strategies, such as those described in Example 19 below. However, homopyrimidine sequences can also inhibit gene expression. Such homopyrimidine oligonucleotides bind to the major groove at homopurine:homopyrimidine sequences. Thus, both types of sequences from the PG1 cDNA, the PG1 genomic DNA, and the PG1 alleles are contemplated within the scope of this invention.

EXAMPLE 19

The sequences of the PG1 cDNA, the PG1 genomic DNA, and the PG1 alleles are scanned to identify 10-mer to 20-mer homopyrimidine or homopurine stretches which could be used in triple-helix based strategies for inhibiting PG1 expression. Following identification of candidate homopyrimidine or homopurine stretches, their efficiency in inhibiting PG1 expression is assessed by introducing varying amounts of oligonucleotides containing the candidate sequences into tissue culture cells which express the PG1 gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced PG1 expression using techniques such as Northern blotting, RNase protection assays, or PCR based strategies to monitor the transcription levels of the PG1 gene in cells which have been treated with the oligonucleotide.

The oligonucleotides which are effective in inhibiting gene expression in tissue culture cells may then be introduced in vivo using the techniques described above and in Example 18 at a dosage calculated based on the in vitro results, as described in Example 18.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245: 967–971 (1989), which is hereby incorporated by this reference).

Alternatively, the PG1 cDNA, the PG1 genomic DNA, and the PG1 alleles of the present invention may be used in gene therapy approaches in which expression of the PG1 protein is beneficial, as described in Example 20 below.

EXAMPLE 20

The PG1 cDNA, the PG1 genomic DNA, and the PG1 alleles of the present invention may also be used to express the PG1 protein or a portion thereof in a host organism to produce a beneficial effect. In such procedures, the PG1 protein may be transiently expressed in the host organism or stably expressed in the host organism. The expressed PG1 protein may be used to treat conditions resulting from a lack of PG1 expression or conditions in which augmentation of existing levels of PG1 expression is beneficial.

A nucleic acid encoding the PG1 proteins of SEQ ID NO: 4, SEQ ID NO:5, or a PG1 allele is introduced into the host organism. The nucleic acid may be introduced into the host organism using a variety of techniques known to those of skill in the art. For example, the nucleic acid may be injected into the host organism as naked DNA such that the encoded PG1 protein is expressed in the host organism, thereby producing a beneficial effect.

Alternatively, the nucleic acid encoding the PG1 proteins of SEQ ID NO: 4, SEQ ID NO: 5, or a PG1 allele may be cloned into an expression vector downstream of a promoter which is active in the host organism. The expression vector may be any of the expression vectors designed for use in gene therapy, including viral or retroviral vectors.

The expression vector may be directly introduced into the host organism such that the PG1 protein is expressed in the host organism to produce a beneficial effect. In another approach, the expression vector may be introduced into cells in vitro. Cells containing the expression vector are thereafter selected and introduced into the host organism, where they express the PG1 protein to produce a beneficial effect.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE 1

| marker | polymorphis | most frequent | less frequent | cases p* | q** | p* | q** |
|---|---|---|---|---|---|---|---|
| 99-123 | C/T | C | T | 0.65 | 0.35 | 0.7 | 0.3 |
| 4-26 | A/G | A | G | 0.61 | 0.39 | 0.55 | 0.45 |
| 4-14 | C/T | C | T | 0.65 | 0.35 | 0.59 | 0.41 |
| 4-77 | C/G | C | G | 0.67 | 0.33 | 0.76 | 0.24 |
| 99-217 | C/T | C | T | 0.69 | 0.31 | 0.77 | 0.23 |
| 4-67 | C/T | C | T | 0.74 | 0.26 | 0.84 | 0.16 |
| 99-213 | A/G | A | G | 0.55 | 0.45 | 0.62 | 0.38 |
| 99-221 | C/A | C | A | 0.43 | 0.57 | 0.43 | 0.57 |
| 99-135 | A/G | A | G | 0.75 | 0.25 | 0.7 | 0.3 |

*frequency of most frequent base within each sub-population
**frequency of least frequent base within each sub-population (p + q = 1)
standard deviations ~0,023 to 0,031 for controls
standard deviations ~0,018 to 0,021 for cases

What is claimed is:

1. A purified or isolated nucleic acid comprising the sequence of SEQ ID NO: 1 or the sequence complementary thereto.

2. A purified or isolated nucleic acid comprising the sequence of nucleotides 1629 through 1870 of the sequence of SEQ ID NO: 1.

3. A purified or isolated nucleic acid comprising the sequence of SEQ ID NO: 3 or the sequence complementary thereto.

4. A purified or isolated nucleic acid encoding the polypeptide of SEQ ID NO: 4.

5. A host cell containing the nucleic acid of claim 1.

6. A host cell containing the nucleic acid of claim 3.

7. A purified or isolated nucleic acid encoding the protein of SEQ ID NO: 5.

* * * * *

SEQUENCE LISTING (1) GENERAL INFORMATION:

(iii) NUMBER OF SEQUENCES: 68

(2) INFORMATION FOR SEQ ID NO: 1:

(i) SEQUENCE CHARACTERISTICS:
      (A) LENGTH: 56516 base pairs
      (B) TYPE: NUCLEIC ACID
      (C) STRANDEDNESS: DOUBLE
      (D) TOPOLOGY: LINEAR (ii) MOLECULE TYPE: GENOMIC DNA (vi) ORIGINAL SOURCE:
      (A) ORGANISM: Homo sapiens (ix) FEATURE:
      (A) NAME/KEY: Promoter
      (B) LOCATION: 1629..1870
      (C) IDENTIFICATION METHOD: Proscan (ix) FEATURE:
      (A) NAME/KEY: Potential ATG
      (B) LOCATION: 1998..2000

(ix) FEATURE:
      (A) NAME/KEY: Exon 1
      (B) LOCATION: 2001..2216

(ix) FEATURE:
      (A) NAME/KEY: ATG
      (B) LOCATION: 2031..2033

(ix) FEATURE:
      (A) NAME/KEY: TYR phos
      (B) LOCATION: 11694..14332

(ix) FEATURE:
      (A) NAME/KEY: SEQ ID42
      (B) LOCATION: 11930..11947

(ix) FEATURE:
      (A) NAME/KEY: SEQ ID24

-continued (B) LOCATION: 12057..12103

(ix) FEATURE:
         (A) NAME/KEY: SEQ ID51
         (B) LOCATION: compl(12339..12358)

(ix) FEATURE:
         (A) NAME/KEY: SEQ ID64
         (B) LOCATION: 13547..13564

(ix) FEATURE:
         (A) NAME/KEY: SEQ ID58
         (B) LOCATION: 13657..13703

(ix) FEATURE:
         (A) NAME/KEY: SEQ ID67
         (B) LOCATION: compl(13962..13981)

(ix) FEATURE:
         (A) NAME/KEY: Exon 2
         (B) LOCATION: 18196..18265

(ix) FEATURE:
         (A) NAME/KEY: Exon 3
         (B) LOCATION: 23717..23832

(ix) FEATURE:
         (A) NAME/KEY: Exon 4
         (B) LOCATION: 25571..25660

(ix) FEATURE:
         (A) NAME/KEY: SEQ ID43
         (B) LOCATION: 34216..34234

(ix) FEATURE:
         (A) NAME/KEY: SEQ ID25
         (B) LOCATION: 34469..34515

(ix) FEATURE:
         (A) NAME/KEY: SEQ ID52
         (B) LOCATION: compl(34625..34645)

(ix) FEATURE:
         (A) NAME/KEY: Exon 5
         (B) LOCATION: 34669..34759

(ix) FEATURE:
         (A) NAME/KEY: Exon 6
         (B) LOCATION: 40688..40846

(ix) FEATURE:
         (A) NAME/KEY: Exon 7
         (B) LOCATION: 48070..48193

(ix) FEATURE:
         (A) NAME/KEY: Exon 8
         (B) LOCATION: 50182..54523

(ix) FEATURE:
         (A) NAME/KEY: SEQ ID65
         (B) LOCATION: 51149..51168

(ix) FEATURE:
         (A) NAME/KEY: SEQ ID59
         (B) LOCATION: 51448..51494

(ix) FEATURE:
         (A) NAME/KEY: SEQ ID68
         (B) LOCATION: compl(51482..51499)

(ix) FEATURE:
         (A) NAME/KEY: SEQ ID44
         (B) LOCATION: 51596..51613

(ix) FEATURE:
         (A) NAME/KEY: SEQ ID26
         (B) LOCATION: 51612..51658

(ix) FEATURE:
         (A) NAME/KEY: SEQ ID53

(B) LOCATION: compl(51996..52015)

(ix) FEATURE:
(A) NAME/KEY: polyAd signal
(B) LOCATION: 54445..54450

(xi) SEQUENCE DESCRIPTION: SEQ ID NO: 1:

```
GTGGATCTGT GACTGTTCGC AGGAAGAGAG GAGCGGGAGC AGGACAGACA ATAACTGATA    60

GTCAGGAGCT GGGTTTGGAG ATAAAGAGGG AACAAGAGAA AGTTAAGTTC TGTGTTTTCA   120

TGGCAAACAT TGCACAAAAG TTTACAACTT CGTGACTAAC AGTAATCTGG GGTGATTCAC   180

AACAAATTTA CACATAAACA CATATTTACT GACTTTATAC ACAGCAATCC TAACGTGAAC   240

ACAGAACCTG CTTTATCTTT TCGCACACTG TTCTAGTGTA GAGATGTCTG GTCTCAGTTA   300

AAGAAAGCAT AAGGAGCATT AGTTGTGCAC ACTGTCCACA CCCGTGACTT TTTTCCACCA   360

GTACTAAACC TAGTGCTTCT TACAGTACAG GGCAATGACA GCCACAGAAA GAGAGAAGCT   420

CCTTTTACTG TGTAATGCTT CCTGCTGGCC TTCAAATACT TGTTACTTGA GAGATCTCCA   480

TTCACCTGGC TTTGTCCCCA AAGGTCATCA TCTACCAATG ATGTTGTTAT TTGATGTTAA   540

TCATGTATAA AGAAAGTAGC TACCATCCTG GCCCTGATTA GAACTTCCCA CTGAAATACC   600

GTCCTGCCTA AAGGTAGCAC AGGTTTCCAT TATGGTGGTG GTGGGGAGGG GGCGGGAATA   660

TATATATATA TATATATATA TATATATATG GTAAAGCATT CGGCATTCTT TTAAAGTACA   720

ACTATCCTTG AAAAGGGTTA CATATTAAAC CATTTTTACC ACAGCCAAAG GGGAGGAGAA   780

AGATCCAAAA GTCCTGTGGA TCTGCTTTAA CATCAATAAA ACAGTTATCC ACCCTTCGTA   840

GCTTTTAGTG AAGGCTACAA AAGTATGCTT TTTATGGATT ACACATGTGC ACGCAACTAC   900

TTTAATTACT ACAGAAAAAA ACGAGGCTCC TTATTAAAAA AAAATCAGAA ACAAGTCCAA   960

CAGACTCTGA GGAAATGAAG CAAGAGTGAA TTCTGAAAAG GTCTAATAAA CAGTATGGAA  1020

ATATCCTTGT GGGATTGTTC TTCAGCTATG CATAAACATG TAATTATCAT CATTACTGTG  1080

ATGGGGAAAA ACACGGACCC TAATTCTGAA ACACCCTGGT AGCGAGAGAC GGGCAGGAGG  1140

GGCTGCTGCG CACTCAGAGC GGAGGCTGAG GAGGCGGCGT CCCCTTGCAA AGGACTGGCA  1200

GTGAGCAGAT GGGGACACTC GAGCTGCCCC GCGACCTGGG CCGAGCTGCC TACAACCTGG  1260

GCCCAGGTGC CTGCAAGAAT TAGACCTCCG ATAACGTTAA CACCCACTTT CTCACTGCTC  1320

TAATTGTGTG CATCCCGGCG CCCAGGGGCT TGTGAGCAGC AGGTGCGCGT TCCAGGCAGC  1380

TCCAGCGACC CTTAAACCTG ACCGCGCGCA CGTCCGGCCC GAGGGAGCAG AACAAGAGGC  1440

ACCCGGACCC TCCTCCGGCC AGCACCCACC TTCACCCAGT TCCGTCAGTC GCCACCACCT  1500

CCCTTCCCGC GTCCGCAGCC GGCCCAGCTG GGGAGCATGC GCAGTGGCCG GAGCCGGGTT  1560

GCCCGCGCCA CAGCAGGTAG CTGTACTGCA ACTGTCGGCC CAAACCAACC AATCAAGAGA  1620

CGTGTTATTG CCGCCGAGGT GGAACTATGG CAACGGGCGA CCAATCAGAA GGCGCGTTGT  1680

TGCCGCGGAG CCCCCTGCCC CGGCAGGGGG ATGTGGCGAT GGGTGAGGGT CATGGGGTGT  1740

GAGCATCCCT GAGCCATCGA TCCGGGAGGG CCGCGGGTTC CCTTGCTTTG CCGCCGGGAG  1800

CGGCGCACGC AGCCCCGCAC TCGCCTACCC GGCCCCGGGC GGCGGCGCGG CCCATGCGGC  1860

TGGGGGCGGA GGCTGGGAGC GGGTGGCGGG CGCGGCGGCC CGGGCCCGGG CGGTGATTGG  1920

CCGCCTGCTG GCCGCGACTG AGGCCCGGGA GGCGGGCGGG GAGCGCAGGC GGAGCTCGCT  1980

GCCGCCGAGC TGAGAAGATG CTGCTGTCCC TGGTGCTCCA CACGTACTCC ATGCGCTACC  2040

TGCTGCCCAG CGTCGTGCTC CTGGGCACGG CGCCCACCTA CGTGTTGGCC TGGGGGGTCT  2100

GGCGGCTGCT CTCCGCCTTC CTGCCCGCCC GCTTCTACCA AGCGCTGGAC GACCGGCTGT  2160
```

```
ACTGCGTCTA CCAGAGCATG GTGCTCTTCT TCTTCGAGAA TTACACCGGG GTCCAGGTGA   2220
GCCGCCTCCC GCTCCCGGGT CTCGGCGTCC ACCCGAGCTC CCGGGGCGC GGACCTCTCC    2280
GCTCCCCCAC AGCTGGCGAG GGTCACCCGG CCGGCCCGGC GGACCCAGCA CGGAGAGCAC   2340
GTGCCGCCTC CCCGCCTTCC TCTCCGCATG CTTCCTGCCG TTCTGCCGAG ATCGCTCTCT   2400
AGGAAGCTGT GGCTGCGTCG TCCTGAGGCT ACGAGTGGGA CCCGCCGCCC CTTTCCCCGC   2460
CCCTCGCCTG GGTCTGATGC TGCTTAGCAA AGTGGGTGCA GATGCACGTT TTAAATAATA   2520
GGGCACGCGT TTAGCAGTTT CTGGCCTTTG GTCCAAAGAG GTGGTCATGT TGGAACAGAT   2580
CGGAGACGTC TACACTCCGA AGTGCGCTTT TACAGTGACC TCTTGAAACA GAAGTACAAT   2640
TCGGTCTTGT GTTCTTTCCC CTGGACAAGT GAAAGCTGGG CGAAGAAATG AATACATTTG   2700
TTAACCGTAG AAGCCTAACT AGATACAATT CTTGCCAACT TAACTGGGC TTGAATGTGT    2760
GGGTGATCTG TTGTCTGATT ACTTTCTTTC TGTTACTGTT TCTCTGTAGA GATTGGATTC   2820
GTAGATTAAA CTTGAGAAAC AAACCATAAA AGTGGAAGGC CCTCTTTAAC AGTAGGTATT   2880
TGAAGTGTTA TAAAAAAAAA AAAGGTGAAT TTTTCTTTTA TTTCTCAGTT TGAAAGAACA   2940
GCTTTATTCT TGGTTATTCC TAATGTCCAC CTAGTCCTCT TTTACTTTTC TTGGTAGGGT   3000
TAGGGTGGCA TGGGGAAATG GGACGGTATC ATTTTGTCTT TTTAACTTTT TTTTTTTCCA   3060
CCTACAGCAG CTGTTTTTAC CCTGTGGTCA GTCAGGTACT ATATTTAGTT TGCAGTTGCA   3120
CTGCTGATCG ACCCTTGATG GCCCCAGTTG GAAGTTGTTT GGGGGGAAGG AACTAGGAGA   3180
GGCCAGGGCC TCCATTTAAA CCAGTGTCTG TAAGTGTCTC CTTGGAAGGA AAAAAAGATA   3240
CTGTTCCAGG TCATGGTTTC CTGGTAGTTG ACGTTTAAAA TGGGCCTCAT TTAAAAATTT   3300
CAATAATTCA GGCTAATTTT TTCCCTTTAT ATGGTAACTC CACCAAGTTT GTCTAAATGT   3360
ATGATTTTTA TCATGATTAA GTTTTACTTT CCACATCATG TGACAACTGG CCTGGGATGG   3420
GATATAAGCT CAGAACACAA AGTCATTCAC CTGTTAAAAA AATAATTCTA TCTGTGGCGG   3480
GTTATGTTAT TTTTGTTCAA AGAGGACACA ATATGATGCA GAATACACCA TTGAAGGATT   3540
TTTTGGTTTG GCAAGTTCTT ATTTTTTTAA ATGGCTGTAA AACCTAGCAG TGTTTCTGAA   3600
ATTGCATACC TTACCTGATG TTCAGAGATC CGATTTACTT CTTGATTTCC CAGCAAGTGA   3660
TTTTGAAAAC ATTTAATCTA ATCATTCCCC CCACCGTCTG TTCAAATCAA AGGAAGTGGC   3720
ATCCAGCACT AATTTTCATG CATTTATGAA AGGATGCCTG AGGACCCTTA AGTATAATTC   3780
AAAATTTTGT TTAATGTGTG TTCCTTGATG AAGTTCTTTA GGAGTCGTAG AACGAACTGA   3840
TTGCCCACTG ATCATCAAAT GCAAGTTATG AACATTTAAT AAAAATTTAA AACCAAGAGT   3900
TTCTTGTTCC TGCATTTTTA TTTTTATTGT ATGGAGGGGA CAAATAATTA TTTTCTGTTT   3960
AGTAACAGAG CAGGGTATTT TGAATTTATT AGGGTCTTTT TCTGCAGTCT GGGTTTCCTG   4020
TGTACACAAA GCTACCTTTC AATATTTTTT ATTGTTTCTG TTAAGATTAA ATCAATAGAG   4080
GAATAAATAG CTATCTTCAA ACATAAGACC CAAAGGAAAA AGATTTATAG TGATGTTCTG   4140
TCACCTTATT TTTTACCTGT GACTTTGTAC CATTAACTTT GTCACTGAGA TGTTTTGATT   4200
AAAATTTTTA GCTTGCTTTT CTTGTTTTGT TAGGACACTC TTTTTTTCTT GAATTGTTTT   4260
TATCAGCTTT CGTTTGCAAG GCTAGTGATG ATTCTCTTGT TCTGTATAAA GTATTGTTGA   4320
CTCATTTCTG AAGGGAGTTT TAGTAATTTA AGAGGTTATA AGTTTTTAAA TAAAAGGTTT   4380
ATTAATTTAT ATATATTAAA GAGGCATTTT AAAATAAAAT TTTTTTTAAA TGACATTTTT   4440
ACACCTTTCA ACTCTAGGTT TAAAAAATAA GTGGTTCACA GTAGTTCTTG CAGAAGAATA   4500
TTTTCTTTTA CATAGAATTT TTAAGCTGAA GAGAAGTAGT AGTAGGTCCA TGAGATTTAT   4560
```

```
GATCTGTGCT TGGCAGGTAA ACCTGCTTCC AACAAATTTA GTTGGATTTT TCTTGGATTC       4620

TGGGTAAATA CCTTTTTCTT CCCCAGTTTC ACTACTTTAT TTTCATATGT ATCTCTGAGA       4680

TAGAGAAATA TTTCAGTCAG TGCTGCTAAA ATTGTTCCTT ATAACTCGTT TATCCTTTTA       4740

GGTCCTTCCA GAATCTCTCA TTGGTACTGA AACTCAAATG GGTACTTTCT TCACCATTTA       4800

TTTCTTTAGA ATAAGTAATA AGAATTTTAT AAGCTTTTTT ATATTTCACG TAATTTGAGA       4860

CTATTGAAAA TCCAGTTAAG TCTCTCTACT GTGTTGAGAG GCATTGATTC AAGTACCTGT       4920

GTTACTTTCC TGTGCTGCCA AAACAGATCA CCTCAAACTA AGCGGCTTAA AATAATAGAA       4980

CTTAAGTTCT CGTGATTCTG GAGGCCAGCA CTTTGAAATC AAGGTGTAGG CTCAATTTTA       5040

CTCCCTCTGG AGGCCCTAGG GGGAATCTGT TCTTGTGGGT TTCAACTTCT GGTGACTGGT       5100

GGCATTCCTT GGCTTGGGGC CCCATCACTT CAACCTCTGC CTTACAGTCC TTGCTGCCAC       5160

CTCTTCTGTC TCACATCTCA CTCTCCCTTT CTCTTAGAAG GATGCTTGTC ATTGGGTTTA       5220

GAGCCCACCT GGATATTCCG GGATGATCTC TTCATCTCAA GATCCTTAAT TATAACTGCA       5280

AAGAGCCTTT TTCCAAATAA GAAAACATTC ACAGGTTCCA GGGCTTAGGA TGTGGACACA       5340

TTTTTTGAGG GGCTGCCCTT CATTCCCCCA CAACAATGAA CTCCATAGTT CTGCCTATTC       5400

AGTATTTTGT AGTTATTTCG TAGTTTAACT TGCCTTATTT CTTTAGGTAT TTACGTATTA       5460

AAGCATTTTG GTCTCTGCTT TCTTTAACAG AGAACCTGGT TTTCTGTAAT AAGTTTACTT       5520

ACTTTCCCAT AATCTTTTAG TTTCTTATTT ACAGATTTAC CTTCACATAT CCCTTAAGTA       5580

GAACATTTGA TTAACTGTTT TATTTTCGGA ACAAATCTGC ATTCTGTATA ATAACCAACT       5640

TATTCATATT TCGGTATTCT TTTAATTCTT ATCTGATTCT GAAATTACCA TCTTGTGATT       5700

ATATATATAT ATATATGGAA ATAACTGAAA TCTTGATAAA TTAAAGGTGA TATAACTTCT       5760

AAGACAATTA ATTATGTATG ATGTGGTGAA TATACTGGTG TTTGGTTTGT TTGCCACTTA       5820

AAAGCCCTAT CTATAGGATA GGAAGTAACT TGAATGTGGA ATGCTTAGAG ACTCAGAGTA       5880

AGAGGCCGTA TATATATCCT TGAGCTGGAG TTTAAGGAAA ACTTATGGGA AATTAAAAGG       5940

AAAGTTGGAG TACTGACAGA GGATTGCGTA GGACTCATGA AAAAGGAATG AAGTTACCTT       6000

AAATTCTATC ATCGTGAGTT AACGTGAAAC TAGATTTATG TTAGTTTATA GCCTAGAATT       6060

CTATCCTAGG AATCTAGATA TATCCTAAAT GTTGAGATAG CTGCATAAAC AATAACTGTA       6120

ATCGTTATGA TAAATAATGA CAAATCTTTT TAGCATGTTT TGTGAAGCTG ATAAATGTTA       6180

ATAGGATGTC TTCAAATGTC AGAATTCTTT TTTCTTTGCT TCTTTTTTAA AAAATTTCTT       6240

TTCCCCCATT CCTATGCAAT ACACTGAAAA CTGATCATTG AAATTTGTAG GCCAAAAAAT       6300

TAATCAACAC GTAATAGATT GGGGTTTGGG TTTTTTTGAG TCAGGGTCTT CTTCTGTCAC       6360

CCAGGCTCTG GTGCGGTGGC ACCATCATGG CTCATTGCAG CCTTGAATGC CTGGGTTCAA       6420

GTGATCCTCC GGAGTAGCTG CCGTGCCATT ATTTCTAGCT AATTTTTAAA AGTTTTTGTA       6480

GAAATGGGGT CTTTCTGTGT TGCCCAGGCT GGTCTTGAAT TCCTGGCCTC AGGTGATCCT       6540

TCTGCCTTGG CCTCCCAAAG TGCTGGGATT ACAGGTGTGA GCCACCATGC CTAGCCCCTA       6600

ATAAATATTC TAATTACCGA TTTATCTTGC TTAAATCAGT TGGTAACACT TGGAATTTAC       6660

TTCAGAATAT ATTTTACATT AGTGGCTCTG ACTGCTAATT CCCCCTTCTC CAAATGCTAA       6720

TGTAATATAA CAATAAAATG CACAGTTCTT AAGTTTATAT AAAATAAACA GGTTTTCAGT       6780

TGACCTGCTT TAAGTGTAAA ATAGTGTGAA AAACACAAGA AAGAAGATAA AGAATTTAAG       6840

ATTTTGACAT TTCTCTAATA TGCCCTTAAC TTCTCCAAGG ATTCATACTT TTTTTTGTAA       6900

GACAGAATCT CACACTGTTG CCCAAACCAG AGGTGCAGTG GTGCAGTCTC CACTCACTGC       6960
```

```
AACCTCTGCC CCCGGGCTCA AGCGGTCCTC CCACCTCAGC CTCCTGAGTA GCTGGGACTA      7020

CAGGTACACA GCACCATGCC CAGCTAATTT TTTTTTTTGG TATTTTTTAG TGGGGGTAGA      7080

GACGAGATTT TGCCATATTG CCCAGTCTGG TTTTGAGCTC CTGGGCTCAA GTGATCCGTC      7140

CTTGATCCAC CATGCTTAGC TGATTCATAC TCTTAACTGA AACATTGTTC CAAGTTTCTC      7200

AGAAACAGTC AAGGCTTTTT ATCTAGAGAA CATTTATAAC TGGATCTTTC TTTGTGTAGC      7260

ACTGATTCAT CAAACTAATC CTAAACTCCT AATGAGTTAA ATTTATATTC TGAATCTTGC      7320

TGTAAAAGCA GCCATTCATT AGAATGAAAC ATGTTTACTT AGAATTGGAG AAGGGAGCTT      7380

ATAAGTCATC TAGTCTACTC CCTTTTATGA CACTTCTACA TTCTTTCTGC ACTTCTGCCA      7440

AAATGTTGCC CAGCGTCGTC TCTGATACCT ATAGTCCTAA CAAGAATATG AATCATACCT      7500

TGTATCCTTA ATTTTACTCT TCTCTGCTTA TTTGCCATTC ATGTGAAGAC CTTAAATAGA      7560

TCTTAAATTG CTTCCTTCAC TTTAGCTGAG AGTGACAGGA CTGTGTAGGT GTGGGTGTGT      7620

TTCTGCATTT GCTTATTTAA GCAGGATAAT AAAAACTTTT ACTATAGGAA ATTAAACATT      7680

TCCCAATCAA ATACAATTCC AGTCTAACAC AATTAAATTC TGGTTAGGGA ACTGCTTAAC      7740

TTACTAGACT TATAGGAAAA TACTAAAAAA ATGTAACTAG AACTCTATTT TTACACTTTA      7800

TAAATATAAA CCTCTGTGAA CAAACCAGTT ATTTCAGGTT GCATTTGTGT ATAGTTTTTT      7860

AATGCCTGAT TTTTCTATTT TAAAATCACA GATGCAATTA TACATTCAAA CACTGCCACA      7920

ATACTTTGAG AAAGTTAAAG TTTCCCCTAC TCCTACACTG CGTACACCTT TCCTAGGTAC      7980

ATCCCAGTTT GGTGTGTAAC TTTAGATTTC TTCCAAGAGC TTTTGAGTAA GTGTTTGAAT      8040

TGTGGGAAGG TTCTTTAGTT AAATGAACTT CTTACAGATC AGTTTTTTAG TACAGTAGCA      8100

CGAAATATAC CTGCATACCT ATGGGGATAC CTCTGTGCCA TTACGATGGA AGGCACGGGA      8160

AAACAGCACT CCGTATATAC CTAGTTTACT TTCCCTCTTT TGTATATTTG TCTGATTTTG      8220

TGGAGCTGAT GCTTCTCAAG TGGAATCAGA AGTTAACTTT TCCTTTACTA TTTTCTCATT      8280

TTATTATGGT TTCTTAACTA GAGGTTGATG TTAGTGGTTG GACCATTCAA TAGTAAGTAA      8340

TGACTTTTCA GTAAGGGATC TCTAGAACCC AGATCCCTTA ATTCCTGCAA TATTCCCGTG      8400

TGTACATTGT TCCAGGTGCT GTCCTGGGTA CCAAGGGATA CAATGTTTGA TAGACAATGT      8460

ACCTGCCATT ATGGAGGTCA CATTCTAGTG TGGGAAGACA AACAATAACA AGAAAATGAA      8520

AATTTACTGT GCCATGCCAG GTTGTTTAGC CTGGTGGGTG AGAGGTAGGG GTTTGGAAAA      8580

TCTTACTGAG CAAGTGACAT TTGTGTGGAG CTCTGTAAAA GGGCCAGCTT GGAAGGTAAT      8640

GTAGTCATCC AGGTGAGAAA TGATGGTTAG GGGAGTGGAA AGAGTGGATG TTAAGATTGA      8700

AAAGAATTCC AAATCTATTT TAGTGGTAGC TGATAGGGCT TTGTGATTGA ATGTGGAGGA      8760

AAAAGAAGAG GGTGGGTTAG TAACACACTC AGTCGCAGTT AGTGAGTGCT GCTGTGTGCA      8820

AGTATTGTTC TATTATGTAA ATAATTCCAT CTTTACAAAG TAGGCACCAT TCTTCCTCTT      8880

TTACAGACAA GGAAAAGGGA ACACCCATGG TTCACATCTG TAGTAGCCTA GCCAGGAGTT      8940

TCAGGCACTT ATTTTCTGAA GATGCTCTGC CTGGCAATGT GGTTATATTG GTTGAAATGA      9000

GACCCCCTAC TTTCAAGGTA TTCATCTAGG AAAGACATGA ACTGCCAATT ACAATATAGG      9060

ATAACACTGA AATTAGAGAC GTGTTTATTA ACTTTGCCAT ACAGAGGTAA AGTAACTCTT      9120

TAAAGTAACT CTTTGCTTGG GTTAGTGGAG AAGGCTATAA AAATTACTTG GAGTTTTTAC      9180

TTTGAACATG CGTAATTAAC ATGGAATGTT TAGGGAAAAG AGGTTTTCAA TTGATAACAT      9240

AATAAACATG AGGAGTTTGA AGCATGGCAT TCAAGGTTTT CTAAATTCTG CCCCGGTTAA      9300

CTTTTCCATT CGTTGGTTTC ATTCTAGTCT AGCTTTTCCT TCTGGGCCGC CCCTCCCCAC      9360
```

| | |
|---|---|
| ATTAGACCGC TCCTCTCTGG AATTCCAACT CAAGCCCTTG CTTTTCTCCA TCTGTCATGA | 9420 |
| TGTTACCCCA TCTCATTGTC AGGGTAACTT TTATGTAATA TTAACATATA TAATACTGAT | 9480 |
| ATAACATTAG CATATTTTAA TGTATGGATC ATCTCCTCTG CAACATTGTA ACCTCTTGGA | 9540 |
| GATGGCAATA ATGGGAAGAA TGACTTGATT TTACTTTTTC TTTTAACAAA AATGGTGGAG | 9600 |
| TAGTCTGGGC ACGGTGTGGC TCATGCCTGT AATCCCAGCA TTTTGGGAGG CCAAGGAGGG | 9660 |
| TGGATCACTT GAGGTCAGGC ATTCGAGACC AGTCTGGCCA ACATTGTGAA ACCCCATCTC | 9720 |
| TACCAAAAAA ATACAAACAC TTACTGGGCA TGGTGGTGTG TGCCTGTAGT CCTAGCTACT | 9780 |
| CAGGAGGCTG AGGTGGGAGA ATCACTTGAA CATGGGAGGT AGAGGCTCCA GCTTGGGCGA | 9840 |
| CAGAGTGAGA CCCTGTCTCA AAAGAAAAAA AAGGTAAAAG GGCCAGGTGC GGAGGCTCAC | 9900 |
| GCTGGTAATC CAAGCACTTT GGGAGGCTGA GGCAATGGAT CACCTGAGGT CGGGAGTTCG | 9960 |
| AGATCAGCCT GACCAACATG GAGAAACCCC TTCTCTACTA AAAATACAAA ATTAGCCGGG | 10020 |
| CGTGGTGGTG CCTGCCTGTA ATCTAAGCTA CATGGGAGGC TGAGGCAGGA GAATCACTTG | 10080 |
| AACCCAGGAG ACAGAGGTTG TGGTGAGCCA AGATGGCACC ATTGCACTCC CGACTGGGCA | 10140 |
| ACAAGAGCGA AATTCCGTCT CAAAACAAAC AAACAAACAA AACAAACAG AGAGAAAAGG | 10200 |
| CAGAGTACTC TAGGGAATTC TAGTCTGTGT TTCTGTGGAA ATGTATATGA ATCTCACTTT | 10260 |
| TAAGGGATGG AGATTTTTGA ATGGCATAAC TAGTTGATAA GTTTTGCTCT AACAGGGTAC | 10320 |
| CCAAGTCTAG TGAGTCCGAT TCATTCTTTC CTTAAATAGA TGAAGGAGGA AGAAACATGA | 10380 |
| CTCCACCCTC AAGAGTAAGG CAGAATGAGC AAAGTCAGAG AAGTTAAAAA AGAATTCTCA | 10440 |
| CGCAGCCAGC AGTGCAGAGA AACCTTGGTT TAGTTGTGAA TCAAAACCAG TACTTTTGT | 10500 |
| AATTTTTGAG CCTATGCAAT TCTCCAAGGT TTTATGTTGT TTCTTCTGTT TCTCTGTAGG | 10560 |
| CACCAGAAAT CAAAACCCCA AATAAGAAAG TGTTACTTGA AGATTTTAGA GTACTTATTT | 10620 |
| GTGTATAAGT GTAAGTGATA TTTGAAGAC GACTTTACTG CGCTCCTCCA GCTTGGCATG | 10680 |
| AGAATTCCAG GGGCGGAAAG AAAGGAGGGT GATGGTACCT GGAAAGGAGA GTCATGTTAA | 10740 |
| GTCCCAGCCA CATATTAAGT GCTAACCACC TACTGTTAAA AGGTGTAATG TTCTAGACTG | 10800 |
| ACAAAATACA TAGTCTCTAC CGTAAAGTAA CACATAATTT AGCAGTGCAG AAAGATGTCA | 10860 |
| CTTAAAAGAA AACTTGAATA TATGCTGAGA TAGTTCACAA ATTAAAGAAA TGAACAAAGA | 10920 |
| ACTGAGGAAA TAAAGGAGGA ATACAACTGT GTCCAAATGA ATACTTAACT GGGTGGGAGC | 10980 |
| TGTTGCATAT GTAAGCAGGT GGTTCACCTA AAAGTTGGAT GTAACGTAGT TAACGCCAGC | 11040 |
| TCTTGGTGCA CTTACATATT GCATTGCTTC CGGGCTTAAT TTGTGTTCAT ATAGGAATAA | 11100 |
| ATTTTTTGTT GGTTTTTAAT TTTACTCCTT GTAATTCCGT GGTTGATATT CAAAGTGAAA | 11160 |
| AAAATTACAT AAGCTTCTAA TATATGAGAA GTCTTCTCAC TTGACATTTT TTATTTGGAA | 11220 |
| TTTTTGCAGA GAGTAGTTTT GTCACAGTCA AAAGATTTTG GGATCTTGCA GTGAGAAACC | 11280 |
| TAGGTGTAAT TCCTATTTCT CTGCCATTCC GTATGTCATC TGGATTAAGT GTCAACTTCT | 11340 |
| CAGTCTCAAG ATTCTCGTCC TTAAATGGAA TACTTTTTGT CATGCTATTT TGAAGACAAA | 11400 |
| ATGAGATAAT ACGTGAAACT GCCTAGCTCA GTGAATGGTA CATCATAGAT ACTCAGAAAA | 11460 |
| AACACACCCT CTAAAATAAG AACAGTACCA AAAGACAGGA TGTAAAATAA GGGCAGTACC | 11520 |
| AAAAGACACA TGCATGCTGA GTGTATGAGA AAGAACTTTG TGGCCTTCTT GGGTGGCACA | 11580 |
| GGCCATGGCA GTTCCACAGC ATGACGTGGT TGCTGTGGGT GGTAGAGCAG ACATGCCGCT | 11640 |
| CCCCGTCACT GCCTGGCTTT GATGCTTGCT TTCTTCAGCT GAGAGGACGC AGCTGTGATA | 11700 |
| TGAAGGTCTT GTGTGTACAG TCGTGACCTC ACATTTCCAA TTTCCTGCTG GCAGAACCCA | 11760 |

```
CAGTCTACAA CGTACGAGCA CCAGAGTTGA CGTGAGACAG ACAGCATACA GAGGCTTGTA    11820

ACATCCTTCT GGAAAACACT GTGTAAGCTT TCAGTGCGAA TAAACATGAT CAGTGGCAAG    11880

TTCTGTTAGA TGTAGTCTGC AAGCATCCTG ATTTTACTGG GCAAGACTAT GTTGATTTAC    11940

AGGCGGCTGA TGATTCCATG GATAGCCCAC TACTAGTATT TTCACAAATT TCACAAGACA    12000

TTCTTACTGG AAGATTGCCC TGTTCTTATG ATACTGCTGC CCTTTTAGCT TCATTTGCTG    12060

TTCAGACTAA ACTTGGAGAC TACAGTCAGT CAGAGAACTT GCTAGGCCAC CTCTCAGGTT    12120

ATTCTTTCAT TCCTGATCAT CCTCAAAATT TTGAAAAGA AATTGTAAAA ATTACATCAG     12180

CAACATATAG GCTTATGTCC TTGAGAAGCA GCAGTTAATT ACCTAAACAC AGCAAGTACC    12240

TTAGAACTCT GTGGAGTTGA ATTGCACTAT GCAAGGGATC AAGTAACAAT AAAATTATGA    12300

TTGGAATGAT GTCAAGAGGA ATTCTGATTT ATAACAGGCT ATGAATGAGT ACCTTTCCAT    12360

GGTCGAAGAT TGTAAAAATT TGTTTTAAGT GCAAACAGTT TTTTATTCAG CTTTGAAAAT    12420

GACTTGCATA AATCTGGAGA AAGATTATCA GGATTTAATA TGGTGAATTA TATGGCATGT    12480

AAACATTTGT GGAAAGCAAG TTTAGAACAT CACATATTCT TCTGTTTGGA CAGACCACTT    12540

CCAACTAGAA AGAATTTTTT TGCACATTAT TTTACATTAG GTTCAAAATT CCTAATGCAT    12600

GGTGGGAGAA CTGAAGTTCA GTTAGTTCAG TATGGCAAAG AAAAGGCAAA TAAAGACAGA    12660

CTACTTGCAG GATCCTCAAG TAAGCCATTG ACGTGGAAAT TAATAGTTTG GAAGTAGTA     12720

GGCAGGAATT CAATATCTGA TGAAAAGATT AGAAACATAA AGCCTTCCAT CACAATTCCC    12780

ACCCGGAACA GGAATTCCTA CTCATCAAAA TTCTGCATTC ATACAAGAGG GAACCTGATT    12840

ATGACCATCT TCTGTTGGTC ATTTGGTAGA TTATGTGGTT CACACTTCTT CCAAATATTT    12900

GCAAATCAGA CATCACCATT ATCAGCACAA GCTAATAGCA TCATTCTGGA ATCATCACTA    12960

TTACAGGACA CCCCTGGAGA TGGGTAGCCT CCAGCTTTAC CACCCAAACA AGCTAAGAAA    13020

AACTGTTGGA ACCAAATTCA TTATTTACAT TTTCAACAAG ATCTGGAAGA TCATATTAAT    13080

GAAACGTTGA TGTTCTATCT TCTCTTAAAA AATCTGCTCC TAATGGTGGT ATTCTACATG    13140

ATAATCGTGT TCTAATCCGA GTGAACCTGA CGAAAATGAG AGGTTTGGAG TCAATGCAAA    13200

GGGGGATATG ATCAGAAGAT GTCTGTGATC GTGTCCTGAG AAGCACCAGG AACACCTTTG    13260

ACCTCAGTGA CTCTCGATTG AAGAGAAGAC CAAGTTGTAT TGATCAGTGG TTGGGACTTT    13320

ACAGAACACA CCCATGATTG GGTTGTCCTG CTTTTTAAAG CCAACTGTGA GAGACATTCT    13380

GGGGAACTCA TGCTTCTAGT TCTACCTATG CTGCATATGA TGTAGTGGAA GAAGTGCTAG    13440

AAAATGAGAC AGACTTCCAG TACATTCTGG AGAAAGCCCC ACTAGATAGT GTCCACCAGG    13500

ATGACCATGT GCTGTGGGAG TCAGTGATCC AGCTAACCGA GGGCTTATCG CTGGAACATT    13560

CTGGACACAA TTTGATCAAC TTATCAAAAA AAAACTTGGA ATGACAATTT CTGGTGCCAG    13620

ATTACCTTAG AACCTTTGCA AAAATAGATA GAGATAGTTT TCCTTATGAT GTTACATGGC    13680

TTATTTTTAA AGGTAATGAA AACTACATCA GTGTAATTCC AGCATCATAA GTCAGAACAG    13740

TGCTTGTCAA GGGGCGTTAC CACACACTTG AACAGATTTT TGGCAGATGA CTTGGGAACA    13800

AGGCTCCTCC ATGTTTGTAA TGTTGACCAC ACAAGTTGAA TGTGGCAGAG TTAAATGACC    13860

CCAATATTGG CCAGAACCCA CAGGAAGTTC ATCCTATGGA TGCTACCAAG CCTTCTGCCA    13920

CTGAGAAGAA GGAAGCACTG TCTTTATCTT CAGGAAGATC ACACTGCTGT TAACCAAGA    13980

GAAAAATTAG AGAGTCATCA ATCACGCAGA TCCAGTACAG AGGGTGGCCT GACCATGGAG    14040

ACCCTGATGA TTCAGTGACT TTCTGGATTT TGTTTTTCAT ATGCAAAATA AGAGGGCTAG    14100

CAAGGAAAAA CCCCTTGTTG TTTCTTGCAG TGCTGGAGTT GGAAGAACCA GCGTTCTTAA    14160
```

```
TACTATGGAA ACAGCCATGT GTCTCATTGA TCTCATTGAA TGCAGTCAGC CAGTTTATTC   14220

ACTAGACATG GTAAGAACAA TGAGAGAGCA GTGAGCCGTG ATGGTCCAAA CACCTAGTCA   14280

TTACAGTTTT GCGTGTGAAG TACTATTTTG AAAGCTTATG AAGAAGGCTT TGCTGAAGAA   14340

AGCAAAAGGA AAAAAGAAC TTTGTCATCT GTTAGGTTCC ATTTATTGCA TGATAATTGT   14400

GTTTGTATTG ATTATTGGGC AAGTAGCTGT TTGCTATTTT GATCTTATTT CAGAAGGGCA   14460

TAATAATTTT ACTATTCAAT GAAACGTTTT AAACGGGGTA GAAAAAGACT AGTTTTTGTA   14520

TGCTTTACAG CAGAAATCTT ATAATGATTA ACTGGTAATA TATTTCGTTG GCATAAAAAT   14580

ACATTTAAAA GTTCAAGTAA TTATAAACAT TGTAAATTGT ATATGTAATC ATATTGAAAT   14640

TGAAATTCTT TATAGCTGTA CTTCTGTGTA ATCAAAGACT GGGGAGAGAT AGACTAGCTA   14700

GCTCTTTCTC TTATCCATTA ATCACTTAAC AGAGTTTTGA ATAAAAAGTT CCATTTCATG   14760

GGATAAGAAT AATGACAGGT TAACCTATTT TAGTTGGTTA CTATGTTCTA GGTGTTGTAT   14820

GAAGTAGTTT ACATAGTTTC ACTGATTTCA CTACAATCCC AGGAGGAGTA GTTACTATTA   14880

TTACACTCAT TTTACAGGCA AAGAAATAGG TTTGGAGGGG TTGGGTGTTT TGCCCAAGTT   14940

CTCATCGTAA AATGACAGAT GAGGATTCAA ATTCAAGTCT TAATTGAAGT CCATTACTTT   15000

AGAACCTACC TCTTAGTGGC TCTTATGTTA CAGTATAAGG GAGAGCAGAC TGTTCCTTTA   15060

CCCTTGTAGG GTAGCTAGGG CTTGTGAATT AAGAGACTGA TTAACAGGAG AAGAGGCATA   15120

CACATTTTAT TGACGTTAGT ATTTTTACAT GCACAGGGAA GGAGGGTTTT ATTTTTATTT   15180

TTATTTTTAT CTTTATTTTA AAGAGACAGG GGTCTTGCTG TGTTGCCAGG GCTGGACTCA   15240

AACTCCTGAA GCCAAGCGAT TCTTCTGCTT GAGATTCCTG AGTAGCAGGG ACTATAGGTG   15300

TGCTCCTCTG TGCTTGGCTA AAGAAGGGGT TTGTATGTGA TTTTTAACAA AGGCTGATAA   15360

ATTGTGAAGA AGTGACTAGT CAAAGGAGAA GAGGATTTCA GCTCCCAGGG GTGGTAAATT   15420

GTGGGAAGAT GACTAGGAAA TGTATAGTAA TAAGGTTTGC TATGCAGGTT TATTTTGCCA   15480

GTTTCTGGTC TCCTAATAAG GGACAGGGAA ACACCTTTAC AGATGGAAAT TCATATCACC   15540

TTTCCACAGG GAAATTTATG TCCTGCCTTA GGCAGTTAGG GGAAGGGCAG AGAATTCTTC   15600

CTGTATCTGC TGTGTCTCAG GTGCCTTCAG CTCAAAATAA TCCTTATGCC AAAGTAGCAT   15660

ATTTGGGTGT GGCATATTCT CTGATCTCTT TCAACAGCAT CATCTATACT TAACAACAGC   15720

AAAAGTTTTT TTTAAAAAAT CATGTTTCAA GATTTGCATG TGGAAGACAA ATGGACATGA   15780

TTGAGATAAA TGAAGAATAT ATATTTTTA ACAAAGAATG CTGTATATTT ATGTCTCTGT   15840

GACATTGTGT TATGGAGGCT AAGGTGTTAA GCATGTGATT ACTTTAGATG CCGTATGACT   15900

ACCTGTTTTT AAGATTAAAA AAGAATCAAT AGGCAGTTTA TATGCATGGG AGCAAGTTAA   15960

AAACAACACA GATGTGATGA AGGCGAGGTG AAACTGGTCC GCATCTAATT CAGGCCTTCT   16020

CCTGAAAGCC AGTGTGTGCA AGATAAATAA GTTTGTTTGA CGAAAGCAGA ATAACTAGTT   16080

TGTCCTTTGT GATGAAGATA GTTATTCAGA AATCATTTTT ATTGGCTACC TCTGAATTAA   16140

TAAATGAAAA GAGAAATTTT TTTTTCTGTA GGGGATGTCT GATGAGTTCT TAAAAAGTGG   16200

ATGAACCTGA AATTATCATG AACAAGCAAT TATAATGAAC TTAAAATTAC TTAAAGAGTT   16260

ATGAAAAACA AAAAGAAAAG CCGTATGTTT TCTTGTGCCT TATTTTGAAG TGACAAATTA   16320

TTTGCAGGGT ACATTTGTAG ACGGAACTAA TGTGATTTAA AAAATGAGTA CTAGATTTAC   16380

AGAATGATGC CTTTAAAAAG TCACTGGTGC ACTTTAATTA TTTTATTTAT GTTTATTCTG   16440

AAACTACCTT TATTTTGAAA ATGAGGTATA GCTTTGCCTA CTGGTGACAA AAGTGTAAAT   16500

AATTCAGTAA ACATCTGTTA AAAACCAGCT TGGTGCTAGG CTCTTGGGGT AGAAAACTGA   16560
```

```
TCAGGCCATT GAGGAGCTCA TAGTCCCTAA GGGGCTGGGG ACTTGTCATT AGGTGTGCAG    16620

TGTGTTCTGG ATGCTCCTGA AGGAGTGTGG GCAGGTGCGC ACCACCATGC CTGGCTAATC    16680

TTTTTATAAT TATGTAGAGA CAGGGTCTGG CTGTGCTGCC CATGCTGGGT TTGAACTTCT    16740

GGGCTTAAGA GATCTTCCCT CCCTGCCCCT ACCGACCCCG CCCGCCCACT CCACCTCAGC    16800

CTCCCCAAAG CACTGGGATT GCAGGCATGG GCCACTATGC CTGGGCTGTG CAAAACTTTT    16860

AAATCAGTGC ATACTCAATG GTCTTGATGC AATTCTGGCT TGTTGGTAAG AGAATGGGGA    16920

TTTACTCACA AGCCACGATG TCACTTTTAA CTCTGAACAG ATCAAGCTAT GGTATTACT     16980

CATTTATGTC ATCGATAAAC TTTATGAATA AAAACTCATT GTGCAAATAT TTAAACATAC    17040

TACATACATA GCACTGTGCA GTTTCTAAGG AAAGTAATGG AAACCTTTGT CACATCCCTG    17100

GCTTCCAGAA CTTTATGTTA TCTAAGTGCA TTTGTCTGCA AAGTTGTTGG GTTAATTGCC    17160

CCTTTCTTTC TTCTCTTTTT AAGATATTAA TAAATAGTGT CATGACCAAA AGATAATCCT    17220

TATGGACAAG ATAGATCTAA AAAGCCTTAG CTAATTTATA ATCTTGCATA ATCCATGATG    17280

ACAAGATGCA GAAACAAAAA TGCCCAGAAT AAAAACTTAG CACCATTAGC AGCCATTTCC    17340

TTTTAAGTCT TTACAAGTAT ACTCCCAGTT TCTTGAAAAA TTTATTCTAA AATATGTAAG    17400

ACACACAAAA CAGCAGAAGG ACTAATACAG GTACATCGAA CACCTGTGTG CCTACCGCCC    17460

AGTTTAAAAA TAAACTGGAA TGATGTTTCT CTCATACTTA CAGAATAAAG TTTTAATCTT    17520

TAGCATGGAA TTCAAAAGAC TTCTGCCATT CCAGTTCAGA GCCACCCTTC TGGTCTCCTT    17580

GCTCCTCAGC CGCGACACTG CCCATGTACC CAACAGGCCT CCAGGGTTAC TGCTTCCATT    17640

CGTTCTTATT CTCATGAACA TTTTCCTTCA TCTCATCTGC CAGAATCCTA CCTAATAATA    17700

CTCCTGCTCT GCAGTTTACA GTTCTTTAAA ATTAAAAAAG GTTGTGTACC CTTTAGTGTC    17760

CTGAAAAAAG AAAAAACAAA TTTAAAACCT TAAAAAGGTA CCATATTTTC ATAGTATTTG    17820

CGTTATGTCT CATTACAGTT CCTGTGGACA TGTCTGTCTC TTTTACTAGA TTGATTGTGG    17880

GCTCTTTGAA GGAAGATATA TCTTATGAAC AGTGTTTAT ATATTGTTAG CAATCAATGA     17940

ATGCTTGCTA TATTTTTCTC ATGAGGATAT TGATTATTCT ATTTTAATTT ATTACCNNNN    18000

NNNTGTACTA TACATAACTG CTTTCTGTAC CTGAGCTATT TATGATCTCT GAGGCTCCTG    18060

TGAGAAATCT AATTTTTGTT AATCATGGAT GGAAATATTC ACAACATCAT TCGTCAGTTT    18120

CTTCACATTG TCTTCCTTTG TATATTACAG ATGTTTTAAA ATATCAAAGT AATGTTTTTT    18180

TGTTTTATCT TTTAGATATT GCTATATGGA GATTTGCCAA AAAATAAAGA AAATATAATA    18240

TATTTAGCAA ATCATCAAAG CACAGGTTTG TATTTCATTT GCATGAAACC TAGGTTTTTC    18300

TACAGATGGC ACATGGGCAT TCAAAATACC GTTCTTATAT TTAAATGAAG TGGGTTTTTT    18360

AAAACAGCAA TTTTCTGTGC AGATATTACA CCTGTTCTTG TATTTTGTG ATTTTACTTT     18420

TTGGAAAGTC AGAAACTTGA AAGCTATGAA TTTTCCTAAA CTTACCTTCT CCCTCTGTTG    18480

GATGTAAGTA AGCTATCTTC TTACTTGCTT GCTTTGTTTT TCCTTTGTGT AGCTCTTTAA    18540

AGAGTGTATT CATTCTTTTT GTAAGTGATG TTTCTAGAAG TAGCATTGGT GGGTCGAAGT    18600

GTGTATACAT TTTACATTTT TGATTGCTAA GCTGCAGAAA AGCTGTATTG GTATGTAAGT    18660

ACTCGTTTCC TTACTATGCT CGTCATTTCT AGTGTCTGCT CTTCCTTTCC TTCTTCAAAT    18720

GGGTTTGGTT TAATTCTAGT TGCTACTGTT CCATCAGAGG AATTGCAGAG AACTGGTCTT    18780

CAAAACAGTG CAGTATATAC TTTAGGTGAA GATACTTCTA AAAACCTTTG TATTTTGAGG    18840

TAATTCTAGA GTCCCAAGAA TTTGCAAAAA GAGTACATTG TCAGCAATAT TTTTCCCAAT    18900

GGTGACATCT TAATATAACT GTAGCACAGT AGCAGAATCA GGAAATTGTC ATTGGGTAAG    18960
```

```
GTACTTTTTA ATTCTCCAAA TAATTCAGCC CTCCAAAAAA ATCCCACTTC TTATGTTTTC      19020

AAACCTGTAG CTACTTTTGA TGCGTACTTC CTAAATTGCA TTTTTATTAC TTTAAAAAAT      19080

ATAATACCTA GAAGCTCAAA GCTGGAAACA GCCTGATCAA TATAGTACTC TTAAGCTAAA      19140

AACAACCTGA TCAATATAGT ACTCTTAGGG AAATCACTTA TGCCTGTGGC TTTTTTTAAA      19200

TTTTCTTCCT GTCAGCTGTC TCTTCATGAT TTTGTGGTTT TTATTACTGC TTATACCATA      19260

GATGAGGTAT AGAAAGTAAA AGAAGTTAAA ATGCATTTTT CTCAATTTAG TGAATTAATG      19320

ATTACATTCA GATTTATAGG ACAAGGGTTG AAGCTANCAA GGGGTTGATA GGAATCTTGA      19380

TGTATCTGAG TATTTTCCCC AACTTTATTA CATGACTGGT TCAGACTATT TTATCTAATT      19440

ACATTTCACT CTTGGCAGAA ATAGCAAAAC AGTCAACCAA TGGTCAATGC TGCTGAGAAC      19500

TCTGGCCTGT GCAGACATAT TGGCTGTTTT ACTTCTAATA CCATTCTGCT TTTCCTGTCC      19560

TGCTGCTGAT GGATGTTTCT TCCAGGTTTT AAATATCAAA CAAAAGGGAT CTGTGGGCCC      19620

AGTACAGGGA ATGGCTCTTG ATAGATTTGA TTTTCCTGCA TTTCCTTTAT TTTGATCCAG      19680

TGTTAATTTC ATGTAGAGTT GTCTGTTTAA CAGGATTCTC TTAAAATTCC TTCTTCAGTT      19740

TACCTGCCAG CTTTTCTTTG TCCAGGTTTC AGTATGAACT CCACTCGATT AATAGAGCTC      19800

TCTAGTAGTG ACTTGTGGAG TGGGTTCTCT GAACATTTCT GGAAGTGTTG CTGATAGTGA      19860

TAATATTGAT CACTAGTACT GTTAATTTGT GTGCTTACTA CATGTTGGCT TTTATATGTA      19920

TTCCTTCAGA TTAAGGACTT CTAGAAAACA TCCATGAAAA AACAGATTAA AAAAAACAAT      19980

TCTGCATGTA TTTGGGACTA GAAGGTACTA TGGGAAGGAT AATCTTCATA CTCAGACCAT      20040

ACTGACCTGA ATTTCATTTA TCAGTTTAGA GAACCACTTC CCCTTCCCTT CACCCTACCT      20100

CCGAGTGCCT GTGACTTTGT ATCACCGCTC TGGCACCACA TCCTCATCCC AGCAGGATTT      20160

GGGAAGGCTG CTTTTTGAAA GCCTTTTAAA ATTCTGTAAG TTGAGAAAAT ACTAGGGGAA      20220

TGATTTAAA TTTCTTTAGA ATTACAGGCT TTAGTCAGTA TATGACAGAG CCTTTTCCTA       20280

GAAAAATGTG CATATAAAAA TTTGCATGTA GTTTTAGGGT TTCAGAGACC CCTAAAGCCT     20340

ATCCATAGAC GTGGTTCATT GTCTGATTGT GTTTAGGTAC CCTTCTAAAA CCCTTTTGAG     20400

ATGTTAGGAA TCACAACAGA GTATCTCTGA AAATGTAATT AGCGGAAAGA ACATTTCAAA     20460

GACTGTTGTT CTGCTTAGAC TTTCTAGTTT GTCTTCTGCC AGGCTTGCCG GAATAAATGA     20520

GTTTCCTGGC CTGATACTCA AAAGAATTGA CATTTAAATT AGTCTCTCTC TTCCCTTGTT     20580

TTCGCTTGAC ACATCCTTGT CTCTACATTC TGTCTCTGTC TCTGTTAGCT TATTTCTCTC     20640

TCGAGTCAGC AGGATATAGT GGCTGTTATT TCTTCCCCTT ATCCTTCAAC GATCTACTTT     20700

TGACAACACT TTGCCTTTTT TTTTTTGAGA TGGAGTTTCA CTCTTGTTGC CCAGGCTGGG     20760

TGTAATGGTG CAATCTCAGC TCACTGCAAC CTTTGCCTCC CGGGTTCAAG CCATTTTCCT     20820

GCCTCAGCCT CCCGAGTAGC TGGGATTACA GACATGCACC ACCACGCCTG GCTAATTTTG     20880

TATTTTCAGT AGAGATGGGG TTTCACCATG TTGGTCAGGC TGGTCTTGAA CTCCTGACCT     20940

CAGGTGATCT GCCTGCCTCG GCCTCCCAAA GTGCAGGGAT TACAGGCGTG AGCCACTGTG     21000

CCCTGCCTGC TATTTGCCTT TTTAATCTCA TGAAATGTTC TCTTTTCTTG GCTGAAGTGT     21060

CACTTTTCTT GTTGAACAGC ATGCGTGGTG AGTAGAATGT TATAAAAAGG GATGGACTTT     21120

GGAGTTAGAG AGACCCAGGT TCCTGTTCGG CATTGCAGAA ATGCTGTTCT GCAATAGGCT     21180

GTGTGTCAGT GGGCAAATTA CTTATCTCTC AGAGCCTTAT TGGTAAGGTG TGAGTGATAG     21240

CTCCTTTCAG GCACCTTACA GAGGCTGTCT CCTAATCCTG GTAGCGTACC TGGCTCATAG     21300

ATGGCATTTA AAAGTGGTTG TGATGACAGT CATAGCTCAC CATTAGCATA GCGCTGGATC     21360
```

```
CATGGCAGGG AAGCGCTGCA CATGCAGTAT CTCTTGGACT ACACAGGGCC CTCATGAATT    21420

AGGAACTGCT GTTTCATGAG GATAGGGATG AGGAAATTAG ACTTGCTGCC CCTCACTGCC    21480

TTCCACTCCT CTCCTCCAAG TTAATGGGAA CTATGACTCT GCTTTGGCTT GATTGCCATG    21540

GAAGATTCTC ACACAGCCAA ATTTATTGCT ATCTTAGTTA AATTATGCCA GAACACAAAA    21600

TATGAAGTTA TTGTCAAAGT AATATAATCT CAGCTGTAAC TGAGATAGTC AGAAACTGTC    21660

TGTAATCTGA TGTCCTATCT GAAAGGTAGC TGAGAATAAA CAAGAAATAA AGAGAATTCA    21720

GTAGCAAATA TTGGTGACAC AAAGCTTTTA TATTTTGACT AGTTAAGCTA GTTCTTAAAT    21780

GTTTCCACTA AAATATTCAA GTTAAGGGC ATAGCCCAGG GCAGCTTATT ATGAACATGA    21840

TGTATTTTGG AAATCTTACA CTTTCTCTTA AAAGTTCTTG GGAGGGGCAT GTGAGGCCAT    21900

AATATAACCA TAAAACCATT TGTTTTAAAA TAAAACCCAT TTTTAAAATT CTTCCAAATA    21960

AAAAAATTAT TGCAGGAAAA AATGCTAAAC CTGGTTTTTA ACTTTGTACG CCAACTATAT    22020

TTCCAAGATG TGCTGTAGCC TGGTAACCAT ACAGAACCAT ACAGAATTAG TTCTCAGAAT    22080

TTATTGTCTG CTTACTTTTG CATTTGGTAC AGGTATAACA GGGTCGATTA TATGGTTTCT    22140

AAGACATGAC TAGAAAGAAA TATGTTTATC AGTTATTATT TCTTCCATCT AAATTAGAAG    22200

GGGCTAGGGA GAGGGCTTCA ACAGGAATTT ATATACTTTA GAGAAAAGTG ATCATTGATA    22260

GCCCAATAGT ATAGATATCT CAACCCAATA ACACAGGTTG TGTCTGTCTC TGGGATCATA    22320

CACTGTAGGG GAGAATCTTT GCAAGCAACA TTCTACTTAT AGGGAGCCAT AACAAAAGTT    22380

TCATATGTAT AATAATTATA AGTCTTAAGT CATCAAGAAA AAGTTAACTT GTGAATGATA    22440

ATCCCTGATT AAAAAGAGAG ATGTATAATA ATGGATAAGA GATTTTTCTT GGTTAATTTT    22500

TAGTATTAAA ATGGCTAAAT CTTCTTTGGG ATATTCTGAC TAGTATGGTG CATTGTCTAA    22560

TAGATTTCCC ATAGCTGAGA GCTAATCATC TTGTAATCTG TGGAAAACTG TCCTCTTTGG    22620

CTAAAACTTT ATTGTAATTC CTCTAAATCC TCAGCTTTTA TTTTCTACAG ACTTTTTTTT    22680

TTTTTTAACA TTTCCTTCCT CTGACTCACT CCTTTTGTTC TCATTTTCAT GGCCTGAGAA    22740

CATGGGTGAT GATAGAATTA TTCTTTTCAC AGATTAACAG TTTTCTTTTC GAGTATCGTT    22800

GAGCTCATGT GTGTATTAAC TAGAGAAGTC TCCCTTACAT TTCATTTTTA TGTTTTCTTT    22860

CTCATCAGGA GATAGTTTGT AGCCATTTAC TTTCAAATCC AAGTTCTGC GGTTCTTAAG    22920

ACCTGTATCA TTTGTCTCCT GAATTTCACT TCATTTCCTC TTTAAACCAT GTCCTCTGTT    22980

TCCCATCTTC TGCACCCACT TTGCCACTTC CTGTTTGTTT AATTGGCAAG GCCACTCTC    23040

TGTGTTGGAA ATTTTTTCTT TTTGAAAGCT CAACTAACAA CTTCTAGGAA GTTTTTTATT    23100

GCTACTGTTA TCAATTCATA CCATCTTACC CTTGTTTTTG CAACCCTTTG TTAATAACAT    23160

ATTTATTTAA CTATAGTTAT TAGCAGTCTG AGATCATTTT ACTTGGTTAC ATAAGGAGCA    23220

CATATATCTA CCCAGCATCA TTGTAAGGCA TGTGAGACCT TTGTTTGATT GCTGTCCTAA    23280

CCTAGTACCG AGTCCTAAAA ACTCATTAGT AGAAGATGAA GTGTCCTTGC CTTTTGCTGA    23340

ACATATATAT ACACACTGAA TATTTAGTGG CAATTCATAG TTGCATTTGG CCATTTTTTG    23400

TTTATAATTT CCCCTTTCTC ATTAAAAAAA CTTTGTTTTC TAGACTTTAG GATTTAGAGA    23460

AGCTCATTTT GTTCCATACA CATGCTGCTG TTGGATTATT TAGGTATTTT GTGACTGTAT    23520

TTTATCTTTG AAATAAAAAG CCTTTCAAGA AATGCAAAAA AAAAAGCTC AAAAAACAGA    23580

AAATGTATAT TTTTTAAATA TCTCAGATAG ATTTAAAGAA ATTTTAAACA TCCTAATCAT    23640

AGTACTTTTG AAGCCCATTC ATAGTACAAC CTGTGAAGAG CCTCATGTAC GCGCTAACTG    23700

GGTCCTGTCT CTGCAGTTGA CTGGATTGTT GCTGACATCT TGGCCATCAG GCAGAATGCG    23760
```

```
CTAGGACATG TGCGCTACGT GCTGAAAGAA GGGTTAAAAT GGCTGCCATT GTATGGGTGT    23820
TACTTTGCTC AGGTAACTTG TTTCCATGCT TTTCTCTCTA TATATGTAGT TTATAAATTT    23880
TTTTTTTTTT TTTTGGAGAC AGTCTCACTT TATTGCTCAG GCTGAGTGCA GTGGTGTGAA    23940
CACAGCTCAC TGCAGCCTTG ACCTCTGGGG CTCAAGTGAA CCTCCTGCCT CTGCCTCCCA    24000
AGTAGTTGGG ACCGTAGTGC CCACCATCAT GCCCGGCTAA ATTTTCTATT TTTTGTAGAG    24060
ATGGGGGTCT CGCTGTGTTG CCCAGGCTGG TCTTGGACTC AAGCAATCTG CCTGTCTCAG    24120
CCTACCAAAA TGCTGGATTA TAGGTGTGAA CTGCCATACC CAACCCTATA AAATGTTAT     24180
ATTTTAAAAT TTAACAATAT ACTTCATGTG AATGTATGGT TTTAAAATG GGTTTAATAG     24240
TTTATTCTCA GTTGAAGTAA TTTTGTTTGG CATTTTTAGT GGTGTGTATT TATATACGTC    24300
TGATTATCCA TATGCGGTTT TCCTTCAGCA TCTGTGGGGA TTGGTTTTAG AACCACCACA    24360
GATACCAAAA TCTAAGGTGT TCAAGACCCT CATATAGAAT GGGATAGTAT TTGCATATAA    24420
CCTGTGCACT ACTTTAAATC ATCTCTAGAT TACTTATAAT ATCTAATACA TTATAAATGC    24480
CATGTAAATG GTTGTTATAC TTTATTTTTT ATTTGTATTA TTTTAATTGT TATATTATTT    24540
TTAATTTTTA TTTGTTCACA TATTTTTGAT CTGTGATTTG TTGAATCTGC AGATGTGGAA    24600
CTCATGGATG TGAAGGGCCA GCTGCAGTAA AATGAAAGAG CAAAAATGCA AATGTACAAA    24660
GTTCAAACAA ATAGGAAATT TAAAGGCATA GAATTTGATA GGCAATTACA TTAAACTGTT    24720
GATAACAGTA ATTAGTGATC TGTATGATAT TAAAAAAAAA AAGCAAACTG TATATATAAA    24780
ACTTACTTTC TCCAGTTCTG GAGGCTAGAC ATCCAAGATC AAGGTGTTGA CAGGGTTAGT    24840
TTCTCCCAAG GCCTCTCTCC CAGGCTTGCA GACAGCATCC TTCTTCCTGT GTCCTCAGGT    24900
GGTTTTTTTC CCTGTGCCCA AGCACCCCTG GCACTGCTTC CTCTTCTTAG AAGGACTAGT    24960
TACACTGGAT GACTAATCCT TCTACAGAGA CTGCTAAGGT CCCACTCTGA GGCCCTTTTT    25020
TAACCTTAAT TACCACCTCT AAGTCCCTCT CTCTGAATAC AGTCACAGTG GAACTATTA     25080
GGGCTTTAGT AGACTGATTT GGGGGAACAC ACTTCTGTCC GTAACAGTGC CACATAAATA    25140
TCTTTAGCAG GATTGATTTT TTAAAATCCC TAAAGATCGT GAGTATTGAC ATGTTAAGGA    25200
CGCTTTTTAG TGACTCTGTA ATAAGTGGGT GGAAGAATTG GGAGTTAAAT CCATCTGATG    25260
GATCAGGTTT TTTATTTTTA AAAATGTGTA TTTAAGAAAG AAAGCATTTT CATTTTAACT    25320
GCCAACAAAA CTAAACTTCA TGTGTTTTCC AATACAGTGT CACATGCAGT TTTTTTGAAT    25380
TATGTTGAGA CAAGGCAATT TTCAGCTAAA TGTTCTTTAG AAGCTAATGT TTGAAGATAT    25440
TAAATATAGA TTAAATTCTG AAATGTAGTT TTCATTCTGT ACTTTTTGCA AGAGAAGTTG    25500
CCTTTTTGAT GACTCTGGCC AATTGTTATT TTAAAAGTAA ATGCTCTTTC TCCCGATTTG    25560
ATTGTGGCAG CATGGAGGAA TCTATGTAAA GCGCAGTGCC AAATTTAACG AGAAAGAGAT    25620
GCGAAACAAG TTGCAGAGCT ACGTGGACGC AGGAACTCCA GTAAGAGCCT ACCCGTTTTT    25680
ATTTTTCTTA CCAGCTCTCA GTTTCTAAAT TTAAGAATTA AATTAAAATC TAAGAATTGT    25740
TTTGACAATG TATTTTCCCA TGTGTAATTA CTAATTCAGG GTTATGCTGA GGTAACAGAA    25800
ACCCTCTATG TACAGGTAGG CAGGTTTTTC AGCCATCAGA AAGATTGCTG TAAACAACTA    25860
GGTCCTTTGC TGGTCAGTGG ACCTTAAAGA GGAATAAAAA GAGCATTTGG TGTCGTTCAG    25920
AGTCTATAAA TAGAACTAAC TGCATTTTAA CCTGACATTT AAGCTAGTTT ACAAGCTCAT    25980
CTTACTTCTT GTCTTCTTTA GTATCAGATT TGGTTTTAGA AGCAGCAACT GTTTTCTGTT    26040
AGTGCAAATT TTGAATGTCT TACATGTACA GAAAAACCAA AAAAGGATGA ATCTCTACAA    26100
ATGTTAAATC ATTCAGTGTA AATAATATTT TATAAAACTT TATTCCACAA AAGTGGGGAG    26160
```

```
AGTTCAATCT GCTTTGTATA GAATGCTGAT TGCTGCCAAA GGCTTTTCCC CTGGTTCCCT    26220

CCGGAGACAA AGCACCATGA TCACCGGGGC GACTTGGGCT TTCTCTTTCA GTACATGACA    26280

TGTGCTCAGA AGCTTAGCTC GTGTGCACAG GCTTTCCCTT TCCTTTCTGG CTCCCTCCCT    26340

CTGTCTTCCC TCCTCTCCTC TTGCCCTCCC CTCACCAGGG GTCCTGGGCA GCAGCTGGAG    26400

CTCATGGTGA AGGAAGAATT CTTCATGGTC AGCTGGCGAA GTGCCTGGTG TGAGCATTGT    26460

TTATTCACAT GCCTCTTCTA GGTGTTTTTA CATTAGAACA TTGCATCTGT TTTGGGCATG    26520

TGTTGGGTGA CAGAAGCAGA ATGGAATGAG ATGAACAGTG ACCCTTTATC CTGTTATAGC    26580

TAACCCTTGA GAACCAAGCT TGGTGTCTTC AAAGGGTCTG TTTAGTCTGA AACAGTGTGG    26640

TGAATTTGGG CAGAATTGTG GTCATTGCAT GTAGGTCTCC AAAAGACAGA ATAAGTTGGT    26700

AATATGGTTT ATCGACTTTT TACAAAAAAA ATTTAAAAAT CATGAATTTA TACCTTAAAA    26760

TGTCCATCCC ACTTCTCTCC CAGCTGTCCA GTCACCCCAG CAATGGATGA CTGCTGTGGA    26820

GTTCCTTCTG TGTCCTGCTG TGGGCATTGT ATATATGAAG CAAATGAAGA TAGCTGCCTT    26880

TTGGGTGATG TTGGCATCCT ATGCACAGTG GTCCCTTGCT TTTTTGCCCC CATGAATATA    26940

GCTGCCAGTG GCGCTAGGGC TGAAAAAATC AGCTCTTTAC ACTTGTCATG TGTCTTGTTT    27000

ATGTGGCTGC CTTCGTGAGT TTCTTCTTGT TTTTGGTTTG CAGCAGTTTA AGTATCATAT    27060

ATCTGAGTGT CATTTAAAAA TTTTTACCTG GATTGGTCCT CTGAGCTTGG ATCTATGATT    27120

TGGTGTCTGT TATTAATTTT GGAAATTTCT TTGCTCTTAT TTCCTTAAAT ATTATTCCTA    27180

CCCCAGTCTT TCTTCTCCAG TTATGTTTGT GTTGGTTCAT TTCTCGCTGT TCTTTAGTTC    27240

TTAGATGCAT TATTCGTTTT TTGTTGGTTT TTTTTTAAAT TTTTTTTTTT ACGCCCCCTC    27300

CCTTTTTTCT TTTTGTGTTA CATTTTGGAT AATTTCTGTT GACCCACCTT TGAGTTCATG    27360

GATTCTTCCT TTGGCTGTGT TGAGTCTACT GGTGAGCCAG TTTAAGGCAC TCTTCATCTC    27420

TGCTACTGCG TGTTTCATTC CTCACATTTC CCTTTGACCC TGTTTCATAG TTTCCATCTC    27480

TGTGCTAGTG TATCTATCTG ATCATAAAGC TTAGTCACGT TTTCCAGTTG AACCTTTATC    27540

ATTTTATTAT ACTTGCAGTT CTCTTAAATT CCCTGCTTGA TAATTCCAAC ATCTGGGCCA    27600

TATCTGAGTC TGCAAATTTT GATTACTTTA TCTCTTCAGA TTGTGCTTTA TCTTGCCTTT    27660

GTCATACTTC CTAAGATTTT GCCTAACGCT GGGCCTTTTT TGTAAGACAG GAGAAATGGA    27720

GGCAAGTTGT CTTGATACCT GGAAATGGAT AGACTTGTCT TTCTGCTTGG CTTTTAGTGT    27780

TGAGGAGTGG AGTCAGTCCA CTGAGGAGGT GCACTGCATT TGGGTTTTGC TCATGTGCTT    27840

TTTCTCACAG CTTCAGGTTT CTGTAGAACT CATTACTTTG TTTGTAGGTT GGGGATGTCC    27900

TCCCGCTAGA GCTTTTCCTC AGTGTCTATT TCACACTCAG CGTTTTCACA TAGCACCTTG    27960

GAGTGGCTCT CTTCTTTATG CCTTTCCCCA CTATACTTCT TGGATACTTG TTACTGAACT    28020

CTCGCTAGTT TGGTGGTAGA AGGAGAGGGA AGGGAAGTGT CTTTTCATTC TTAGGGAGAA    28080

TCTCAGGGGT GGAGCCTTCT CTGATCCTGC CTTGCTTCTG GCTGTAAGTC TGTGCCCAGT    28140

ATGTATTCCT GCCTTTACTA AGAGTTTTTC CCTGTTCTCT TCACCCAGCC TCATCGAGTA    28200

TTCATCCGTG CCCCATGGGT AGCAGGGTTT TGTTGCCCCT GTTCATCAGT TTCAGGCTGC    28260

TGTTCCATAG GAAAGGTAGA AAGAAGGATG TGGGCTGGGC CCTGAGCCCT TCCCACAGGG    28320

CTGCTTTTCC CTCCCACAAG CCTACATCCA GTCTTCCCTG ACCGCAGTGT GTTTTCTTTT    28380

TTCTTTGTCT TGTGAGTACA CAGGAGGTCT GTGGGTCGAG CCTGTGAAAT GTGCTGCATT    28440

CTCCTTGTGT CTGTAGCCCA GGGGTTCGTC TGTTCCACTG GCTCATACTT GGCTTTCTGC    28500

AAAATTGATA AAATTTTTAG CTAAATTCTT TTTACTGGTA TCTGTTACAT TGGCCCCCAA    28560
```

```
CTAAACAACC ACTTGCATCT TGTTTCTCCT TTGAGTTTTC CATCTTTCCT TAGACTTTTG    28620

GGTTAGTTGG TTGCCTTGCA ACCTTGCAGC TCTCTGAAGG GTCTAAGAAA AGTCATGAAT    28680

CTACAGCTTG TCAGTGTTGT TGTTGTTGTA GGGTTGGCAG TAGTATTCCT TCAGCATTCT    28740

ACATACTTAA TGGAAGCCGC CTCCCATTTT TGGTTAATAA ATTTCAAAAC TTGGAACAAT    28800

GTTAGATTTA CAAAAACGTC AGAAAGAACA GAGTGTTCCT GTTATTCTT TATATAGCTT     28860

TTTTTTTTTT TTTTTTTTTT GAGTTGGAGT CTCGGTCTGT CACCCAGGCT GGAGTGCAGT    28920

GGCACGATCT TGGCTCACTG CAACCTCTGC CTCACGGGTT CAAGCAATCT CCTGCCTCAG    28980

CCTCCTGAGT AGCTGGGATT ACAGGCGTGC ACCGCCATGC CCGGCTAATT TTTGTATTTT    29040

TAGTAGAGAC AGGGTTTCAC CATGTTGGCC AGGCTGGTCT CGAACTCCTG ACCTCTTGAT    29100

CCGCCCGCCT CGGCCCCCCA CAGTGCTGGG ATTATAGGTG TGAGCCACCA CGCCCAGCCT    29160

TCTTCATCTA GCTTTAACAT CTAATGTTGA CATCTTACAT AACATGGTAT ATATTTGTCA    29220

AAACTAAGAA ATAAACATTG GTACCACACT ATTAATTGTA CTACAGATTT TTATTCAGAC    29280

TTTACCAGGT TTTCCACTAA TGTCCTTTTT CTGTTCTAAA ATACAATCCA GAATAGATAC    29340

AAATCCATTC AACTTCAGTG TTTTAAATTA TTGTTTTTCA TTATATGAAG TGCTGTGTGG    29400

TTTTTGTCAA ATCTGTTATT TTGGTTTTAA TCTTCAAGCT TGTCTTTGTT TCTTTAAGTG    29460

ATAAAGGCAT AATTTAAAAG GTGTGTTGGG TTATTTCAGT GCCTAAAGTC TTGTCTGAGT    29520

CACTTGTTTT CTGCTGTTCT TGCTTATGGT ACTTTCTTTC CTTGTTTGCT TTGTTATCTT    29580

CCTTTGCTGC TGGCTGTGTT TGGTTAAGTT ATTTGTGGAA ATCAGTTGAA GCCTCAGGTG    29640

GGAGTGTCTT TCTCCGGAGA ACATTTCTAC CTGTTTTAGC TGGGCCCCTT AAGGCTCCTC    29700

TAGCGTGGGC CCCACCCAAA CGAGATTCTG AGTTGAAGGT GAACTGAGCC ATTCAGGCAG    29760

TGCAGCCAGG GTTGCAGATG CACGTGAGAC CTGCTCACCT CTCATTTACT TTCACCCTGA    29820

GAGTAGAGCC TTTGGTGTTT CGTTCACTTG TCTGATTCTC TCTTCACAGT TCTATTAGAA    29880

GGTCCATGGG TTTTGGTTTC TGTGCCCTTC ATCTTATGAG TCTTGTAAAT CAAAGTTCTG    29940

TTTTATGCTT ACTTCTGCTT TACTGTGTTT GCTTAATTTC AGTCTAACA TCTTGCCAAC     30000

TCTTGGGTAC TTTTAAAATA ATGTTATATC CAGCTTTTA AGTTGTTTTC AGTAGGAAGG     30060

TTGATTCAAA TAACCTAGTC TGGTTATGGG CTACGAGAAT AGCCTCCCTG TTTTTTGTGG    30120

GCAAAATTCC AGCCTTTTAT GTTCCTAGCG CAGTGTGGAT AACAGACTGG CAGGTTCAAG    30180

AGGCCGTGCT GAGCAGCTTT CACTGTAAGG TCACTGTCCC AGGTCGGGTT TCTAAGAATC    30240

TGGATGGTTG TTTCATTTCT TAATATGTAC GCCCTGTGAG AGCGGATACA TCTTGCTCAG    30300

GTTCTTATGA TTCTTTTGTT TCTGAAGGTG AATTAAGTAA GTGACATGGT AGAATATGTT    30360

AAGTCAACTT TCGTGTGGCT TACTAGTTCT CATGAATCTA TTCCATGATT GTATCAGTTC    30420

TTATTCAGTA TTAGTATTTA AGAAATGCAG AATTTTGTTT CAAAAAATAT ATTTGTATTA    30480

TAAGTTGTGA AGAAATACAT CTCCATAATT ATTGCTGGGA CAATACAGTA TTTTCTTAAG    30540

GAACTTATTG GTTGTGGATG CAAATGAAGC ATATTTGTGA TAAAAATAAC TAATAGAAGT    30600

CATTTTGTTA GACTATGAGC TAGTAAAACT TATGGCACAA ACATGGAGAC TTAACACTTT    30660

TTCTTCCAGC TTTCACTTAA GTTCCTTTTC AGATAGGAGG CAGCCTGGTG GATAAGAGTA    30720

TTGGTTTTGA AATTAGATTC AGGTTAAAT CCCAGATCTT CTGTTTAATC TTTATTTTAT     30780

TTCAGGTAGA TTTTCTGGAT AACTTGCTAT AGCTTATACG TCAGTACTTG CCACTTCAAT    30840

TTTATGTTAT GGAGAGACGG CTTCTTTCCT TAAACCTCAC GAACCAACCT CTGCTAGCTT    30900

CTAAGTTTTT TCCTGCCACT TCTTTACCTC TCTCAGCCTT CAGAGAATTA AAGGGAGTTA    30960
```

-continued

```
GGGCCTTGCT CTGGATTAGG ATTTGCTTTA AGGGAGTGTT GTGGCTGGTT TGATGTTTTA    31020

TCTAGAGCAC TCAAACTTTC TCCATATCAG CAATAAGGCT GTTTTGCTTT CTAATCATTC    31080

ATGTGTTCAG TGAAGTAGCA CTTTTAATTC TCTTTAAGAA CTTTTCCTTT GCATCCGCAA    31140

CTTGGCTGTT TAGTGGAAAG GACCTAGCTT TTGACCTACC TTGGCTTTCA ACATACCTTC    31200

CTCACTAAGC CATTTCTAGC TATTGATGTA AAGTGAGAGA CATGCAACTC TTCCTTTCAC    31260

TGGAACGCTT AGCAGCCATT GTAGGGTTAT TAATTGGCCT AATTTCAATA TTGTTGTGTC    31320

TCAGGGAATA GGGAAACCCA AGGGGCGGTA GAGAGAAAGA GAGACAGGAG AACAGGCCAT    31380

CATTGGAGCA GTCAGAACAC ACACGACATT TATCAATTAA ATTTGTCATC TTATATGGGT    31440

GCAATTCATG GCACCCCCAA ACAATTACAA TAGTAACATC AGAGATCACA GATCACAATA    31500

ACAGATATAA TAATATGAAA TATTGTGAGA TTACCGAAAT ATGACACAGA GACGTGAGGT    31560

GAGCACATAC TGTTGGAAAA ATGGCACCAA TAGACTTGCT CGATGCAGGG TTGTCATAAA    31620

CCTTCAATGG GAAAAAAATG CAATTTCCGT GAAGCTCAGT AAAGCGAAGC ATGATAAAAT    31680

GAGATGAGCC TGTCACTCCT AAGAATGTTC CTGTACAAGT TTTTTGCATC TGTTACTTAC    31740

CTTTTCCTAT TTGTGAATAG TATCTTTTTT GAGTACGTGT GTTTTTTAT TTTTATACAT     31800

TTATATGTAT CTTTTGAAGA ACATACTTTT AAGCTTAATT TATTGATTTT TTTTCTCTCA    31860

TAATTTCCAC TTTTTGTATC CTATTTAAGA AGTCCTTGCC AAACTTAAGG TTGCTAAGAT    31920

TTTCTCCTTT GTTTTCTTCT GGAAATTTTA GAGTTTTGCT TTTACATTTA GTTCTAGGAT    31980

TTATTTATAA TTAATGTTTT CATATGGTGT AAGATCGAAG TTCATATTTT TTTAATATAG    32040

GTAACCATCA CTATAGAAAA GATTATTTCC CCCCAATGTT TGAAATAAGT AGACTGAATA    32100

TAGATGGGTC TGTTATCCCT AGATCAATGG AGCATTTGTT CTGTTATATT GATCTATATA    32160

TATATATCCT TATGCCAATA CCATACTGTC TTAATAATGC TTGCTTTGCA GTAAGTTTTT    32220

AAATAGTGTA GTTGTCTTCT AAATTTGTTC TTTCTTTTCA AAGTTGTTTT GGCTATTTTA    32280

GGTTTTTTGC ATTTCTGTGT GAATTATAGA ATTAGCTCGA CAATTTCTAC CCAAAGTTTG    32340

TGGGCTTTTC ATTTTGATTG TATTGAAGAT ATAGATGAAT TTGGGAAGAA TTGATATAAC    32400

AGGATTGAAT CTTTGGATTC ATGAACGTAG CCTGCATTTG TTTACTTAGG TCTTCTTTAT    32460

TTATCTCAGT GTGTTTTGTA GTTAATGTA CAGATTTGCA CATCTTTTGC CAGATATATC     32520

CCTAAGAATT TCAGTTTTTG ATACTATTGT AGATGACATT TAAAAAAATT TCAAGTTTTT    32580

GTTTGTTGAC CTAGGCATAT ATTTGACTTT TTAAATATACT AACCTTGCTA AACTTATTTA   32640

TCATCTAGTA ACTTACAAAA TATATTCCTT AGGATTTCCT ACATAAACAA TCATGTCATT    32700

GTTTTAGAAA TAACAGTTTT ACTTTGTCCT TTTTAATCTT GATGGCTTTT ATTTCTTTTT    32760

CTTGCTAAAT TTTCTGGCTA GACCTCCTAG TACAGCCTTG ACTAGAACTG GTGTGAGGGA    32820

AATCCTTTCC ATATTCCTCA TCTTTAGGGA AAAGCACTCA TTCTTTTATC CATTCTTTAG    32880

TTCCTAGCCC CATTGCCCTT CCTAAATTTT TTCTCATCAT TTTCCTTCAT CACACCTTGT    32940

TCTTTTTCTT TGCAATCATA TCATGATATG TAACGACATG TTTTTATTTA TCTGTTTAAT    33000

GTATTTCTTT TCCTCACTTG TCCATGAAGG GAAGGACCAT ATGTGTTGTT ATCCTTTGTG    33060

CAGTTCCTGG AACATAATAA GTATATAAGA AATAGTTTCT GAATTAGCTG TGAATGAATT    33120

CATGCCTTCC TGCTGTCTGT CAATGTTCTT TTAAATTAAA CATCTAAGAC AGCAAATAAT    33180

ACCACATGAG TTATTAACCT GAGAAATAAT CGTTTTATTT ATAAATGACT GAGTTGAAAG    33240

CTGATAGCCC ACAGTAATTG CTTTCATGGC TTTGAATATA AACCTTACTG TTACAAAACA    33300

CATTTTCATG AAAATGAATG TGTGGTGTTT GGAACTAGCT TTAATGTTTG TCTTCCTGTT    33360
```

```
TTTCCTTCTA GTTGCTATAA TATAATAAGG AATTTTGTAT GTTTTTCCTA ATTGTACCCA    33420

CTTTTCTACA TTTTCTTAAC AGATCTGGTG AATCTTCATT ATTAAATATA ATTATACATA    33480

TAAATTATTG TTTAATAATA ATATTAATTA TTAAAAATAA TATAAATTAT TAAATATAAA    33540

GATACATATA ATATTATCTG TTAATTTCTA AGTTAGGTGT GGGTTCTGAA GACTATTATA    33600

TGAATGAACA AAAAGCTTGC ATATTTGCGT GGAAGCTGAA AGTACGAAAT TTTTAGATAC    33660

CATTATACCA GTATCTAAAG AAAAAATTCA GTACCACATA GGTTTTTAAG TAGGAGCTGT    33720

ATGATCATAG GTCATCCAGA TGAAGGAAGG CTTCTGTACC AGACGTACAG AGGTAGACAG    33780

TGTTGTCTGA GTACTGTCTG AGATCTGGCA AGAATGAATC CAATAAACGT AGTTTTCTCC    33840

CATGAGCTCC TGTCTTGTTT CCTGTATTCT GTTTGTATTT GAAAAGATTT GGTGTGCATA    33900

ACTTATTTTT GTCTTTTGGC TGTCAATCAA AGTTATTAGT GTAGTTTTTG TAACTCAGTT    33960

CTCAAGCTAG GAGTTTTTGC TGTATAATTT TAATGTTTCT GTTTTTACTT TCCTAAGCAG    34020

ATAAGCGTAA AAACTTAGAC TAATTGATTA CTTATTAAAC GTCCAGCTTG ATATTCTTCT    34080

TTATATTATT TTAGTTTCAG TTTATATAAC AAATGAGGTT TCTTATAAAT AAAATTTAAA    34140

ATGCACTAAA GGAGCTGTGT GAAATAGGAA TTCTGTGTGA AGCTTTTGAA TGTGAACATT    34200

TAGAACGTTT CACATGGTGG GAATTTACTA TATGATTTTC ATCAAATGAG GTACTTTTTA    34260

GTGTTGGTAC TTAACGATAC TGATTTCTAA AATTTGTATT TCTAAAAATG ACGTATTACA    34320

GGATCTGAAA GGGCAAAAAC TCATTGAGGC TTTGTATGAG TCAGCGTTTC ATGGCCTATT    34380

TTTAATTAGT GAATTATTAG CATATAATTA GAAATGTTTT TAGATTCTTC ATGGCTGACC    34440

TACCAATGAA TGTAGCACTG CATTTAAAAT ATAGTTCACG TTATGTTCAT ACTTAATTGT    34500

TGCATTTTGT TTGCCCCTCT TGAAACGAAG GTCACATGTA AATAAATATA CATTTTCTCC    34560

TACTGTAGGA AATACTCTGT TAGCATTAGT AGGTTTAGCT TTTTTAGGTT AACAATAACA    34620

AAAACAAAGC TCACACAAAA TAAACCAAAT TTGCTCTATG TCCCACAGAT GTATCTTGTG    34680

ATTTTTCCAG AAGGTACAAG GTATAATCCA GAGCAAACAA AAGTCCTTTC AGCTAGTCAG    34740

GCATTTGCTG CCCAACGTGG TAAGTAAAAA TTTGAGTGTT TGAACAAATA ATTTTCAAAG    34800

ATAATAACAT TTTTAGTTTT TCTTCCTGGA AAAGATACTT TTGTTTTACA GTTGAAGGAA    34860

TGAATGTATT CATTCCTTGA ATTAGTGTAC ATATTATCTC TTAGGAAATG AAGTTTCTTC    34920

TCCTTAATTC ACTTTCATGC TATTATTACA TATATCTGAG AAATTAAGTT GAAGTGCTTG    34980

TTACGATACA TATTCTTGTG CCATGGATTT ATTTAAAATC TATCTAAGTA CATGATTATG    35040

TAGATGGAAG CTTTTTCTAC AGTGTATGGG TTATATGTAA TGGAGCTTCT GTTTTGTAAG    35100

ATGACAGACC TAAGTTGGAG TCCAAACTCG TACTTTTATT AGCTGTATGG TTGCAACTTG    35160

GAAGTTGTGT AATGTTGCTG AGCTTGCTTC TTCATCTCTT AAAAGAACAT ATGCCTTATA    35220

AGTAGATCTA AATCTGTGTG AGGATTAGAT TAGAAAATAT GTCAAGTTTC TATTGGAGAA    35280

GTTACACAAA GTTGGTCCAC AGTGCTTGGA AGCTGTTAAT GTCTTCAACA ATGGTAATGT    35340

TCTTAATATC CATATTTTAG AAAATTGAAT AATTGGTACA CCAATAAGCT ATGCAATTTA    35400

ACCAAATTGG GAAGTATACA GAAAACAGTG GCTATGCTAT GTTCTTAGAG GTGTCTTTGA    35460

AGCTTGACTG TGATTTAGTG TGTGATCTCC ATATGTTGAT AGTCACTCAC TGAGCAAATA    35520

CCTTGTTGGT GACATTACAG CAGGGCCTAT GACAGTGCTG TCTAATGGAA CTTTCTGCAA    35580

TAATGGTAAA GTTCTTCATC TGTTCTGTCC AGTGTGCTGG CTCCTACCAA TGTGGTTTTT    35640

GAGCATTCAA CATGTGACTA GTGCATGAAA CTAATTTTTA ATTTTATTTA ATTTAGTTT    35700

AATTAAAAAT AAGGGGGAGT TTTTACAAGG TGCTTACAAG AGCAGATATG TCATAGGTAT    35760
```

-continued

| | | | | | |
|---|---|---|---|---|---|
|ATGACATCAT|TTGTAACAGT|ACTTTTAAAA|AATGCCAGTT|TGTTTTTAAA|CACATGTCCT|35820|
|ATTAAGTAAG|GAGTGTTTCA|GAATAGGAGG|GTTCAGTTGG|TCTCCCCATC|TGCCAGCTCT|35880|
|CTTTTGACTT|TCATTGCTTC|CTCTGTCTAA|TAGACATGAC|GTTCTGTCAT|TTCAGTTGCT|35940|
|CTTTTGCAAT|GCCATTGTCT|CTTTTGCCCT|TTTCACATTT|ATTAAACAGA|ACAAAACAAA|36000|
|AACCACTCTC|GAATCTGTAG|TCTACCTTTG|TTGTAAGCAC|TTTTTCCAGT|ACTCACTCTG|36060|
|CCCTCAATTT|GTTTTGGTCT|GATTTGAAAT|TCTCTCCCTA|GACTTCTGTG|GGGCTGTTCT|36120|
|CCATTATCCT|CCCAACTCTC|TGGCGATTAC|TTCCTAGCCT|CCTTTCCAGC|CTCTTTCTGC|36180|
|TTCATTTCTC|CCTGCTACAT|GTGTTATTTC|CAGTGTCAGG|TTTTGGTGTT|TGATTAATTT|36240|
|CACTTTTTGT|TTCTCATGGT|GGCCTTCCTC|TAAATCCATG|GCTTTAGCCA|TCGTTTCCTT|36300|
|GACTGCTGAT|GACTCGCAAA|AGCTTCCTCC|CCTCCATGTC|TCTCTGCCTA|ACTCTGGACC|36360|
|CATTTGTACA|ATTGTCCATT|AGAGAGCTTC|GCTTGACTGG|CCCAAAAGGA|TGTCTCAAAC|36420|
|TCAGCATATT|GAAGATAGAA|TTTATCCTTC|CATGCATACA|CTCATATTTC|TTGTCTTGGT|36480|
|AACTCCATCA|TTCAGTTTTT|TTGCCTAAGT|TTTATTCACA|AAAAGAACAA|ATTGATAGCA|36540|
|GTTGCATACC|TCTTATAGGA|AACTTAGACA|TGGAGGAAGA|AGCTGTTCAG|ATGGGGTCCT|36600|
|GCAGAAGTGC|AGGCACTGTG|GTAATATTTA|AACTTTTCTC|AGCTGTTCGA|AGGGTTTTGT|36660|
|TTTAACTAAT|TTTCCTTAGA|CTTGTTTTAG|GTATTTGGCT|TTCTAATGGT|TATAAGGGAT|36720|
|GTGGAATTAA|ATGTATCTTA|ATCTGCCACC|TGGACCCATT|AAAGTAAGCC|CCTATGGTGG|36780|
|TTTTTTTTTT|TAATTGCCAT|GGTTAAAACC|ATAGTTGCTA|GCGAAGGTGA|CATACTTAAG|36840|
|CTTTTTGAAC|TCTCTTAAAA|GAAAACAGAA|ATTTAATGAT|GTGTCTATAA|TGGCAAACCA|36900|
|GATACCTAGA|ATTTCCATGT|TATTCATAGG|GTGAATAACA|CTGGCGATTG|TAGAGATTTG|36960|
|AGAGTTCTTT|CAAAACAGGA|GAACAAAGGG|AATAAGCTAC|AAAGCAATTT|TTTTCTTTGT|37020|
|AGACTTAACT|GAATAAAAAT|TATTTTTATG|TCTCAAACAT|CATATGAACA|AATTTAGTTG|37080|
|GCAAATGGCA|AGCTAATAAT|ATTTTATAAT|ATAGGATATT|AATATACTTA|ATATTACAAA|37140|
|AGTGCTTCAT|AATTAGAAAA|GACATAAACT|AGAAAAATGG|GAAAAGGGCA|TGAATAAGAA|37200|
|ATTCAAGAGA|TACAAATGAC|CCACACACTT|GAACAAATGT|TTATTCTTTC|TCATAATCAA|37260|
|AGAAGTAGAA|ATTAAATGAA|TACTTTGAAG|CCAACTTCTG|AGAAAGCATA|GCAAACAAGA|37320|
|AAGCTAGTGC|TCAGCTTTGT|GTGGTAACGG|CACTCTCGCT|CTTAAGAAGG|TGTGTTTGCT|37380|
|CCCTGTGGCT|GCTCTCAGGC|AGGGCCACAA|ACTTGGTGGC|TTAAAACACC|ACAGATTCT|37440|
|TCTCTTACAT|TTGAGAAGTC|TGAAATGGGT|CTTACTCAGC|TGAAATCAAG|GTGTTGGCAG|37500|
|GGCTGCAGTC|CTTTGTGGAG|GCTTGGGGGG|ATCTTGTTCT|CCTGTACGGG|GTCCTGTGCT|37560|
|TGGTTCGGGG|TCCTGTGCTT|GGTCTGGGAT|CCTGTGCTTG|GTTCGAGGTC|CTGTGCTGGG|37620|
|TCCAGTGCTC|TGCTTTTACC|ACCTTGAAGT|TCATCTGGAA|ATGGCACTGG|CTCGCCCACA|37680|
|CCATATAGCT|GACTCTGGTT|CTCCCTCCTC|CTCACTCGCT|CTAAACCTGT|GTTTTTGGCT|37740|
|GATTTCTAAT|CTCTCTTTCC|TTGGCCCTTC|TGCAGCTTGC|AGGGCCTTCT|GCAGCTCTTG|37800|
|TCTGCCCCAG|CCCCGGGGTC|TGCCCATCCC|AGTGCTGGGC|TGTTCTGTTC|CTGCCCTGCC|37860|
|TTTCCTCAGC|CCTTGGCAAC|CCTGTTTGTT|TTCTCCCTTC|CTTAGCAGTG|GAGAACATCG|37920|
|TAAGATCAAT|GCTGACTGCC|TTCTGCAGCC|AAGCCAGGCC|ATTTCATTTC|AGCCGAGCCA|37980|
|AGTCTGTGTG|GAGCAGTTCT|TTTATTTTTC|TCCTTTTGAC|TACCTCATGG|TTTTCACGGA|38040|
|TTTTTGTTCT|CTTCACATTC|AAGGATTTTT|TGCTTTCAGA|AAGTTATATT|TCTCTGGAAA|38100|
|GAGTGCACCC|AATATCCCTT|TTGATTTCAA|AATCTTAATG|TGGAGTCTCT|TGACTTGGAT|38160|

```
TTCTTTGGAA GAAACTGCTG AAGCTGCCAT GTCTAAGAAG AAAACTTTGG AGAAAAATTT    38220

TCTTCTTAGA CATGGCAACG TCAACAGTTT CTAAGCTCTT GATTCCGTCT ACCCTGTCTC    38280

CATCGTTGCC TCAGTCATCT GCCTTACTTC TCTGCAGGGG TTTCTCCCAG CTTGCAAATG    38340

TACTCCAATT CTGAAATAAC TAAGTCTATA GCTGTGCAAA GAGAAGTCTG GGCCCCTTGC    38400

TTTCTTGTGT TTGACTCCAT CCACTCTCCA GAAATGAATC CCACTTCTCA CTTAACCACT    38460

GACCTCCAAA GCATCGTATC ATTTGTGTCA GTTGTCATAT TTGTTAACTT TCACATAACT    38520

TTTGACATTA TTTATACCTT TATAACCAGG AAATAATTTT AACTTTATTG TAGAAATAAA    38580

CAATGGAGTA TAATTTTTCT TGTTGAAGAT AAATATCACC TCCTCTTCCT TTAAACATCT    38640

CTTCCCTTTG TTTTTGTATT ACATTGGTTT CCCCCCTTTT TTTATTTCCT GGGTTGTCGT    38700

ATTCCCTGTT ATTATTTTTA CCTTTTTTTT TTTAATGTGG ATGTTTCCGG AGTCTGTATT    38760

TCTTGCCTTT TCATCTTCTG CCCTTTATTA TTCTCAGCCA CTGCCATTAC TTCAGTTATC    38820

CATTCCCATG GTTTCCACAT GCTTAGCTTC GGTTGATTCT TGCCATTTTA CAGACCATAT    38880

TTCCAACTAC TTCTAGAATG TTTTGTTCCT TCAGCCTCAG TATGCCCAAT TGAACTCAT    38940

GTTCTCTCTC CCCCTTCTTT CTTCCTTCTT TCTTTCGCTC TCTCTCCCTT CCTTCTTTTC    39000

TTTCCCTCCC TCCCTTTCTT CCTTCCCTCA CTCGTTCTCT CTTGCTTGCT TGCTTTCTCT    39060

CCTCTCTCTC TTTTCTTTCT GCNNNNNNNN NNNATTCTTC TCCCTCCCTC TCTTCCTTCT    39120

CTCCCCCACT CCCCAACTTC CAGGCTAAAG CAGTCCTCCT GAGTAGTTAG GACTACAGAC    39180

ATACACGTGC CACCGCGCCC AGCTCCGTGT TCTCTTTGTT TCCCTGCCTC CTGCTCTTCC    39240

ACTTATCTTT GCATGGCAGG TGGGTGCACG CAGGCATGCT CTGCATGTCT TCCTCTTGGC    39300

CATTCCCCTT CTAGTTATGG TGTGGCTTTA TCTACGCGTT CTGGAGCAGA AGCCTAGTCA    39360

CAAAGCTATT TTTTTAAAAC ATTCATGATA ATTCATTTCC TTTTATGTTT TAAAAATACT    39420

AGCTTTCTGT CTTTATTTCC TTACTAACTT ACTTGGATGC CAGTAATTAG TTGTTTTAGT    39480

GAACACCACA GAGTGATATT TGAAACTTTT GGACTTCATA AAGTTGGATG AGCTCCAGTA    39540

GCAAAGAAGG AAGTGTTAAC TAGTTTAACT GACAAATAAA TGCTTCCCAG CTTGGTGTGC    39600

GATTGAGATT TTTGTTGCAA GTTTGTGAAT CAATTTAACT GCCCCTGCCC TGGGGACTAA    39660

AGTCAGATAC GTGCTTGTGG GAATCTTTGT CTTTCCCACA CCACCCTGCA TTTTAAAACC    39720

TCTTGTGTGG GACAGTCCCA CCATGTAATA GCTGTTCTTC CTTACTCAGC TACTTTCCCT    39780

CCAGAGAGGC CAGTAGAAAA TCTAGACTAG TTTTTTATAG TCTATTTTCA TGTCACTTAT    39840

TGAGAGCTAC TGTTTTCTGT TAAATTGTCA GTAAATATTT TAATCAAGGA AAAGGGAGGC    39900

AATAGGAAGG AGAGAAGAAC AAATCCTTAA CCCTAGTAGG AACCTAATGA ATGGGATTTG    39960

TTCTGGATAA TTGCAGTAGT CCCCCAGCTA AAGAACCTTT TAAAAATATG TCAGATATAC    40020

CCAAGAGGAT TGAAATCGTA TGTTCATACA AAAGCTTGTT CACCTGCAGC CTTCATATGC    40080

AATTCCTATG AATGTTCATA GCAGCATTAT TCATAATAGC CAAAGTATGG ATGCAACCCA    40140

AATGTCCATG AAGCAATTAA TAGGTAAACA AAATGTGATC TGTTCACACA GTGGAATACT    40200

AACTATTCAG CCATAAAAAG GAATGAAGCA CTGAGTCCTG CAGCCACACA GATGAACCTC    40260

AGATCCATGC TGAGCGAAAG AAGCCAGAAA CAGGAGGCCA TGTGCTGTGT GACTGTATTT    40320

CTAGGAAATC TTGAGTCACC ATGGGCAAGA TGCTATCACC TTTGTTCAGT GGCCAGAAGC    40380

GAGGGCACTA ATATTTACCC TTGCCGGGGT CTACTAGATT GAAGCGTTTC CGCTAGGCCA    40440

TAAACTTCCA ACACGGTGAC TTGTACATGT AGATATTTGA TCAATATATA GCAAATGAAT    40500

ATTGATTTAA ACAGAAAAAG GCAAGTGAGA GTGCTTTCTA AACTTAGAGC CCTAAATATA    40560
```

```
TGAGGTTGTG GAATTAATAG ATTCTGTTGT GTGTGTTTGA GGGAATTTAA AAATAATTTA    40620

GATGTTAAAC AGTATATTGT GGAGGTGTTT TGTAACTAAT TAATGACGGC ACTGAATTGA    40680

CTTCTAGGCC TTGCAGTATT AAAACATGTG CTAACACCAC GAATAAAGGC AACTCACGTT    40740

GCTTTTGATT GCATGAAGAA TTATTTAGAT GCAATTTATG ATGTTACGGT GGTTTATGAA    40800

GGGAAAGACG ATGGAGGGCA GCGAAGAGAG TCACCGACCA TGACGGGTAA GTGTGTTCAC    40860

GCACCTGAAA TGCCTGTACA CGGTATATAC AGTGCACATG TTTATGTAGA ATTCAGTTTT    40920

ACAAAGTAGG TTAAGTGTAC TTTTTTCCTC CATTACATTT ACCCGGTATA TTTTTCAAGA    40980

TGTTATTAAG ATGTAACAGT GGAGATTTCA TTAGTCCTGC AAAGTGTGGT ATTTCTTGGC    41040

TGTCGTGTGA GTCCTGTGGA CTCACCAATT ATCATTAATC CAGCCTCTTT CTACTCAAAG    41100

TTCACACTTA AAAGGAAAGC TCTGTAAAAG GGAGGAAGAC GTGAAGAAGG AGCACGCCTG    41160

GCAGTACTGA GTGCACGTTA TTAGTCAGTG CTGCCCTTTT GCTGTATTTT TCGTAAAATA    41220

TTTATTAAAT TTGGGTGTCA TTGTGACAAG AAGAAATGCA GTTAAGTGTG ACCTTTTTTT    41280

TTCCCCAAAC ATGTTAGGTT TTAAGAACCT TTGAGCTATT GTCAGATATA ACCAGAAAAA    41340

AATAGAATTT TAAGTGAGCA GGATAACTTA GTTAAACTAA CCAAACATAG TGTTAGCTGT    41400

TAGAGAAATG TAAACATGGA AATAGGCAAA CAGGGAAGTG TGTGGAGTTT CTGTTTCCTT    41460

TTCAAAATAT CTGTTTGAGC TGGGGTTGAG AGAGAACACT AGGCTTCATG GGGTTTTTTT    41520

GTTTTTCGTT TTTTGTTTTG AGACAAGAGT TTCGCTCTGT CGCCCAGGCT GGAGTGCAGT    41580

GGCGCAATCT TGGCTCACTG CAACCTCCGC CTCCCACGTT CACACGATTC TCCTGCCTTA    41640

GCCTCCTGAG TAGCTGGAAC TACATGCGTG TGCCACCATG CATGACTAAT ATTTGTATTT    41700

TTAGTAGATA TGGGATTTCA CCTTGTTGGC CAGGCTGGTC TCAAACTCCT TACCTCAGGT    41760

GATCCACGCA CCTCGGCCTC CCAAATGAGC TTTGTGTTTT TACCTCATCA GCTGTTTGGG    41820

GTTGAGCCAC TATGTATGTC AGTGTGCTTG TATCAGTAGG ATCTACTGAG GGCAGATGTT    41880

CAAAATATGA GCCTCCAGCA CGTTTTACAT GGAAACCCTC ACCTGAAGCA TTCGTCTGAA    41940

GTTGATGTGC CTTGGAAATT TTATAGAGTA ATATTTTTAA CTACAACAAA ACATTTATAA    42000

AAGTAGACAT TATTAAAGCA TTCAGAAGTG AGCAAGGATA GAAATTATTC TGCCCAACCT    42060

TACACGTAGG CCTTCTAGAC GTAGTACTGT GCACCGTTAC ATTATCTAAC ACTGTCTGTG    42120

TGTCATCTTT GGATGTTAGG GATTTTTCCA AAGTTCAGTG AGATTATAGT TGTCAAATGA    42180

TTAGTCTGTT AAATAATGAT AAGATGAGGG TCACTCAGGT TTTAAAAGAA AAGCTCTTTG    42240

ACTGAAAGAG AGAGCAGCTG TCTACTGCAG AAAGTTAGGG AGGGAGGCTG GAGGAGTGAG    42300

GCCCAGGGGC TAGCTAGTAT AAAAATTGGT TATGGTCGAA GGAAAAAAAA ATGTAACATA    42360

TTTATATCTG AAAGATGATT GTTCTCATAA TTGTATATAA CACAGAGTAA TTGTAAAGTA    42420

GAAAACTAAG GTGTTTTTCA TTTTAGATGT AAATGTTTAG AATATGTAAT GCATCAGTTT    42480

AAAAATTAAA ACTGTACGAA ATGCACAGTG AAACGTCTTC CTTGCTTTCC ACCCTGCTAC    42540

CTGGCCTTCC CTTCTCCTTC CTAGCGATAA CCAGTTTTCT TAATTTGTTG TGCGTTGTAT    42600

GTGCAAATTT AAGTATATCT TCTTATTCTA CCATCCCTCC CTTCTTACAG AAAAGTGGCA    42660

TATTAATATT TTTCTCTTTT AAACTATCGA AGGAGTTACT TACCTATTTT TGCATTTCAA    42720

AACAGACAGT TCATCAAGAT TGTCGTTGGT TTATTAAACA TAGTTTAAGA TTAAACAAGT    42780

GTTTATAACC AATGAAAAAC AGATAGACTC CCCATAATAA CCTTGTTTAA ATGCTGCTAC    42840

TTTTATCATG TCCCCTCCTG TCTAAGAACC CCTTGGTTCA GCAGAGCTCA TGGGTAAGGC    42900

CAGCCTCTGT TGCCTGCCAT CGGAGGAATG CGTTCCAGCC GTGATCTCTG CCTTGCCTTC    42960
```

```
GCTTCCTCCT GTGCTGTGCC GTGAAGCCTC GGCCGTGGTG AAGCTGGCTG ACTGAGTCCT    43020

CCTGCACCCC ATGCATATTC AGTAGTTGAA GGCTTTGTGT GGCCAATCCT GCTTTCCACA    43080

GGAAACCACC CTCTCTTTTG TTGCCCTCAT CCAAGGCTAC TGTTCTCCCA GAGTGACAGG    43140

CGGCACCTTT CCCAGCATAG CACTGTGCCT TCTCCTGCCC CTGCTCTTGC AGTACTGCTG    43200

TGGCACTGAT GGCGTGTGTT ACAGTGCTGG CACTTAGCAC AGGGCTCTGC CTTTCTCTCT    43260

TCCCAGCCGC ATCATAAGTG CCTTGAGGAA GCCAAAACCT TCTGTGAGTT GCATTGCCTG    43320

GGTTCCAACC TCCCACTGCC CTGCTTATCC TCTGCTACAT GTGAGCTGAC TGTGGCTTTG    43380

GGGTGGTCAC TGCCTATGTG TATTCATTAC AAATTGTCTC CTTTTGAAAG ATTGACCTTT    43440

CTGACTTACC CAGATACCAT AAAGAAAATA AAATCTTATC ACTTCAGTCA AGGATAAAGT    43500

ATTTCTGAAT TAAAGGAAAA ATACACCAGA GTAAAATCAA GACTGAAAGA CAAACTGGGA    43560

AATTATTTGC AACCTAGATC ATAGAAAAGG GGTCATTTCC TTCTTGCGTA AAGTGCACTT    43620

ACAAATTGAT AAGAAGATGA CTGATAACTA GAAAGAAAAA TGGGTAAAGA ACAACAATAG    43680

ACATTTCACA TTTAACCTCA TTCATGATAA GGTAAGTGCA AATGAAAACT ACAGGGGATA    43740

CCTTTTTTTT TTTTTAATCC ATTAGATTGG CAAACATCCC AAGGTTTGAT CATAGGCTCA    43800

GTGGGTGAGA TTTAAGTATT ATCAGGCATT TTTATACTTT GCTGTTAGGA ATGCAATGTA    43860

GTACAAACCT TTGTAGAAGT TGCTTTGGAA ATGTCTCTCA GATGTACAAA TGCATTCACA    43920

TTTTAGATTT AGCATTCCCG CTTTCTGAGA CATTATTCAA CATGTATACG TGTGCACATA    43980

AGATATAATA ATAACACGTT TTTCCTTCTA GTGTGTTGCT TTTAACCTGT AGCTTGAAAA    44040

AACTCTGCTT TCATTGTTTT TTTTTGTTTT CTGTCACTGG CTCAGCCCTG CTTTCAATTG    44100

TTTATATGAA TTGATGGGTG TTCTGGTCTG GTTATAATCT ACTTTAGTTT AAGAGTCACT    44160

TTAAATTATA TGACATCTGA TATAAGTTGT GTTAGGTAGA AAATTCTGTA ACTTGGAATA    44220

CTGTAAGTAC TTTGTGGCCA CATTTCATTA GTATTAAATA TTATCTCTAT ATATAGTAGG    44280

CTATTTAATA TTCATATTTT ATGATGCAAT TAAGAAATAA TTTTTTTCTG AAGTTGGTAG    44340

ATTGTTGATA TGCCATGGCC CAGTGTTTCT CAAAGCATTC TGGGGGATCA CTGTTTGTCA    44400

GAATTAGCTG CAGTGATTGT TGAACATGCA GGGCCTCTGC TCCACTCCAC GTTGCTACCA    44460

GGACGCTCTG CAGGTGAGAG CTGGGAAGCT GTAGAAGCTG CAGTGCTAAC AAATGCTACA    44520

GGAATTCTTG TAGTCACCTT CATGAGGTCT TATGTTGAGG AGAGGCAGCC AGTAGTGTCC    44580

CTTGTCCTTC CCGTTTTATG GTGTAAGTTT CATTTTAAGG GAGGTATAAA TCAAAGCCCA    44640

CCTGGGCATT CTCTCATGGT TCACTGCTTC TTGTAATCAT GGAAGATGTC ATTGCGGCAG    44700

AGACGAAACA GTGTAGTTTG ATTACTATTG ATTTTTTTTT AATTATTTTT CTGAAGTGGC    44760

TGTTGTAATG TAATAAATTG TGTGCTTAAG GACAACCTTT GGTATTCTAT TTGAGTATTG    44820

TGTATGATCC TAGTTAAGTT TTTTCTACCA GTATTTTCAT ATTACAACAT ATTTACTTTC    44880

CATTTCTATT AATATTTTTA TATTTAAAGT ATGGAGGCCG GGCACAGTGG CTCACGCGTG    44940

TAATCCCAGC ATTTTGGGAT GCTGAGGCGG GTGGATCACA AGGTCAGGAG TTCTAGACCA    45000

GCGTGACCAA CACGGTGAAA TCCCATCTCT ACTAAAAATA CAAAAATTAG CCGGGCACAG    45060

TGGTAGGCAC CTGTAATTCC AGCTACTCAG GAGGCTGAGG TAGGAGAATC ACTTGAATCC    45120

GGGAGGCAGC AGTTGCAGTG AGCTAAGATC GTGCCACTGG ACTCTAGCCT GGCTGACAGA    45180

GCAAGAATCC GCCTAAAAAA AAAGGGATCA GGGAAGAGGG GATTACAGAT AACCCAAAGA    45240

AGAAGGAAAA ATCTCCACAA GTTCACCTGT CCAGCGGTAA CCCCAATTTG GATATTTCC     45300

TTTAACAATT TGGATATTTT CCTTTAAATC CTCTTTTTTA TAATGTCTAT ATGTTGGAGA    45360
```

```
GAGTATGTGC CTTTACGTAT TTTTTAAAGA TGAGATTTCT GTGTGTGTCT ATATCTCCTG    45420

TTCTTCATAT TTTCTTGTGT GTTATAAACA GCTGTACATG TCAGTATATA TACTTCCGTA    45480

ACTTTTTTTT AAAGGCTATA TAGTGTTCAT TGATGTGATT TAACAGCAGT TATCTCCCCG    45540

GCTTCATCTT GTTGGAATGT GGGTCCTGTG TGTTGCCTTC AGAGCAAATG GGGCTTGGTT    45600

TTGCAGCAAG TAGACCTGTG ACCTGTACGA ATAGTTGGAA GACTTTCTCT ATTACCCAAG    45660

CGTATCAGTA TACTTTAGTG CCTACTAGAA ATTTATGGGT AGAAAAACAA TAATATCTTA    45720

GAGTATTTTT TCCTAGATTC CCTAAGGTGC TATAGGGTGA TTTTTACTCA TGTAACATGA    45780

ACTATGCTTC AACTAAGATA GTTTTTGCAA ATGTGGATAT ATAAGTACTT TATTAAACCT    45840

ATAGGAAGTA TTTATACCAC TTATTTCCTC CCTTCAGTGT TAGAACCTCC TAAATGGCAT    45900

TTGACATTGA ACTGCTTTCC ACTTTGTCGC ATGCTCCTCT CATTGTCCCT ACCTGGGTCC    45960

TGAACCTTAG GGACTTGGCT GTTATAGCCC CACCATGGCT ACGCTGGGCC TTGGTCGTCT    46020

CTGAGACTTA GTTTCTTCAT CTTACAAGGA GATAATAACA GCCCCTGCCT GCGTAGAATT    46080

GCAGAGATCA AATGAAATAA TTAACATACT CAAAAGCATG CCGTAAACAC ATTCTGAGCA    46140

CATGTACGTT TTAGGAAAAA CAAAAGGACC CATGCACATT TCGGAGTGCT TTTGTCTCAG    46200

CAGCACTGCC TCTTCTTCCA AAGCTGACGT CTTAGTAGAG GCCCTGCCAC GTCCTGAGCA    46260

CTGTACTCCA CGAAGCATTC TATTTCTGAC ATTCGAAATG CAGTCTGTTC CATCTTCCTT    46320

ACAATCTGTA TGCCAGCACT TGAAATACCG GGTATCTGCA GTGTTGACCA GGTGATTACT    46380

TAATTATGGA AATGTTGAGG TGGAGATCTA GATAATTCAG TGAAGGCAGG AAAATTGGTG    46440

TCGGAATCTG TCTTTTTATG TGTCAGAAAT AGAAATAAGA TAGGGTGAGA AGTAATTTGT    46500

GGCTAAAACA CTATAATAGC TAACACATAG TGCATACTGT GTGCCAAGCA CTCCTGTAGG    46560

TGCTTGAAAT CTTCTATTAT TATTATCCCT ACTTTATAGA CTTGCACCCT TAGGCACAGA    46620

GAGGCGGACA GTTGTCCAAG GTTACCCCAG AGGTGGAGAT CCAGGCTACC TGACTCCACC    46680

ATGTGTGCTC TTCCCTAGGG CACAGTTGTG CTGCTAAAAA TACTTTTTAA GCAGTTCTTT    46740

GATTATTCAG ATGATAGTAC TGTAGGAAAA TTAAGACAAA AATAATGAAA AATTAAAATC    46800

TTTATTTTAG TGTTTTGCAC ATGTATTATT AAAGCCAGTT TACTCCTGGA AGTGTGTAAG    46860

AATACAGGGT ATTTTTGATC ACCTAAATGC TGCATGTTAC TAAGAGCTCG ACACTGAAGT    46920

CAAGAAGAGC AGTTGCAGAG AGTACTTAGC AAAAACGGGA AGTGTGTGGG GTTGAAGGAG    46980

CAAAGACAAG TCTTCCTCGG ACGGTGGAGT GTAGAATTCA TCATTTCTCA GAACACGTCT    47040

TTGAACGCAT TTTCAATTTG AGGCCAAAGG TCTCAGCCTC CCACTCGGCA TACCTCCCTA    47100

CCTTAGTCAG CTCTTAAATC TTAGGAATAT TTCTTTGTTC TTCAAGGAAC TTAAATATGT    47160

TAACATTCTT ACCTGTCCAC AGGGAGCCCC CTACAAAGAA GGGAGTTTCT AGTCTCCGTT    47220

CTTTCTTGGA ATAAATAATA GCCTCATACC TTGTGCAATC GAGGCTGAAA AAGACTGTCT    47280

CCTTTTTTCA AATAAGCAAG TCTTAGAAAC TACAGTTGTT TACAGGGCTC ATGGCTATTC    47340

CACAGTAATA ATTTTGGTTC TTTTACCAAT TATATAATAT GTTAAAATAT GGCAAGTATC    47400

AGGAAAGCAA GGAGTGGCAA TGATTAGAAA CCAATGGCCA AGTTAGAGAG GAGGGGCAAT    47460

TGCTCCCCCA AGTTTGTTGT GGCTGTGTAG CAGTCAGTGA CGAGAAGCTG TGTGTCAGGC    47520

GACAAGCAAA GTTGAGGATT ATCAGGCGCC TGTGAGTGCC CAGCTGTGTG CCAGGTCAGG    47580

AGGTGCCATC GTGAGCCAGA CCAGCTTCCT CTCGGCCCCT GTGGAGCTCG CAGTCTGGTG    47640

GGGAGGCAGC AGTCACCATG GTGACAGGTG ACACACTAGG ATGGGCTGG TGGTGGTAGG    47700

CATTTGCGGG TCCCTTCAGA GAGGTGAGTA TGGACTTAGA GGAGGCTCCA GCTTCCTATT    47760
```

-continued

| | |
|---|---|
| CCTGGGCTGT CTATAGCACT AAAAGTTGTC ACATGAAAAA TAACATTTGG TACTATTGAT | 47820 |
| TTAACTTAAT GACTTATGTA ATTGTAGTTG ACTTAGAAAT TATAACATGC TCTTCTACTT | 47880 |
| CAGCTTGAAA CCCCCAACCA CCAGTTTATA ATCCTTTTTT TTTAACTTTT GTTTATTTTT | 47940 |
| CCTAAGGAAT CTGTACTTTT TCTTCATTTT ACAACTTTTT TTGTCCTGTT ACCTTATTTT | 48000 |
| CATTTTTACT TTATATGACC ATGAGTTCTA AAATAGTAAA AAAAAAGAAT TATTTTTGTT | 48060 |
| CTTTGTTAGA ATTTCTCTGC AAAGAATGTC CAAAAATTCA TATTCACATT GATCGTATCG | 48120 |
| ACAAAAAAGA TGTCCCAGAA GAACAAGAAC ATATGAGAAG ATGGCTGCAT GAACGTTTCG | 48180 |
| AAATCAAAGA TAAGTGAGTA ACAACAGTTC CAGCACTTCC GGAACTTCGG TTCAACTAGA | 48240 |
| TTTCAGTATA GTCAACAATT TGAAACCAAT GTAAATGGTT ATATTGTCTC AAGAATACAT | 48300 |
| TTTATAAATT CAAATCAAAT TTTATGCATG TCTGATCGTG TTTTAAACTT TACTTGTACA | 48360 |
| AATCAGTCTA AAAGAACTTG TTACAGTGGG CCCATCTACT TGCATTGATA GTATTTCTTG | 48420 |
| GACAATACTA CGTGATAACA TAGCAAATTA AATTAAAAAC AACAACAAAC ACACAAAAAA | 48480 |
| ACTTTCCAGT GTCAGATGCC CGGACCTACC TGTCAGGTCA CATAAAGTGG TGTTACTGTG | 48540 |
| TGAGGTCTGG CTGTTGGGCC AGTGTGCGCA GAAAAGCAAG GGAGGGGTAG AGGACTATGC | 48600 |
| GGACGTGCAG GTGGACATGA TGCTGTTATA TTTGTTGGAA ATAGAAGGGG GCAGTTGACA | 48660 |
| GCGTTATATC CAAAGTGTCT TCTGTGGTTA ATTATATTCA GAAATTTTAG CCAATTGTTT | 48720 |
| TATTCTCTAA ATATGTACTT TCTGCTCAAG AAACTATCAT TGTTCTTCTT TTCCTTGTTT | 48780 |
| TACAGTACAG TGTTTTTAAT TAACCCTCCT GGGTTAACTT TACCAGGTGA AAATGATTAA | 48840 |
| AAGTGTAATA GGTTAACAAT GAAACTTTAA GCTTCTATTT TTCATTGACT CTTAACTGTA | 48900 |
| CATGATGTAA TGTATTCAGC GAGCCATTCA GGACCACTTT GGCCCATGGA AGAAATTTAA | 48960 |
| AAGTAAGATC TACATGTATT GACATGAAAA TATGTTCTCA GAAAAAGAC TAATGTATTT | 49020 |
| AATGTCCTAC TTATTTTATA AGTATTTAGA ATACCTCTGG ACATTTTAAA ACAATGATTA | 49080 |
| TTGCTAGGGT GTGTGATTTA TAAAGCAATA GAAGCGCTTT CCCTTTCTGT TTGTGTTTTA | 49140 |
| GATTATTATA TCGGGTATGT TCTGCTATCA TAACTTTACA AATCTTATGT AATATGGGAA | 49200 |
| AATGAGTTAA CTATGCTGTT TTCCTTCTTT TACCTGCCTT TCTAATTCTG TGGGAATAAA | 49260 |
| GGCGTTTTTG AGACAGCCCA GGTGTAGTGA GCAGTCCATA TCCATGGATT CCACATTCAT | 49320 |
| GGATTCCACC AAGCACAGAC CAAAAATACT CAGAAAAAAA GGGGGCTGGC TGTGGTGGCT | 49380 |
| CATGCATGTA ATCCCAGCAC TTTGGGAGGC TAAGGCAGGC AAATTGCTTG AGCCCAGAAG | 49440 |
| TTCAAGACAG CCTGGGCAAC ATGGCAAAAC CCTGTCTCTA CAGAAAATAC AAAAATTAGC | 49500 |
| CAGGCGTGCA CCTGTAGTCC CAGCTACTCA GGAGGCCGAG GTGCGAGGAT CACCTGAGCC | 49560 |
| TGGAAGGTTG AGACTGCAGT GAGCTATCAT TGTGCCAACT CCAGCCTGGT AACAGAGTGC | 49620 |
| CTTTTTTCAA AAAAAAAAAA AAAAAAGGAT TTGGGAGGAT ATGCATATGT TATATTCAAA | 49680 |
| TACATGCCAT TTTATTCATA TATCAGGGAC TTGAGCATCC TTTGATCTTG GTCTCTGCCG | 49740 |
| GGTATCCTGG GACCAGCCCC CTGTCGATAC AGAGGGACCG CTGTCTAAGA ACCGCTGGTC | 49800 |
| CTATCTTTGA CTTCTGGCGG AATAGGAGCT CCATGTAAAA AGGAGGAGAA GCTGCAGCGG | 49860 |
| GTTATTAGCC ATTTGTGAGT CAGGTCACTG TAAAACTTTA TCAAAAGTTT AAAAGACAAA | 49920 |
| AAGCATCCTC ATAAAATGCC TTAAAACCAC CTGTTGAAAT ATTACATATA CAATTCATGT | 49980 |
| ATACTAATCA TAGAGCATAT TAAAGATATT TTAGAAGACT AGAAACTTCT ATTAAACCAA | 50040 |
| GTTTCTGGAT GTTTCCGTAT TCATCCTTAT TTTCCAGGGA CCTGCATAAC TTTTCCAGCG | 50100 |
| TGTAATAGCT ACCTGATTGA TATTTTTTGA ATTGAAATAC TGAAGTGACT AAAATCTAAA | 50160 |

```
CTTTTTCCAT TCTGGCCATA GGATGCTTAT AGAATTTTAT GAGTCACCAG ATCCAGAAAG   50220

AAGAAAAAGA TTTCCTGGGA AAAGTGTTAA TTCCAAATTA AGTATCAAGA AGACTTTACC   50280

ATCAATGTTG ATCTTAAGTG GTTTGACTGC AGGCATGCTT ATGACCGATG CTGGAAGGAA   50340

GCTGTATGTG AACACCTGGA TATATGGAAC CCTACTTGGC TGCCTGTGGG TTACTATTAA   50400

AGCATAGACA AGTAGCTGTC TCCAGACAGT GGGATGTGCT ACATTGTCTA TTTTTGGCGG   50460

CTGCACATGA CATCAAATTG TTTCCTGAAT TTATTAAGGA GTGTAAATAA AGCCTTGTTG   50520

ATTGAAGATT GGATAATAGA ATTTGTGACG AAAGCTGATA TGCAATGGTC TTGGGCAAAC   50580

ATACCTGGTT GTACAACTTT AGCATCGGGG CTGCTGGAAG GGTAAAAGCT AAATGGAGTT   50640

TCTCCTGCTC TGTCCATTTC CTATGAACTA ATGACAACTT GAGAAGGCTG GGAGGATTGT   50700

GTATTTTGCA AGTCAGATGG CTGCATTTTT GAGCATTAAT TTGCAGCGTA TTTCACTTTT   50760

TCTGTTATTT TCAATTTATT ACAACTTGAC AGCTCCAAGC TCTTATTACT AAAGTATTTA   50820

GTATCTTGCA GCTAGTTAAT ATTTCATCTT TTGCTTATTT CTACAAGTCA GTGAAATAAA   50880

TTGTATTTAG GAAGTGTCAG GATGTTCAAA GGAAAGGGTA AAAAGTGTTC ATGGGGAAAA   50940

AGCTCTGTTT AGCACATGAT TTTATTGTAT TGCGTTATTA GCTGATTTTA CTCATTTTAT   51000

ATTTGCAAAA TAAATTTCTA ATATTTATTG AAATTGCTTA ATTTGCACAC CCTGTACACA   51060

CAGAAAATGG TATAAAATAT GAGAACGAAG TTTAAAATTG TGACTCTGAT TCATTATAGC   51120

AGAACTTTAA ATTTCCCAGC TTTTTGAAGA TTTAAGCTAC GCTATTAGTA CTTCCCTTTG   51180

TCTGTGCCAT AAGTGCTTGA AAACGTTAAG GTTTTCTGTT TTGTTTTGTT TTTTAATAT   51240

CAAAAGAGTC GGTGTGAACC TTGGTTGGAC CCCAAGTTCA CAAGATTTTT AAGGTGATGA   51300

GAGCCTGCAG ACATTCTGCC TAGATTTACT AGCGTGTGCC TTTTGCCTGC TTCTCTTTGA   51360

TTTCACAGAA TATTCATTCA GAAGTCGCGT TTCTGTAGTG TGGTGGATTC CCACTGGGCT   51420

CTGGTCCTTC CCTTGGATCC CGTCAGTGGT GCTGCTCAGC GGCTTGCACG TAGACTTGCT   51480

AGGAAGAAAT GCAGAGCCAG CCTGTGCTGC CCACTTTCAG AGTTGAACTC TTTAAGCCCT   51540

TGTGAGTGGG CTTCACCAGC TACTGCAGAG GCATTTTGCA TTTGTCTGTG TCAAGAAGTT   51600

CACCTTCTCA AGCCAGTGAA ATACAGACTT AATTCGTCAT GACTGAACGA ATTTGTTTAT   51660

TTCCCATTAG GTTTAGTGGA GCTACACATT AATATGTATC GCCTTAGAGC AAGAGCTGTG   51720

TTCCAGGAAC CAGATCACGA TTTTTAGCCA TGGAACAATA TATCCCATGG GAGAAGACCT   51780

TTCAGTGTGA ACTGTTCTAT TTTTGTGTTA TAATTTAAAC TTCGATTTCC TCATAGTCCT   51840

TTAAGTTGAC ATTTCTGCTT ACTGCTACTG GATTTTTGCT GCAGAAATAT ATCAGTGGCC   51900

CACATTAAAC ATACCAGTTG GATCATGATA AGCAAAATGA AAGAAATAAT GATTAAGGGA   51960

AAATTAAGTG ACTGTGTTAC ACTGCTTCTC CCATGCCAGA GAATAAACTC TTTCAAGCAT   52020

CATCTTTGAA GAGTCGTGTG GTGTGAATTG GTTTGTGTAC ATTAGAATGT ATGCACACAT   52080

CCATGGACAC TCAGGATATA GTTGGCCTAA TAATCGGGGC ATGGGTAAAA CTTATGAAAA   52140

TTTCCTCATG CTGAATTGTA ATTTTCTCTT ACCTGTAAAG TAAAATTTAG ATCAATTCCA   52200

TGTCTTTGTT AAGTACAGGG ATTTAATATA TTTTGAATAT AATGGGTATG TTCTAAATTT   52260

GAACTTTGAG AGGCAATACT GTTGGAATTA TGTGGATTCT AACTCATTTT AACAAGGTAG   52320

CCTGACCTGC ATAAGATCAC TTGAATGTTA GGTTTCATAG AACTATACTA ATCTTCTCAC   52380

AAAAGGTCTA TAAAATACAG TCGTTGAAAA AAATTTTGTA TCAAAATGTT TGGAAAATTA   52440

GAAGCTTCTC CTTAACCTGT ATTGACACTG ACTTGAATTA TTTTCTAAAA TTAAGAGCCG   52500

TATACCTACC TGTAAGTCTT TTCACATATC ATTTAAACTT TTGTTTGTAT TATTACTGAT   52560
```

-continued

```
TTACAGCTTA GTTATTAATT TTTCTTTATA AGAATGCCGT CGATGTGCAT GCTTTTATGT    52620
TTTTCAGAAA AGGGTGTGTT TGGATGAAAG TAAAAAAAAA AATAAAATCT TTCACTGTCT    52680
CTAATGGCTG TGCTGTTTAA CATTTTTTGA CCCTAAAATT CACCAACAGT CTCCCAGTAC    52740
ATAAAATAGG CTTAATGACT GGCCCTGCAT TCTTCACAAT ATTTTTCCCT AAGCTTTGAG    52800
CAAAGTTTTA AAAAAATACA CTAAAATAAT CAAAACTGTT AAGCAGTATA TTAGTTTGGT    52860
TATATAAATT CATCTGCAAT TTATAAGATG CATGGCCGAT GTTAATTTGC TTGGCAATTC    52920
TGTAATCATT AAGTGATCTC AGTGAAACAT GTCAAATGCC TTAAATTAAC TAAGTTGGTG    52980
AATAAAAGTG CCGATCTGGC TAACTCTTAC ACCATACATA CTGATAGTTT TTCATATGTT    53040
TCATTTCCAT GTGATTTTTA AAATTTAGAG TGGCAACAAT TTTGCTTAAT ATGGGTTACA    53100
TAAGCTTTAT TTTTTCCTTT GTTCATAATT ATATTCTTTG AATAGGTCTG TGTCAATCAA    53160
GTGATCTAAC TAGACTGATC ATAGATAGAA GGAAATAAGG CCAAGTTCAA GACCAGCCTG    53220
GGCAACATAT CGAGAACCTG TCTACAAAAA AATTAAAAAA AATTAGCCAG GCATGGTGGC    53280
GTACACTGAG TAGTTTGTCC CAGCTACTCG GGAGGGTGAG GTGGGAGGAT CGCTTCAGCC    53340
CAGGAGGTTG AGATTGCAGT GAGCCATGGA CATACCACTG CACTACAGCC TAGGTAACAG    53400
CACGAGACCC CAACTCTTAG AAAATGAAAA GGAAATATAG AAATATAAAA TTTGCTTATT    53460
ATAGACACAC AGTAACTCCC AGATATGTAC CACAAAAAAT GTGAAAAGAG AGAGAAATGT    53520
CTACCAAAGC AGTATTTTGT GTGTATAATT GCAAGCGCAT AGTAAAATAA TTTTAACCTT    53580
AATTTGTTTT TAGTAGTGTT TAGATTGAAG ATTGAGTGAA ATATTTTCTT GGCAGATATT    53640
CCGTATCTGG TGGAAAGCTA CAATGCAATG TCGTTGTAGT TTTGCATGGC TTGCTTTATA    53700
AACAAGATTT TTTCTCCCTC CTTTTGGGCC AGTTTTCATT ACGAGTAACT CACACTTTTT    53760
GATTAAAGAA CTTGAAATTA CGTTATCACT TAGTATAATT GACATTATAT AGAGACTATG    53820
TAACATGCAA TCATTAGAAT CAAAATTAGT ACTTTGGTCA AAATATTTAC AACATTCACA    53880
TACTTGTCAA ATATTCATGT AATTAACTGA ATTTAAAACC TTCAACTATT ATGAAGTGCT    53940
CGTCTGTACA ATCGCTAATT TACTCAGTTT AGAGTAGCTA CAACTCTTCG ATACTATCAT    54000
CAATATTTGA CATCTTTTCC AATTTGTGTA TGAAAAGTAA ATCTATTCCT GTAGCAACTG    54060
GGGAGTCATA TATGAGGTCA AAGACATATA CCTTGTTATT ATAATATGTA TACTATAATA    54120
ATAGCTGGTT ATCCTGAGCA GGGGAAAAGG TTATTTTTAG GAAAACCACT TCAAATAGAA    54180
AGCTGAAGTA CTTCTAATAT ACTGAGGGAA GTATAATATG TGGAACAAAC TCTCAACAAA    54240
ATGTTTATTG ATGTTGATGA AACAGATCAG TTTTTCCATC CGGATTATTA TTGGTTCATG    54300
ATTTTATATG TGAATATGTA AGATATGTTC TGCAATTTTA TAAATGTTCA TGTCTTTTTT    54360
TAAAAAAGGT GCTATTGAAA TTCTGTGTCT CCAGCAGGCA AGAATACTTG ACTAACTCTT    54420
TTTGTCTCTT TATGGTATTT TCAGAATAAA GTCTGACTTG TGTTTTTGAG ATTATTGGTG    54480
CCTCATTAAT TCAGCAATAA AGGAAAATAT GCATCTCAAA AATTGGTGAT AAAAAGTTAT    54540
TTCTTGTATA TGTGATAAAG TTTACATGTT GTGTATATAT GTTGTATTGC CAAATACGGC    54600
TATTAAATAC TACGTCATAT TTTAAAGGTT CAGTTTGTAG TGATAGTAAA CAAGCAGTGC    54660
ACTAAGCCTC TTGCGGGCAT CATCTCATCT CACTGTCATC ACAAACCCCA TGCCACAGCG    54720
TAGCTTGACC ACTAAAAGTA ATGCATCTGC AAGCATACTG CCAGGTTTTG GATAGTTTGT    54780
ACCAACAGTT ACCTTATCAA GGTAAATCCC AGACTCTAAA AGAGTTGGTG CTGTGTCACT    54840
ACATGCATAA CTTTAAATAA ATTTCCTGCC GGGCGCGGTG GCTCACGCCT GTAATCCCAG    54900
CAGTTTGGGA GGCCGAGGCA AGTGGATCAC TTGAGGTCAG GAGTTTGAGA CCAGCCTGGC    54960
```

-continued

```
CAACGTGGTG AAACCCTGTC TCTACTAAAA ATACAAAAAT TAGCCAGGCG TGTGGTGGCA    55020

GGCACCTGTA ATCCCAGCTA CTTGGGAGGA TGAGGCAGGA GAATCATTTG AATCCTGCAG    55080

GCGGAGGTTG CAGTGAGCCA AGATGGCGTC ATTGCACTCC AGCCTGGGCG ACAAGAGCGA    55140

GACTCCGTAT TAAAAAAAAA AAAAAAAAAA AAAAAAAATT CCTCTCCTGT TTGAGCTTTC    55200

CCTTACCTGT AAAGAGGGGA GAATATGTAT TTACTTCAAA GAGTTCAGGG AAATGACTCT    55260

CACTAGTTTG AGATTCTAGG TATAAAAATA CATTCTTATA TAATTTTAAC ACCAATGTGA    55320

GAGATTATTA TTCTTGCTAA ACCAATTCAG TTTTATTTGC TGTCTAAAAT GTGTGAATAA    55380

GTAATTGTCC ATTATTTTCT GAAGTGTTTT GGAACTCAAC ACATGATTGT GAGGAGGATT    55440

TGTTGCTAAA CATCTTTCTG GTTATTCAAG CTCGTGTATA CTGTGCTCTG TTGAGACATG    55500

CAGAGTTACT TTCTGTCTGG GTCACAGGTC AGTTCTTGAT AGTTTTCGGA CAATTAACCA    55560

GTTTTCATTT GCCCATGACC ACCTTTATTC TTTTTCCTCA ACTGCACCCA TCTTTTATAA    55620

GGTCTTTCAG TTTATTGCAG AGAAGATGGT GGAGAAAAGC CGGAATTCCC ACCCACCGCT    55680

GCCATCCCCA TGTTTTATCA TTGGCTAGAG TGGAAAATAG CAGTAACTAC TGTGAGAGAT    55740

CATTTGTTTA TATAATGGAA ACAAAGATGA GGAAAGAACC TGGCTTAGAT CAGAGAACTG    55800

ATGTATTTAG ATTCTTTTTT TTTTTTTTTT TAAGACGGAG TGTTGCTCTG TTGCCCAGAC    55860

TGGAGTACAG TGGCTCAATC TCGGCTCACT GCAACCTCCA TTTCCCTGGT TCAAGCAATT    55920

ATCCTGCCTC AGCCTCCCAA GTATTTGGGA TTACAGGCGT GTTCCACCAC ACCTGGCTAA    55980

TTTTTTGTAT TTTTAGTAGA GACGGGGTTT CGCCATGTTG GCCAGGCTGG TCTCGAAATC    56040

CTGACCTCAG ATGATCCACC CGCCTTGGCC TCCCAAAGTG CTGGGATTAC AGGCGCGAGC    56100

CACCGCGCCT GGCCCAATGT ATTTGGATTC TTAAAGAACA CTTTCAAATT AAATATCAGT    56160

TGAAGAGAAC TAGAACTAAA GAATTTCTGT GTCAAACTGT TTAGCAAATG TAAGTAGAAG    56220

CTGGGAGATG TGTCCTGGAA TGAATGAATA CATCAGTAAA ATACCATACG TATGTTATGA    56280

TGTTATTGTT TCCTTGCCTT GGTTGATTTG GTTTTACTGT GAAATAATTT TCAATATAGA    56340

ATTGTGATCG TTGGAATTTG GTCATCTACT AGAAAATGAA AAAGAAGTTA ATAGCTATCT    56400

TCCTTAAAGA TTTCTGAGGT TGGGATTAAG GTAGTGTTCC CAAGGTGTTC TAAAACGGCA    56460

GCGAGAGCTG TGCACTCACT TCACAAATTT GAATTCCTGC TCTGTGTTAG GCGCTG        56516
```

(2) INFORMATION FOR SEQ ID NO: 2:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: pg15RACE130n
        (B) LOCATION: complement 132..154
        (D) OTHER INFORMATION: Location relative to seqID2 and seqID3

(xi) SEQUENCE DESCRIPTION: SEQ ID NO: 2:

```
GGTCGTCCAG CGCTTGGTAG AAG                                              23
```

(2) INFORMATION FOR SEQ ID NO: 3:

(i) SEQUENCE CHARACTERISTICS:
        (A) LENGTH: 5227 base pairs

```
        (B) TYPE: NUCLEIC ACID
        (C) STRANDEDNESS: SINGLE
        (D) TOPOLOGY: LINEAR (ii) MOLECULE TYPE: CDNA (vi) ORIGINAL SOURCE:
        (A) ORGANISM: Homo sapiens (ix) FEATURE:
        (A) NAME/KEY: CDS
        (B) LOCATION: 31..1089

(ix) FEATURE:
        (A) NAME/KEY: polyAdenylation signal
        (B) LOCATION: 5180..5186

(xi) SEQUENCE DESCRIPTION: SEQ ID NO: 3:

CTGCTGTCCC TGGTGCTCCA CACGTACTCC ATG CGC TAC CTG CTG CCC AGC GTC         54
                                 Met Arg Tyr Leu Leu Pro Ser Val
                                  1               5

GTG CTC CTG GGC ACG GCG CCC ACC TAC GTG TTG GCC TGG GGG GTC TGG         102
Val Leu Leu Gly Thr Ala Pro Thr Tyr Val Leu Ala Trp Gly Val Trp
         10              15                  20

CGG CTG CTC TCC GCC TTC CTG CCC GCC CGC TTC TAC CAA GCG CTG GAC         150
Arg Leu Leu Ser Ala Phe Leu Pro Ala Arg Phe Tyr Gln Ala Leu Asp
 25              30                  35                  40

GAC CGG CTC TAC TGC GTC TAC CAG AGC ATG GTG CTC TTC TTC TTC GAG         198
Asp Arg Leu Tyr Cys Val Tyr Gln Ser Met Val Leu Phe Phe Phe Glu
                 45                  50                  55

AAT TAC ACC GGG GTC CAG ATA TTG CTA TAT GGA GAT TTG CCA AAA AAT         246
Asn Tyr Thr Gly Val Gln Ile Leu Leu Tyr Gly Asp Leu Pro Lys Asn
             60                  65                  70

AAA GAA AAT ATA ATA TAT TTA GCA AAT CAT CAA AGC ACA GTT GAC TGG         294
Lys Glu Asn Ile Ile Tyr Leu Ala Asn His Gln Ser Thr Val Asp Trp
         75                  80                  85

ATT GTT GCT GAC ATC TTG GCC ATC AGG CAG AAT GCG CTA GGA CAT GTG         342
Ile Val Ala Asp Ile Leu Ala Ile Arg Gln Asn Ala Leu Gly His Val
 90                  95                 100

CGC TAC GTG CTG AAA GAA GGG TTA AAA TGG CTG CCA TTG TAT GGG TGT         390
Arg Tyr Val Leu Lys Glu Gly Leu Lys Trp Leu Pro Leu Tyr Gly Cys
105                 110                 115                 120

TAC TTT GCT CAG CAT GGA GGA ATC TAT GTA AAG CGC AGT GCC AAA TTT         438
Tyr Phe Ala Gln His Gly Gly Ile Tyr Val Lys Arg Ser Ala Lys Phe
                125                 130                 135

AAC GAG AAA GAG ATG CGA AAC AAG TTG CAG AGC TAC GTG GAC GCA GGA         486
Asn Glu Lys Glu Met Arg Asn Lys Leu Gln Ser Tyr Val Asp Ala Gly
            140                 145                 150

ACT CCA ATG TAT CTT GTG ATT TTT CCA GAA GGT ACA AGG TAT AAT CCA         534
Thr Pro Met Tyr Leu Val Ile Phe Pro Glu Gly Thr Arg Tyr Asn Pro
        155                 160                 165

GAG CAA ACA AAA GTC CTT TCA GCT AGT CAG GCA TTT GCT GCC CAA CGT         582
Glu Gln Thr Lys Val Leu Ser Ala Ser Gln Ala Phe Ala Ala Gln Arg
    170                 175                 180

GGC CTT GCA GTA TTA AAA CAT GTG CTA ACA CCA CGA ATA AAG GCA ACT         630
Gly Leu Ala Val Leu Lys His Val Leu Thr Pro Arg Ile Lys Ala Thr
185                 190                 195                 200

CAC GTT GCT TTT GAT TGC ATG AAG AAT TAT TTA GAT GCA ATT TAT GAT         678
His Val Ala Phe Asp Cys Met Lys Asn Tyr Leu Asp Ala Ile Tyr Asp
                205                 210                 215

GTT ACG GTG GTT TAT GAA GGG AAA GAC GAT GGA GGG CAG CGA AGA GAG         726
Val Thr Val Val Tyr Glu Gly Lys Asp Asp Gly Gly Gln Arg Arg Glu
            220                 225                 230
```

| | | |
|---|---|---|
| TCA CCG ACC ATG ACG GAA TTT CTC TGC AAA GAA TGT CCA AAA ATT CAT<br>Ser Pro Thr Met Thr Glu Phe Leu Cys Lys Glu Cys Pro Lys Ile His<br>              235                      240                    245 | 774 |
| ATT CAC ATT GAT CGT ATC GAC AAA AAA GAT GTC CCA GAA GAA CAA GAA<br>Ile His Ile Asp Arg Ile Asp Lys Lys Asp Val Pro Glu Glu Gln Glu<br>250                          255                      260 | 822 |
| CAT ATG AGA AGA TGG CTG CAT GAA CGT TTC GAA ATC AAA GAT AAG ATG<br>His Met Arg Arg Trp Leu His Glu Arg Phe Glu Ile Lys Asp Lys Met<br>265                          270                      275                      280 | 870 |
| CTT ATA GAA TTT TAT GAG TCA CCA GAT CCA GAA AGA AGA AAA AGA TTT<br>Leu Ile Glu Phe Tyr Glu Ser Pro Asp Pro Glu Arg Arg Lys Arg Phe<br>              285                      290                            295 | 918 |
| CCT GGG AAA AGT GTT AAT TCC AAA TTA AGT ATC AAG AAG ACT TTA CCA<br>Pro Gly Lys Ser Val Asn Ser Lys Leu Ser Ile Lys Lys Thr Leu Pro<br>              300                      305                      310 | 966 |
| TCA ATG TTG ATC TTA AGT GGT TTG ACT GCA GGC ATG CTT ATG ACC GAT<br>Ser Met Leu Ile Leu Ser Gly Leu Thr Ala Gly Met Leu Met Thr Asp<br>315                          320                      325 | 1014 |
| GCT GGA AGG AAG CTG TAT GTG AAC ACC TGG ATA TAT GGA ACC CTA CTT<br>Ala Gly Arg Lys Leu Tyr Val Asn Thr Trp Ile Tyr Gly Thr Leu Leu<br>330                          335                      340 | 1062 |
| GGC TGC CTG TGG GTT ACT ATT AAA GCA TAGACAAGTA GCTGTCTCCA<br>Gly Cys Leu Trp Val Thr Ile Lys Ala<br>345                          350 | 1109 |
| GACAGTGGGA TGTGCTACAT TGTCTATTTT TGGCGGCTGC ACATGACATC AAATTGTTTC | 1169 |
| CTGAATTTAT TAAGGAGTGT AAATAAAGCC TTGTTGATTG AAGATTGGAT AATAGAATTT | 1229 |
| GTGACGAAAG CTGATATGCA ATGGTCTTGG GCAAACATAC CTGGTTGTAC AACTTTAGCA | 1289 |
| TCGGGCTGC TGGAAGGGTA AAAGCTAAAT GGAGTTTCTC CTGCTCTGTC CATTTCCTAT | 1349 |
| GAACTAATGA CAACTTGAGA AGGCTGGGAG GATTGTGTAT TTTGCAAGTC AGATGGCTGC | 1409 |
| ATTTTTGAGC ATTAATTTGC AGCGTATTTC ACTTTTTCTG TTATTTTCAA TTTATTACAA | 1469 |
| CTTGACAGCT CCAAGCTCTT ATTACTAAAG TATTTAGTAT CTTGCAGCTA GTTAATATTT | 1529 |
| CATCTTTTGC TTATTTCTAC AAGTCAGTGA ATAAATTGT ATTTAGGAAG TGTCAGGATG | 1589 |
| TTCAAAGGAA AGGGTAAAAA GTGTTCATGG GGAAAAAGCT CTGTTTAGCA CATGATTTTA | 1649 |
| TTGTATTGCG TTATTAGCTG ATTTACTCA TTTTATATTT GCAAAATAAA TTTCTAATAT | 1709 |
| TTATTGAAAT TGCTTAATTT GCACACCCTG TACACACAGA AAATGGTATA AAATATGAGA | 1769 |
| ACGAAGTTTA AAATTGTGAC TCTGATTCAT TATAGCAGAA CTTTAAATTT CCCAGCTTTT | 1829 |
| TGAAGATTTA AGCTACGCTA TTAGTACTTC CCTTTGTCTG TGCCATAAGT GCTTGAAAAC | 1889 |
| GTTAAGGTTT TCTGTTTTGT TTTGTTTTTT TAATATCAAA AGAGTCGGTG TGAACCTTGG | 1949 |
| TTGGACCCCA AGTTCACAAG ATTTTTAAGG TGATGAGAGC CTGCAGACAT TCTGCCTAGA | 2009 |
| TTTACTAGCG TGTGCCTTTT GCCTGCTTCT CTTTGATTTC ACAGAATATT CATTCAGAAG | 2069 |
| TCGCGTTTCT GTAGTGTGGT GGATTCCCAC TGGGCTCTGG TCCTTCCCTT GGATCCCGTC | 2129 |
| AGTGGTGCTG CTCAGCGGCT TGCACGTAGA CTTGCTAGGA AGAAATGCAG AGCCAGCCTG | 2189 |
| TGCTGCCCAC TTTCAGAGTT GAACTCTTTA AAGCCCTTGT GAGTGGGCTT CACCAGCTAC | 2249 |
| TGCAGAGGCA TTTTGCATTT GTCTGTGTCA AGAAGTTCAC CTTCTCAAGC CAGTGAAATA | 2309 |
| CAGACTTAAT TCGTCATGAC TGAACGAATT TGTTTATTTC CCATTAGGTT TAGTGGAGCT | 2369 |
| ACACATTAAT ATGTATCGCC TTAGAGCAAG AGCTGTGTTC CAGGAACCAG ATCACGATTT | 2429 |
| TTAGCCATGG AACAATATAT CCCATGGGAG AAGACCTTTC AGTGTGAACT GTTCTATTTT | 2489 |
| TGTGTTATAA TTTAAACTTC GATTTCCTCA TAGTCCTTTA AGTTGACATT CTGCTTACT | 2549 |

```
GCTACTGGAT TTTTGCTGCA GAAATATATC AGTGGCCCAC ATTAAACATA CCAGTTGGAT    2609

CATGATAAGC AAAATGAAAG AAATAATGAT TAAGGGAAAA TTAAGTGACT GTGTTACACT    2669

GCTTCTCCCA TGCCAGAGAA TAAACTCTTT CAAGCATCAT CTTTGAAGAG TCGTGTGGTG    2729

TGAATTGGTT TGTGTACATT AGAATGTATG CACACATCCA TGGACACTCA GGATATAGTT    2789

GGCCTAATAA TCGGGGCATG GGTAAAACTT ATGAAAATTT CCTCATGCTG AATTGTAATT    2849

TTCTCTTACC TGTAAAGTAA AATTTAGATC AATTCCATGT CTTTGTTAAG TACAGGGATT    2909

TAATATATTT TGAATATAAT GGGTATGTTC TAAATTTGAA CTTTGAGAGG CAATACTGTT    2969

GGAATTATGT GGATTCTAAC TCATTTTAAC AAGGTAGCCT GACCTGCATA AGATCACTTG    3029

AATGTTAGGT TTCATAGAAC TATACTAATC TTCTCACAAA AGGTCTATAA AATACAGTCG    3089

TTGAAAAAAA TTTTGTATCA AAATGTTTGG AAAATTAGAA GCTTCTCCTT AACCTGTATT    3149

GATACTGACT TGAATTATTT TCTAAAATTA AGAGCCGTAT ACCTACCTGT AAGTCTTTTC    3209

ACATATCATT TAAACTTTTG TTTGTATTAT TACTGATTTA CAGCTTAGTT ATTAATTTTT    3269

CTTTATAAGA ATGCCGTCGA TGTGCATGCT TTTATGTTTT TCAGAAAAGG GTGTGTTTGG    3329

ATGAAAGTAA AAAAAAAAAT AAAATCTTTC ACTGTCTCTA ATGGCTGTGC TGTTTAACAT    3389

TTTTTGACCC TAAAATTCAC CAACAGTCTC CCAGTACATA AAATAGGCTT AATGACTGGC    3449

CCTGCATTCT TCACAATATT TTTCCCTAAG CTTTGAGCAA AGTTTTAAAA AAATACACTA    3509

AAATAATCAA AACTGTTAAG CAGTATATTA GTTTGGTTAT ATAAATTCAT CTGCAATTTA    3569

TAAGATGCAT GGCCGATGTT AATTTGCTTG GCAATTCTGT AATCATTAAG TGATCTCAGT    3629

GAAACATGTC AAATGCCTTA AATTAACTAA GTTGGTGAAT AAAAGTGCCG ATCTGGCTAA    3689

CTCTTACACC ATACATACTG ATAGTTTTTC ATATGTTTCA TTTCCATGTG ATTTTTAAAA    3749

TTTAGAGTGG CAACAATTTT GCTTAATATG GGTTACATAA GCTTTATTTT TTCCTTTGTT    3809

CATAATTATA TTCTTTGAAT AGGTCTGTGT CAATCAAGTG ATCTAACTAG ACTGATCATA    3869

GATAGAAGGA AATAAGGCCA AGTTCAAGAC CAGCCTGGGC AACATATCGA GAACCTGTCT    3929

ACAAAAAAAT TAAAAAAAAT TAGCCAGGCA TGGTGGCGTA CACTGAGTAG TTTGTCCCAG    3989

CTACTCGGGA GGGTGAGGTG GGAGGATCGC TTCAGCCCAG GAGGTTGAGA TTGCAGTGAG    4049

CCATGGACAT ACCACTGCAC TACAGCCTAG GTAACAGCAC GAGACCCCAA CTCTTAGAAA    4109

ATGAAAAGGA AATATAGAAA TATAAAATTT GCTTATTATA GACACACAGT AACTCCCAGA    4169

TATGTACCAC AAAAAATGTG AAAAGAGAGA GAAATGTCTA CCAAAGCAGT ATTTTGTGTG    4229

TATAATTGCA AGCGCATAGT AAAATAATTT TAACCTTAAT TTGTTTTTAG TAGTGTTTAG    4289

ATTGAAGATT GAGTGAAATA TTTTCTTGGC AGATATTCCG TATCTGGTGG AAAGCTACAA    4349

TGCAATGTCG TTGTAGTTTT GCATGGCTTG CTTTATAAAC AAGATTTTTT CTCCCTCCTT    4409

TTGGGCCAGT TTTCATTACG AGTAACTCAC ACTTTTTGAT TAAAGAACTT GAAATTACGT    4469

TATCACTTAG TATAATTGAC ATTATATAGA GACTATGTAA CATGCAATCA TTAGAATCAA    4529

AATTAGTACT TTGGTCAAAA TATTTACAAC ATTCACATAC TTGTCAAATA TTCATGTAAT    4589

TAACTGAATT TAAAACCTTC AACTATTATG AAGTGCTCGT CTGTACAATC GCTAATTTAC    4649

TCAGTTTAGA GTAGCTACAA CTCTTCGATA CTATCATCAA TATTTGACAT CTTTTCCAAT    4709

TTGTGTATGA AAAGTAAATC TATTCCTGTA GCAACTGGGG AGTCATATAT GAGGTCAAAG    4769

ACATATACCT TGTTATTATA ATATGTATAC TATAATAATA GCTGGTTATC CTGAGCAGGG    4829

GAAAAGGTTA TTTTTAGGAA AACCACTTCA AATGAAAGC TGAAGTACTT CTAATATACT    4889

GAGGGAAGTA TAATATGTGG AACAAACTCT CAACAAAATG TTTATTGATG TTGATGAAAC    4949
```

```
AGATCAGTTT TTCCATCCGG ATTATTATTG GTTCATGATT TTATATGTGA ATATGTAAGA    5009

TATGTTCTGC AATTTTATAA ATGTTCATGT CTTTTTTTAA AAAAGGTGCT ATCGAAATTC    5069

TGTGTCTCCA GCAGGCAAGA ATACTTGACT AACTCTTTTT GTCTCTTTAT GGTATTTTCA    5129

GAATAAAGTC TGACTTGTGT TTTTGAGATT ATTGGTGCCT CATTAATTCA GCAATAAAGG    5189

AAAATATGCA TTTCAAAAAN AAAAAAAAAA AAAAAAA                             5227
```

(2) INFORMATION FOR SEQ ID NO: 4:

(i) SEQUENCE CHARACTERISTICS:
        (A) LENGTH: 353 amino acids
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: potential Transmembrane helix
        (B) LOCATION: 1..33
        (C) IDENTIFICATION METHOD: Rao and Argos method (ix) FEATURE:
        (A) NAME/KEY: potential Transmembrane helix
        (B) LOCATION: 4..20
        (C) IDENTIFICATION METHOD: Klein, Kanehisa and DeLisi method (ix) FEATURE:
        (A) NAME/KEY: potential Transmembrane helix
        (B) LOCATION: 4..24
        (C) IDENTIFICATION METHOD: Eisenberg,Schwarz,Komarony
           and Wall method (ix) FEATURE:
        (A) NAME/KEY: potential N-myristoylation site
        (B) LOCATION: 12
        (C) IDENTIFICATION METHOD: prosite match (ix) FEATURE:
        (A) NAME/KEY: potential Transmembrane helix
        (B) LOCATION: 50..70
        (C) IDENTIFICATION METHOD: Eisenberg,Schwarz,Komarony and Wall
           method (ix) FEATURE:
        (A) NAME/KEY: potential N-glycosylation site
        (B) LOCATION: 57
        (C) IDENTIFICATION METHOD: prosite match (ix) FEATURE:
        (A) NAME/KEY: potential Transmembrane helix
        (B) LOCATION: 76..96
        (C) IDENTIFICATION METHOD: Eisenberg,Schwarz,Komarony and Wall
           method (ix) FEATURE:
        (A) NAME/KEY: potential Tyrosine kinase phosphorylation site
        (B) LOCATION: 78
        (C) IDENTIFICATION METHOD: prosite match (ix) FEATURE:
        (A) NAME/KEY: potential Casein kinase II phosphorylation site
        (B) LOCATION: 84
        (C) IDENTIFICATION METHOD: prosite match (ix) FEATURE:
        (A) NAME/KEY: potential Leucine zipper pattern
        (B) LOCATION: 94..115
        (C) IDENTIFICATION METHOD: prosite match (ix) FEATURE:
        (A) NAME/KEY: potential N-myristoylation site
        (B) LOCATION: 119

-continued

```
        (C) IDENTIFICATION METHOD: prosite match (ix) FEATURE:
        (A) NAME/KEY: potential Protein kinase C phosphorylation site
        (B) LOCATION: 133
        (C) IDENTIFICATION METHOD: prosite match (ix) FEATURE:
        (A) NAME/KEY: potential Casein kinase II phosphorylation site
        (B) LOCATION: 147
        (C) IDENTIFICATION METHOD: prosite match (ix) FEATURE:
        (A) NAME/KEY: potential Protein kinase C phosphorylation site
        (B) LOCATION: 194
        (C) IDENTIFICATION METHOD: prosite match (ix) FEATURE:
        (A) NAME/KEY: potential Tyrosine kinase phosphorylation site
        (B) LOCATION: 215
        (C) IDENTIFICATION METHOD: prosite match (ix) FEATURE:
        (A) NAME/KEY: potential Tyrosine sulfatation site
        (B) LOCATION: 221
        (C) IDENTIFICATION METHOD: prosite match (ix) FEATURE:
        (A) NAME/KEY: potential cAMP- and cGMP-dependent protein
            kinase phophorylation  site
        (B) LOCATION: 233
        (C) IDENTIFICATION METHOD: prosite match (ix) FEATURE:
        (A) NAME/KEY: potential Casein kinase II phosphorylation site
        (B) LOCATION: 235
        (C) IDENTIFICATION METHOD: prosite match (ix) FEATURE:
        (A) NAME/KEY: potential Protein kinase C phosphorylation site
        (B) LOCATION: 306
        (C) IDENTIFICATION METHOD: prosite match (ix) FEATURE:
        (A) NAME/KEY: potential Transmembrane helix
        (B) LOCATION: 310..330
        (C) IDENTIFICATION METHOD: Eisenberg,Schwarz,Komarony and Wall
            method (ix) FEATURE:
        (A) NAME/KEY: potential N-myristoylation site
        (B) LOCATION: 319
        (C) IDENTIFICATION METHOD: prosite match (ix) FEATURE:
        (A) NAME/KEY: potential N-myristoylation site
        (B) LOCATION: 323
        (C) IDENTIFICATION METHOD: prosite match (ix) FEATURE:
        (A) NAME/KEY: potential Amidation site
        (B) LOCATION: 329
        (C) IDENTIFICATION METHOD: prosite match (ix) FEATURE:
        (A) NAME/KEY: potential Transmembrane helix
        (B) LOCATION: 333..353
        (C) IDENTIFICATION METHOD: Eisenberg,Schwarz,Komarony and Wall
            method (ix) FEATURE:
        (A) NAME/KEY: potential N-myristoylation site
        (B) LOCATION: 341
        (C) IDENTIFICATION METHOD: prosite match (ix) FEATURE:
        (A) NAME/KEY: potential Protein kinase C phosphorylation site
        (B) LOCATION: 350
        (C) IDENTIFICATION METHOD: prosite match
```

(xi) SEQUENCE DESCRIPTION: SEQ ID NO: 4:

```
Met Arg Tyr Leu Leu Pro Ser Val Val Leu Gly Thr Ala Pro Thr
 1               5                  10                  15

Tyr Val Leu Ala Trp Gly Val Trp Arg Leu Leu Ser Ala Phe Leu Pro
                20                  25                  30

Ala Arg Phe Tyr Gln Ala Leu Asp Asp Arg Leu Tyr Cys Val Tyr Gln
                35                  40                  45

Ser Met Val Leu Phe Phe Phe Glu Asn Tyr Thr Gly Val Gln Ile Leu
        50                  55                  60

Leu Tyr Gly Asp Leu Pro Lys Asn Lys Glu Asn Ile Ile Tyr Leu Ala
65                  70                  75                  80

Asn His Gln Ser Thr Val Asp Trp Ile Val Asp Ile Leu Ala Ile
                85                  90                  95

Arg Gln Asn Ala Leu Gly His Val Arg Tyr Val Leu Lys Glu Gly Leu
                100                 105                 110

Lys Trp Leu Pro Leu Tyr Gly Cys Tyr Phe Ala Gln His Gly Gly Ile
                115                 120                 125

Tyr Val Lys Arg Ser Ala Lys Phe Asn Glu Lys Glu Met Arg Asn Lys
                130                 135                 140

Leu Gln Ser Tyr Val Asp Ala Gly Thr Pro Met Tyr Leu Val Ile Phe
145                 150                 155                 160

Pro Glu Gly Thr Arg Tyr Asn Pro Glu Gln Thr Lys Val Leu Ser Ala
                165                 170                 175

Ser Gln Ala Phe Ala Ala Gln Arg Gly Leu Ala Val Leu Lys His Val
                180                 185                 190

Leu Thr Pro Arg Ile Lys Ala Thr His Val Ala Phe Asp Cys Met Lys
                195                 200                 205

Asn Tyr Leu Asp Ala Ile Tyr Asp Val Thr Val Val Tyr Glu Gly Lys
                210                 215                 220

Asp Asp Gly Gly Gln Arg Arg Glu Ser Pro Thr Met Thr Glu Phe Leu
225                 230                 235                 240

Cys Lys Glu Cys Pro Lys Ile His Ile His Ile Asp Arg Ile Asp Lys
                245                 250                 255

Lys Asp Val Pro Glu Glu Gln Glu His Met Arg Arg Trp Leu His Glu
                260                 265                 270

Arg Phe Glu Ile Lys Asp Lys Met Leu Ile Glu Phe Tyr Glu Ser Pro
                275                 280                 285

Asp Pro Glu Arg Arg Lys Arg Phe Pro Gly Lys Ser Val Asn Ser Lys
                290                 295                 300

Leu Ser Ile Lys Lys Thr Leu Pro Ser Met Leu Ile Leu Ser Gly Leu
305                 310                 315                 320

Thr Ala Gly Met Leu Met Thr Asp Ala Gly Arg Lys Leu Tyr Val Asn
                325                 330                 335

Thr Trp Ile Tyr Gly Thr Leu Leu Gly Cys Leu Trp Val Thr Ile Lys
                340                 345                 350

Ala
```

(2) INFORMATION FOR SEQ ID NO: 5:

(i) SEQUENCE CHARACTERISTICS:
       (A) LENGTH: 364 amino acids
       (B) TYPE: AMINO ACID
       (C) STRANDEDNESS: SINGLE
       (D) TOPOLOGY: LINEAR (ii) MOLECULE TYPE: PROTEIN (vi) ORIGINAL SOURCE:
    (A) ORGANISM: Homo sapiens (ix) FEATURE:
    (A) NAME/KEY: potential protein
    (B) LOCATION: 1..364

(xi) SEQUENCE DESCRIPTION: SEQ ID NO: 5:

```
Met Leu Leu Ser Leu Val Leu His Thr Tyr Ser Met Arg Tyr Leu Leu
1               5                   10                  15

Pro Ser Val Val Leu Leu Gly Thr Ala Pro Thr Tyr Val Leu Ala Trp
            20                  25                  30

Gly Val Trp Arg Leu Leu Ser Ala Phe Leu Pro Ala Arg Phe Tyr Gln
            35                  40                  45

Ala Leu Asp Asp Arg Leu Tyr Cys Val Tyr Gln Ser Met Val Leu Phe
        50                  55                  60

Phe Phe Glu Asn Tyr Thr Gly Val Gln Ile Leu Leu Tyr Gly Asp Leu
65                  70                  75                  80

Pro Lys Asn Lys Glu Asn Ile Ile Tyr Leu Ala Asn His Gln Ser Thr
                85                  90                  95

Val Asp Trp Ile Val Ala Asp Ile Leu Ala Ile Arg Gln Asn Ala Leu
            100                 105                 110

Gly His Val Arg Tyr Val Leu Lys Glu Gly Leu Lys Trp Leu Pro Leu
            115                 120                 125

Tyr Gly Cys Tyr Phe Ala Gln His Gly Gly Ile Tyr Val Lys Arg Ser
        130                 135                 140

Ala Lys Phe Asn Glu Lys Glu Met Arg Asn Lys Leu Gln Ser Tyr Val
145                 150                 155                 160

Asp Ala Gly Thr Pro Met Tyr Leu Val Ile Phe Pro Glu Gly Thr Arg
                165                 170                 175

Tyr Asn Pro Glu Gln Thr Lys Val Leu Ser Ala Ser Gln Ala Phe Ala
            180                 185                 190

Ala Gln Arg Gly Leu Ala Val Leu Lys His Val Leu Thr Pro Arg Ile
            195                 200                 205

Lys Ala Thr His Val Ala Phe Asp Cys Met Lys Asn Tyr Leu Asp Ala
210                 215                 220

Ile Tyr Asp Val Thr Val Tyr Glu Gly Lys Asp Asp Gly Gly Gln
225                 230                 235                 240

Arg Arg Glu Ser Pro Thr Met Thr Glu Phe Leu Cys Lys Glu Cys Pro
                245                 250                 255

Lys Ile His Ile His Ile Asp Arg Ile Asp Lys Lys Asp Val Pro Glu
            260                 265                 270

Glu Gln Glu His Met Arg Arg Trp Leu His Glu Arg Phe Glu Ile Lys
            275                 280                 285

Asp Lys Met Leu Ile Glu Phe Tyr Glu Ser Pro Asp Pro Glu Arg Arg
            290                 295                 300

Lys Arg Phe Pro Gly Lys Ser Val Asn Ser Lys Leu Ser Ile Lys Lys
305                 310                 315                 320

Thr Leu Pro Ser Met Leu Ile Leu Ser Gly Leu Thr Ala Gly Met Leu
                325                 330                 335

Met Thr Asp Ala Gly Arg Lys Leu Tyr Val Asn Thr Trp Ile Tyr Gly
            340                 345                 350

Thr Leu Leu Gly Cys Leu Trp Val Thr Ile Lys Ala
            355                 360
```

```
(2) INFORMATION FOR SEQ ID NO: 6:

(i) SEQUENCE CHARACTERISTICS:
        (A) LENGTH: 26 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: GC1.5p.1
        (B) LOCATION: 4..29
        (D) OTHER INFORMATION: Location relative to seqID2 and seqID3

(xi) SEQUENCE DESCRIPTION: SEQ ID NO: 6:

CTGTCCCTGG TGCTCCACAC GTACTC                                              26

(2) INFORMATION FOR SEQ ID NO: 7:

(i) SEQUENCE CHARACTERISTICS:
        (A) LENGTH: 26 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: GC1.5p.2
        (B) LOCATION: 11..36
        (D) OTHER INFORMATION: Location relative to seqID2 and seqID3

(xi) SEQUENCE DESCRIPTION: SEQ ID NO: 7:

TGGTGCTCCA CACGTACTCC ATGCGC                                              26

(2) INFORMATION FOR SEQ ID NO: 8:

(i) SEQUENCE CHARACTERISTICS:
        (A) LENGTH: 27 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: pg15RACE196
        (B) LOCATION: complement 196..222
        (D) OTHER INFORMATION: Location relative to seqID2 and seqID3

(xi) SEQUENCE DESCRIPTION: SEQ ID NO: 8:

CAATATCTGG ACCCCGGTGT AATTCTC                                             27

(2) INFORMATION FOR SEQ ID NO: 9:

(i) SEQUENCE CHARACTERISTICS:
        (A) LENGTH: 34 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
```

```
            (A) ORGANISM: Homo sapiens (ix) FEATURE:
            (A) NAME/KEY: GC1.3P
            (B) LOCATION: complement 5054..5087
            (D) OTHER INFORMATION: Location relative to seqID3

(xi) SEQUENCE DESCRIPTION: SEQ ID NO: 9:

CTTGCCTGCT GGAGACACAG AATTTCGATA GCAC                                   34

(2) INFORMATION FOR SEQ ID NO: 10:

(i) SEQUENCE CHARACTERISTICS:
            (A) LENGTH: 24 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: PGRT32
            (B) LOCATION: complement 5198..5221
            (D) OTHER INFORMATION: Location relative to seqID3

(xi) SEQUENCE DESCRIPTION: SEQ ID NO: 10:

TTTTTTTTTT TTTTTTTTTG AAAT                                              24

(2) INFORMATION FOR SEQ ID NO: 11:

(i) SEQUENCE CHARACTERISTICS:
            (A) LENGTH: 6 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:
            (A) ORGANISM: Homo sapiens (ix) FEATURE:
            (A) NAME/KEY: box2
            (B) LOCATION: 160..165
            (D) OTHER INFORMATION: extracted from seq ID4,pattern present
                in AF003136, P33333, P26647, (xi) SEQUENCE DESCRIPTION: SEQ ID NO: 11:

Phe Pro Glu Gly Thr Arg
1               5

(2) INFORMATION FOR SEQ ID NO: 12:

(i) SEQUENCE CHARACTERISTICS:
            (A) LENGTH: 6 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:
            (A) ORGANISM: Homo sapiens (ix) FEATURE:
            (A) NAME/KEY: box2
            (B) LOCATION: 129..134
            (D) OTHER INFORMATION: extracted from seq Z72511

(xi) SEQUENCE DESCRIPTION: SEQ ID NO: 12:
```

```
Phe Pro Glu Gly Thr Asp
1               5

(2) INFORMATION FOR SEQ ID NO: 13:

(i) SEQUENCE CHARACTERISTICS:
        (A) LENGTH: 6 amino acids
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: box2
        (B) LOCATION: 223..228
        (D) OTHER INFORMATION: extracted from seq P38226 and Z49770

(xi) SEQUENCE DESCRIPTION: SEQ ID NO: 13:

Phe Pro Glu Gly Thr Asn
1               5

(2) INFORMATION FOR SEQ ID NO: 14:

(i) SEQUENCE CHARACTERISTICS:
        (A) LENGTH: 6 amino acids
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: box2
        (B) LOCATION: 90..95
        (D) OTHER INFORMATION: extracted from seq Z49860 and Z29518

(xi) SEQUENCE DESCRIPTION: SEQ ID NO: 14:

Phe Val Glu Gly Thr Arg
1               5

(2) INFORMATION FOR SEQ ID NO: 15:

(i) SEQUENCE CHARACTERISTICS:
        (A) LENGTH: 9 amino acids
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: box3
        (B) LOCATION: 211..219
        (D) OTHER INFORMATION: extracted from seq ID 4,pattern present
            in AF003136

(xi) SEQUENCE DESCRIPTION: SEQ ID NO: 15:

Leu Asp Ala Ile Tyr Asp Val Thr Val
1               5

(2) INFORMATION FOR SEQ ID NO: 16:

(i) SEQUENCE CHARACTERISTICS:
```

(A) LENGTH: 9 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:
            (A) ORGANISM: Homo sapiens (ix) FEATURE:
            (A) NAME/KEY: box3
            (B) LOCATION: 204..212
            (D) OTHER INFORMATION: extracted from seq Z72511

(xi) SEQUENCE DESCRIPTION: SEQ ID NO: 16:

Val Glu Tyr Ile Tyr Asp Ile Thr Ile
1               5

(2) INFORMATION FOR SEQ ID NO: 17:

(i) SEQUENCE CHARACTERISTICS:
            (A) LENGTH: 9 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:
            (A) ORGANISM: Homo sapiens (ix) FEATURE:
            (A) NAME/KEY: box3
            (B) LOCATION: 271..279
            (D) OTHER INFORMATION: extracted from seq P38226

(xi) SEQUENCE DESCRIPTION: SEQ ID NO: 17:

Ile Glu Ser Leu Tyr Asp Ile Thr Ile
1               5

(2) INFORMATION FOR SEQ ID NO: 18:

(i) SEQUENCE CHARACTERISTICS:
            (A) LENGTH: 9 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:
            (A) ORGANISM: Homo sapiens (ix) FEATURE:
            (A) NAME/KEY: box3
            (B) LOCATION: 265..273
            (D) OTHER INFORMATION: extracted from seq Z49770

(xi) SEQUENCE DESCRIPTION: SEQ ID NO: 18:

Leu Asp Ala Ile Tyr Asp Val Thr Ile
1               5

(2) INFORMATION FOR SEQ ID NO: 19:

(i) SEQUENCE CHARACTERISTICS:
            (A) LENGTH: 9 amino acids
            (B) TYPE: AMINO ACID
            (C) STRANDEDNESS: SINGLE
            (D) TOPOLOGY: LINEAR (ii) MOLECULE TYPE: PROTEIN (vi) ORIGINAL SOURCE:

(A) ORGANISM: Homo sapiens (ix) FEATURE:
    (A) NAME/KEY: box3
    (B) LOCATION: 138..146
    (D) OTHER INFORMATION: extracted from seq Z49860

(xi) SEQUENCE DESCRIPTION: SEQ ID NO: 19:

```
Val Pro Ala Ile Tyr Asp Met Thr Val
1               5
```

(2) INFORMATION FOR SEQ ID NO: 20:

(i) SEQUENCE CHARACTERISTICS:
        (A) LENGTH: 9 amino acids
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: box3
        (B) LOCATION: 218..226
        (D) OTHER INFORMATION: extracted from seq Z29518

(xi) SEQUENCE DESCRIPTION: SEQ ID NO: 20:

```
Val Pro Ala Ile Tyr Asp Thr Thr Val
1               5
```

(2) INFORMATION FOR SEQ ID NO: 21:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-123
        (B) LOCATION: 1..47

(ix) FEATURE:
        (A) NAME/KEY: polymorphic base
        (B) LOCATION: 24
        (D) OTHER INFORMATION: base C (ix) FEATURE:
        (A) NAME/KEY: microsequencing oligos 99-123-mis1
        (B) LOCATION: 1..23

(ix) FEATURE:
        (A) NAME/KEY: microsequencing oligos 99-123-mis2
        (B) LOCATION: 25..47

(xi) SEQUENCE DESCRIPTION: SEQ ID NO: 21:

TTTCTCATCC TCACACCTCA CTGCGCCCCT CCTGAACCCA CTCCTTT    47

(2) INFORMATION FOR SEQ ID NO: 22:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR

```
        (ii) MOLECULE TYPE: DNA (vi) ORIGINAL SOURCE:
             (A) ORGANISM: Homo sapiens (ix) FEATURE:
             (A) NAME/KEY: polymorphic fragment 4-26
             (B) LOCATION: 1..47

(ix) FEATURE:
             (A) NAME/KEY: polymorphic base
             (B) LOCATION: 24
             (D) OTHER INFORMATION: base G (ix) FEATURE:
             (A) NAME/KEY: microsequencing oligos 4-26-mis1
             (B) LOCATION: 1..23

(ix) FEATURE:
             (A) NAME/KEY: microsequencing oligos 4-26-mis2
             (B) LOCATION: 25..47

(xi) SEQUENCE DESCRIPTION: SEQ ID NO: 22:

CCCTGTNAGA CACGTCCTGT ATCGTTGTTG AGATGGGAAA GTGCATC                          47

(2) INFORMATION FOR SEQ ID NO: 23:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: polymorphic fragment 4-14
             (B) LOCATION: 1..47

(ix) FEATURE:
             (A) NAME/KEY: polymorphic base
             (B) LOCATION: 24
             (D) OTHER INFORMATION: base T (ix) FEATURE:
             (A) NAME/KEY: microsequencing oligos 4-14-mis1
             (B) LOCATION: 1..23

(ix) FEATURE:
             (A) NAME/KEY: microsequencing oligos 4-14-mis2
             (B) LOCATION: 25..47

(xi) SEQUENCE DESCRIPTION: SEQ ID NO: 23:

GCAGGGAGCA GACCAGACAT GATTTGTTCT AGTCTAGCTG ATTCATA                          47

(2) INFORMATION FOR SEQ ID NO: 24:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: polymorphic fragment 4-77
             (B) LOCATION: 1..47
             (D) OTHER INFORMATION: extracted from SEQ ID1 (12057..12103)
```

(ix) FEATURE:
    (A) NAME/KEY: polymorphic base
    (B) LOCATION: 24
    (D) OTHER INFORMATION: base C in PG1 (12080) SEQ ID1

(ix) FEATURE:
    (A) NAME/KEY: microsequencing oligos 4-77-mis1
    (B) LOCATION: 1..23

(ix) FEATURE:
    (A) NAME/KEY: microsequencing oligos 4-77-mis2
    (B) LOCATION: 25..47

(xi) SEQUENCE DESCRIPTION: SEQ ID NO: 24:

GCTGTTCAGA CTAAACTTGG AGACTACAGT CAGTCAGAGA ACTTGCT        47

(2) INFORMATION FOR SEQ ID NO: 25:

(i) SEQUENCE CHARACTERISTICS:
    (A) LENGTH: 47 base pairs
    (B) TYPE: NUCLEIC ACID
    (C) STRANDEDNESS: SINGLE
    (D) TOPOLOGY: LINEAR (ii) MOLECULE TYPE: DNA (vi) ORIGINAL SOURCE:
    (A) ORGANISM: Homo sapiens (ix) FEATURE:
    (A) NAME/KEY: polymorphic fragment 99-217
    (B) LOCATION: 1..47
    (D) OTHER INFORMATION: extracted from SEQ ID1 (34469..34515)

(ix) FEATURE:
    (A) NAME/KEY: polymorphic base
    (B) LOCATION: 24
    (D) OTHER INFORMATION: base C in PG1 (34492) SEQ ID1

(ix) FEATURE:
    (A) NAME/KEY: microsequencing oligos 99-217-mis1
    (B) LOCATION: 1..23

(ix) FEATURE:
    (A) NAME/KEY: microsequencing oligos 99-217-mis2
    (B) LOCATION: 25..47

(xi) SEQUENCE DESCRIPTION: SEQ ID NO: 25:

ATATAGTTCA CGTTATGTTC ATACTTAATT GTTGCATTTT GTTTGCC        47

(2) INFORMATION FOR SEQ ID NO: 26:

(i) SEQUENCE CHARACTERISTICS:
    (A) LENGTH: 47 base pairs
    (B) TYPE: NUCLEIC ACID
    (C) STRANDEDNESS: SINGLE
    (D) TOPOLOGY: LINEAR (ii) MOLECULE TYPE: DNA (vi) ORIGINAL SOURCE:
    (A) ORGANISM: Homo sapiens (ix) FEATURE:
    (A) NAME/KEY: polymorphic fragment 4-67
    (B) LOCATION: 1..47
    (D) OTHER INFORMATION: extracted from SEQ ID1 (51612..51658)

(ix) FEATURE:
    (A) NAME/KEY: polymorphic base
    (B) LOCATION: 24
    (D) OTHER INFORMATION: base C in PG1 (51635) SEQ ID1

(ix) FEATURE:
    (A) NAME/KEY: microsequencing oligos 4-67-mis1
    (B) LOCATION: 1..23

-continued (ix) FEATURE:
         (A) NAME/KEY: microsequencing oligos 4-67-mis2
         (B) LOCATION: 25..47

(xi) SEQUENCE DESCRIPTION: SEQ ID NO: 26:

GCCAGTGAAA TACAGACTTA ATTCGTCATG ACTGAACGAA TTTGTTT                47

(2) INFORMATION FOR SEQ ID NO: 27:

(i) SEQUENCE CHARACTERISTICS:
         (A) LENGTH: 47 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-213
         (B) LOCATION: 1..47

(ix) FEATURE:
         (A) NAME/KEY: polymorphic base
         (B) LOCATION: 24
         (D) OTHER INFORMATION: base T (ix) FEATURE:
         (A) NAME/KEY: microsequencing oligos 99-213-mis1
         (B) LOCATION: 1..23

(ix) FEATURE:
         (A) NAME/KEY: microsequencing oligos 99-213-mis2
         (B) LOCATION: 25..47

(xi) SEQUENCE DESCRIPTION: SEQ ID NO: 27:

CCTTAGCATT CAAGCCCCTG AGCTCTGGTG TTGTCCACCC CTGGGGG               47

(2) INFORMATION FOR SEQ ID NO: 28:

(i) SEQUENCE CHARACTERISTICS:
         (A) LENGTH: 47 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-221
         (B) LOCATION: 1..47

(ix) FEATURE:
         (A) NAME/KEY: polymorphic base
         (B) LOCATION: 24
         (D) OTHER INFORMATION: base A (ix) FEATURE:
         (A) NAME/KEY: microsequencing oligos 99-221-mis1
         (B) LOCATION: 1..23

(ix) FEATURE:
         (A) NAME/KEY: microsequencing oligos 99-221-mis2
         (B) LOCATION: 25..47

(xi) SEQUENCE DESCRIPTION: SEQ ID NO: 28:

AGCTTGAGAA ACCAGAAAAG CCAAAAGGAG GCTCCTACCA CATGGGT               47

(2) INFORMATION FOR SEQ ID NO: 29:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-135
        (B) LOCATION: 1..47

(ix) FEATURE:
        (A) NAME/KEY: polymorphic base
        (B) LOCATION: 24
        (D) OTHER INFORMATION: base A (ix) FEATURE:
        (A) NAME/KEY: microsequencing oligos 99-135-mis1
        (B) LOCATION: 1..23

(ix) FEATURE:
        (A) NAME/KEY: microsequencing oligos 99-135-mis2
        (B) LOCATION: 25..47

(xi) SEQUENCE DESCRIPTION: SEQ ID NO: 29:

AGTCACTATA TCTATGTTTA ATGAAGATAG AAAGAGATGC AGAAATG          47

(2) INFORMATION FOR SEQ ID NO: 30:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-123
        (B) LOCATION: 1..47
        (D) OTHER INFORMATION: variant version of SEQ ID21

(ix) FEATURE:
        (A) NAME/KEY: polymorphic base
        (B) LOCATION: 24
        (D) OTHER INFORMATION: base T ; C in SEQ ID21

(ix) FEATURE:
        (A) NAME/KEY: microsequencing oligos 99-123-mis1
        (B) LOCATION: 1..23

(ix) FEATURE:
        (A) NAME/KEY: microsequencing oligos 99-123-mis2
        (B) LOCATION: 25..47

(xi) SEQUENCE DESCRIPTION: SEQ ID NO: 30:

TTTCTCATCC TCACACCTCA CTGTGCCCCT CCTGAACCCA CTCCTTT          47

(2) INFORMATION FOR SEQ ID NO: 31:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-26
        (B) LOCATION: 1..47
        (D) OTHER INFORMATION: variant version of SEQ ID22

(ix) FEATURE:
        (A) NAME/KEY: polymorphic base
        (B) LOCATION: 24
        (D) OTHER INFORMATION: base A ; G in SEQ ID22

(ix) FEATURE:
        (A) NAME/KEY: microsequencing oligos 4-26-mis1
        (B) LOCATION: 1..23

(ix) FEATURE:
        (A) NAME/KEY: microsequencing oligos 4-26-mis2
        (B) LOCATION: 25..47

(xi) SEQUENCE DESCRIPTION: SEQ ID NO: 31:

CCCTGTNAGA CACGTCCTGT ATCATTGTTG AGATGGGAAA GTGCATC                47

(2) INFORMATION FOR SEQ ID NO: 32:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-14
        (B) LOCATION: 1..47
        (D) OTHER INFORMATION: variant version of SEQ ID23

(ix) FEATURE:
        (A) NAME/KEY: polymorphic base
        (B) LOCATION: 24
        (D) OTHER INFORMATION: base C ; T in SEQ ID23

(ix) FEATURE:
        (A) NAME/KEY: microsequencing oligos 4-14-mis1
        (B) LOCATION: 1..23

(ix) FEATURE:
        (A) NAME/KEY: microsequencing oligos 4-14-mis2
        (B) LOCATION: 25..47

(xi) SEQUENCE DESCRIPTION: SEQ ID NO: 32:

GCAGGGAGCA GACCAGACAT GATCTGTTCT AGTCTAGCTG ATTCATA                47

(2) INFORMATION FOR SEQ ID NO: 33:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-77
        (B) LOCATION: 1..47
        (D) OTHER INFORMATION: variant version of SEQ ID24

(ix) FEATURE:
        (A) NAME/KEY: polymorphic base
        (B) LOCATION: 24
        (D) OTHER INFORMATION: base G ; C in SEQ ID24

(ix) FEATURE:
        (A) NAME/KEY: microsequencing oligos 4-77-mis1
        (B) LOCATION: 1..23

(ix) FEATURE:
        (A) NAME/KEY: microsequencing oligos 4-77-mis2
        (B) LOCATION: 25..47

(xi) SEQUENCE DESCRIPTION: SEQ ID NO: 33:

GCTGTTCAGA CTAAACTTGG AGAGTACAGT CAGTCAGAGA ACTTGCT         47

(2) INFORMATION FOR SEQ ID NO: 34:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-217
        (B) LOCATION: 1..47
        (D) OTHER INFORMATION: variant version of SEQ ID25

(ix) FEATURE:
        (A) NAME/KEY: polymorphic base
        (B) LOCATION: 24
        (D) OTHER INFORMATION: base T ; C in SEQ ID25

(ix) FEATURE:
        (A) NAME/KEY: microsequencing oligos 99-217-mis1
        (B) LOCATION: 1..23

(ix) FEATURE:
        (A) NAME/KEY: microsequencing oligos 99-217-mis2
        (B) LOCATION: 25..47

(xi) SEQUENCE DESCRIPTION: SEQ ID NO: 34:

ATATAGTTCA CGTTATGTTC ATATTTAATT GTTGCATTTT GTTTGCC         47

(2) INFORMATION FOR SEQ ID NO: 35:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-67
        (B) LOCATION: 1..47
        (D) OTHER INFORMATION: variant version of SEQ ID26

(ix) FEATURE:
        (A) NAME/KEY: polymorphic base
        (B) LOCATION: 24
        (D) OTHER INFORMATION: base T ; C in SEQ ID26

(ix) FEATURE:
        (A) NAME/KEY: microsequencing oligos 4-67-mis1

(B) LOCATION: 1..23

(ix) FEATURE:
            (A) NAME/KEY: microsequencing oligos 4-67-mis2
            (B) LOCATION: 25..47

(xi) SEQUENCE DESCRIPTION: SEQ ID NO: 35:

GCCAGTGAAA TACAGACTTA ATTTGTCATG ACTGAACGAA TTTGTTT                47

(2) INFORMATION FOR SEQ ID NO: 36:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-213
            (B) LOCATION: 1..47
            (D) OTHER INFORMATION: variant version of SEQ ID27

(ix) FEATURE:
            (A) NAME/KEY: polymorphic base
            (B) LOCATION: 24
            (D) OTHER INFORMATION: base C ; T in SEQ ID27

(ix) FEATURE:
            (A) NAME/KEY: microsequencing oligos 99-213-mis1
            (B) LOCATION: 1..23

(ix) FEATURE:
            (A) NAME/KEY: microsequencing oligos 99-213-mis2
            (B) LOCATION: 25..47

(xi) SEQUENCE DESCRIPTION: SEQ ID NO: 36:

CCTTAGCATT CAAGCCCCTG AGCCCTGGTG TTGTCCACCC CTGGGGG                47

(2) INFORMATION FOR SEQ ID NO: 37:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-221
            (B) LOCATION: 1..47
            (D) OTHER INFORMATION: variant version of SEQ ID28

(ix) FEATURE:
            (A) NAME/KEY: polymorphic base
            (B) LOCATION: 24
            (D) OTHER INFORMATION: base C ; A in SEQ ID28

(ix) FEATURE:
            (A) NAME/KEY: microsequencing oligos 99-221-mis1
            (B) LOCATION: 1..23

(ix) FEATURE:
            (A) NAME/KEY: microsequencing oligos 99-221-mis2
            (B) LOCATION: 25..47

(xi) SEQUENCE DESCRIPTION: SEQ ID NO: 37:

AGCTTGAGAA ACCAGAAAAG CCACAAGGAG GCTCCTACCA CATGGGT                                47

(2) INFORMATION FOR SEQ ID NO: 38:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-135
        (B) LOCATION: 1..47
        (D) OTHER INFORMATION: variant version of SEQ ID29

(ix) FEATURE:
        (A) NAME/KEY: polymorphic base
        (B) LOCATION: 24
        (D) OTHER INFORMATION: base G ; A in SEQ ID29

(ix) FEATURE:
        (A) NAME/KEY: microsequencing oligos 99-135-mis1
        (B) LOCATION: 1..23

(ix) FEATURE:
        (A) NAME/KEY: microsequencing oligos 99-135-mis2
        (B) LOCATION: 25..47

(xi) SEQUENCE DESCRIPTION: SEQ ID NO: 38:

AGTCACTATA TCTATGTTTA ATGGAGATAG AAAGAGATGC AGAAATG                               47

(2) INFORMATION FOR SEQ ID NO: 39:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-123-PU upstream primer
        (B) LOCATION: 1..18

(xi) SEQUENCE DESCRIPTION: SEQ ID NO: 39:

AAAGCCAGGA CTAGAAGG                                                              18

(2) INFORMATION FOR SEQ ID NO: 40:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-26-PU upstream primer
        (B) LOCATION: 1..18

(xi) SEQUENCE DESCRIPTION: SEQ ID NO: 40:

```
TACAGCCCTG TAAGACAC                                                    18

(2) INFORMATION FOR SEQ ID NO: 41:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-14-PU upstream primer
        (B) LOCATION: 1..18

(xi) SEQUENCE DESCRIPTION: SEQ ID NO: 41:

TCTAACCTCT CATCCAAC                                                    18

(2) INFORMATION FOR SEQ ID NO: 42:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-77-PU upstream primer
        (B) LOCATION: 1..18
        (D) OTHER INFORMATION: extracted from seq SEQ ID1
            (11930..11947)

(xi) SEQUENCE DESCRIPTION: SEQ ID NO: 42:

TGTTGATTTA CAGGCGGC                                                    18

(2) INFORMATION FOR SEQ ID NO: 43:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-217-PU upstream primer
        (B) LOCATION: 1..19
        (D) OTHER INFORMATION: extracted from seq SEQ ID1
            (34216..34234)

(xi) SEQUENCE DESCRIPTION: SEQ ID NO: 43:

GGTGGGAATT TACTATATG                                                   19

(2) INFORMATION FOR SEQ ID NO: 44:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR
```

(ii) MOLECULE TYPE: DNA (vi) ORIGINAL SOURCE:
             (A) ORGANISM: Homo sapiens (ix) FEATURE:
             (A) NAME/KEY: 4-67-PU upstream primer
             (B) LOCATION: 1..18
             (D) OTHER INFORMATION: extracted from seq SEQ ID1
                 (51596..51613)

(xi) SEQUENCE DESCRIPTION: SEQ ID NO: 44:

AAGTTCACCT TCTCAAGC                                                    18

(2) INFORMATION FOR SEQ ID NO: 45:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: 99-213-PU upstream primer
             (B) LOCATION: 1..20

(xi) SEQUENCE DESCRIPTION: SEQ ID NO: 45:

ATACTGGCAG CGTGTGCTTC                                                  20

(2) INFORMATION FOR SEQ ID NO: 46:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: 99-221-PU upstream primer
             (B) LOCATION: 1..19

(xi) SEQUENCE DESCRIPTION: SEQ ID NO: 46:

CCCTTTTTCT TCACTGTTC                                                   19

(2) INFORMATION FOR SEQ ID NO: 47:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: 99-135-PU upstream primer
             (B) LOCATION: 1..18

(xi) SEQUENCE DESCRIPTION: SEQ ID NO: 47:

```
TGGAAGTTGT TATTGCCC                                            18

(2) INFORMATION FOR SEQ ID NO: 48:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-123-RP downstream primer
        (B) LOCATION: 1..18

(xi) SEQUENCE DESCRIPTION: SEQ ID NO: 48:

TATTCAGAAA GGAGTGGG                                             18

(2) INFORMATION FOR SEQ ID NO: 49:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-26-RP downstream primer
        (B) LOCATION: 1..18

(xi) SEQUENCE DESCRIPTION: SEQ ID NO: 49:

TGAGGACTGC TAGGAAAG                                             18

(2) INFORMATION FOR SEQ ID NO: 50:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-14-RP downstream primer
        (B) LOCATION: 1..20

(xi) SEQUENCE DESCRIPTION: SEQ ID NO: 50:

GACTGTATCC TTTGATGCAC                                           20

(2) INFORMATION FOR SEQ ID NO: 51:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
```

(A) ORGANISM: Homo sapiens (ix) FEATURE:
         (A) NAME/KEY: 4-77-RP downstream primer
         (B) LOCATION: 1..20
         (D) OTHER INFORMATION: extracted from seq SEQ ID1 compl
             (12339..12358)

(xi) SEQUENCE DESCRIPTION: SEQ ID NO: 51:

GGAAAGGTAC TCATTCATAG                                                    20

(2) INFORMATION FOR SEQ ID NO: 52:

(i) SEQUENCE CHARACTERISTICS:
         (A) LENGTH: 21 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: 99-217-RP downstream primer
         (B) LOCATION: 1..21
         (D) OTHER INFORMATION: extracted from seq SEQ ID1 compl
             (34625..34645)

(xi) SEQUENCE DESCRIPTION: SEQ ID NO: 52:

GTTTATTTTG TGTGAGCTTT G                                                  21

(2) INFORMATION FOR SEQ ID NO: 53:

(i) SEQUENCE CHARACTERISTICS:
         (A) LENGTH: 20 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: 4-67-RP downstream primer
         (B) LOCATION: 1..20
         (D) OTHER INFORMATION: extracted from seq SEQ ID1 compl
             (51996..52015)

(xi) SEQUENCE DESCRIPTION: SEQ ID NO: 53:

TGAAAGAGTT TATTCTCTGG                                                    20

(2) INFORMATION FOR SEQ ID NO: 54:

(i) SEQUENCE CHARACTERISTICS:
         (A) LENGTH: 21 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: 99-213-RP downstream primer
         (B) LOCATION: 1..21

(xi) SEQUENCE DESCRIPTION: SEQ ID NO: 54:

TTATTGCCCC ACATGCTTGA G                                    21

(2) INFORMATION FOR SEQ ID NO: 55:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-221-RP downstream primer
        (B) LOCATION: 1..19

(xi) SEQUENCE DESCRIPTION: SEQ ID NO: 55:

TCATTCGTCT GGCTAGGTC                                       19

(2) INFORMATION FOR SEQ ID NO: 56:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-135-RP downstream primer
        (B) LOCATION: 1..18

(xi) SEQUENCE DESCRIPTION: SEQ ID NO: 56:

AAACACCTCC CATTGTGC                                        18

(2) INFORMATION FOR SEQ ID NO: 57:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-1482
        (B) LOCATION: 1..47

(ix) FEATURE:
        (A) NAME/KEY: polymorphic base
        (B) LOCATION: 24
        (D) OTHER INFORMATION: base C (ix) FEATURE:
        (A) NAME/KEY: microsequencing oligos 99-1482-mis1
        (B) LOCATION: 1..23

(ix) FEATURE:
        (A) NAME/KEY: microsequencing oligos 99-1482-mis2
        (B) LOCATION: 25..47

(xi) SEQUENCE DESCRIPTION: SEQ ID NO: 57:

AGTGAAGTCT GAGGGGGAAA AATCAACCCT ATAGAGGGAA GGATCTG                    47

(2) INFORMATION FOR SEQ ID NO: 58:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-73
        (B) LOCATION: 1..47
        (D) OTHER INFORMATION: extracted from SEQ ID1 (13657..13703)

(ix) FEATURE:
        (A) NAME/KEY: polymorphic base
        (B) LOCATION: 24
        (D) OTHER INFORMATION: base C in PG1 (13680) SEQ ID1

(ix) FEATURE:
        (A) NAME/KEY: microsequencing oligos 4-73-mis1
        (B) LOCATION: 1..23

(ix) FEATURE:
        (A) NAME/KEY: microsequencing oligos 4-73-mis2
        (B) LOCATION: 25..47

(xi) SEQUENCE DESCRIPTION: SEQ ID NO: 58:

GTTTTCCTTA TGATGTTACA TGGCTTATTT TTAAAGGTAA TGAAAAC                    47

(2) INFORMATION FOR SEQ ID NO: 59:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-65
        (B) LOCATION: 1..47
        (D) OTHER INFORMATION: extracted from SEQ ID1 (51448..51494)

(ix) FEATURE:
        (A) NAME/KEY: polymorphic base
        (B) LOCATION: 24
        (D) OTHER INFORMATION: base T in PG1 (51471) SEQ ID1

(ix) FEATURE:
        (A) NAME/KEY: microsequencing oligos 4-65-mis1
        (B) LOCATION: 1..23

(ix) FEATURE:
        (A) NAME/KEY: microsequencing oligos 4-65-mis2
        (B) LOCATION: 25..47

(xi) SEQUENCE DESCRIPTION: SEQ ID NO: 59:

GGTGCTGCTC AGCGGCTTGC ACGTAGACTT GCTAGGAAGA AATGCAG                    47

155

(2) INFORMATION FOR SEQ ID NO: 60:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-1482
        (B) LOCATION: 1..47
        (D) OTHER INFORMATION: variant version of SEQ ID57

(ix) FEATURE:
        (A) NAME/KEY: polymorphic base
        (B) LOCATION: 24
        (D) OTHER INFORMATION: base A ; C in SEQ ID57

(ix) FEATURE:
        (A) NAME/KEY: microsequencing oligos 99-1482-mis1
        (B) LOCATION: 1..23

(ix) FEATURE:
        (A) NAME/KEY: microsequencing oligos 99-1482-mis2
        (B) LOCATION: 25..47

(xi) SEQUENCE DESCRIPTION: SEQ ID NO: 60:

```
AGTGAAGTCT GAGGGGGAAA AATAAACCCT ATAGAGGGAA GGATCTG                47
```

(2) INFORMATION FOR SEQ ID NO: 61:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 4-73
        (B) LOCATION: 1..47
        (D) OTHER INFORMATION: variant version of SEQ ID58

(ix) FEATURE:
        (A) NAME/KEY: polymorphic base
        (B) LOCATION: 24
        (D) OTHER INFORMATION: base G ; C in SEQ ID58

(ix) FEATURE:
        (A) NAME/KEY: microsequencing oligos 4-73-mis1
        (B) LOCATION: 1..23

(ix) FEATURE:
        (A) NAME/KEY: microsequencing oligos 4-73-mis2
        (B) LOCATION: 25..47

(xi) SEQUENCE DESCRIPTION: SEQ ID NO: 61:

```
GTTTTCCTTA TGATGTTACA TGGGTTATTT TTAAAGGTAA TGAAAAC                47
```

(2) INFORMATION FOR SEQ ID NO: 62:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
    (A) ORGANISM: Homo sapiens (ix) FEATURE:
    (A) NAME/KEY: polymorphic fragment 4-65
    (B) LOCATION: 1..47
    (D) OTHER INFORMATION: variant version of SEQ ID59

(ix) FEATURE:
    (A) NAME/KEY: polymorphic base
    (B) LOCATION: 24
    (D) OTHER INFORMATION: base C ; T in SEQ ID59

(ix) FEATURE:
    (A) NAME/KEY: microsequencing oligos 4-65-mis1
    (B) LOCATION: 1..23

(ix) FEATURE:
    (A) NAME/KEY: microsequencing oligos 4-65-mis2
    (B) LOCATION: 25..47

(xi) SEQUENCE DESCRIPTION: SEQ ID NO: 62:

GGTGCTGCTC AGCGGCTTGC ACGCAGACTT GCTAGGAAGA AATGCAG                47

(2) INFORMATION FOR SEQ ID NO: 63:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 99-1482-PU upstream primer
        (B) LOCATION: 1..21

(xi) SEQUENCE DESCRIPTION: SEQ ID NO: 63:

ATCAAATCAG TGAAGTCTGA G                                            21

(2) INFORMATION FOR SEQ ID NO: 64:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: 4-73-PU upstream primer
        (B) LOCATION: 1..18
        (D) OTHER INFORMATION: extracted from seq SEQ ID1
            (13547..13564)

(xi) SEQUENCE DESCRIPTION: SEQ ID NO: 64:

ATCGCTGGAA CATTCTGG                                                18

(2) INFORMATION FOR SEQ ID NO: 65:

(i) SEQUENCE CHARACTERISTICS:
        (A) LENGTH: 20 base pairs
        (B) TYPE: NUCLEIC ACID
        (C) STRANDEDNESS: SINGLE (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: 4-65-PU upstream primer
            (B) LOCATION: 1..20
            (D) OTHER INFORMATION: extracted from seq SEQ ID1
                (51149..51168)

(xi) SEQUENCE DESCRIPTION: SEQ ID NO: 65:

GATTTAAGCT ACGCTATTAG                                                   20

(2) INFORMATION FOR SEQ ID NO: 66:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: 99-1482-RP downstream primer
            (B) LOCATION: 1..20

(xi) SEQUENCE DESCRIPTION: SEQ ID NO: 66:

ACAAATCTAT ATAAGGCTGG                                                   20

(2) INFORMATION FOR SEQ ID NO: 67:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: 4-73-RP downstream primer
            (B) LOCATION: 1..20
            (D) OTHER INFORMATION: extracted from seq SEQ ID1 compl
                (13962..13981)

(xi) SEQUENCE DESCRIPTION: SEQ ID NO: 67:

CTCTTGGTTA AACAGCAGTG                                                   20

(2) INFORMATION FOR SEQ ID NO: 68:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: 4-65-RP downstream primer
            (B) LOCATION: 1..18

```
        (D) OTHER INFORMATION: extracted from seq SEQ ID1 compl
            (51482..51499)

(xi) SEQUENCE DESCRIPTION: SEQ ID NO: 68:

TGGCTCTGCA TTTCTTCC                                                         18
```